United States Patent
Xiong et al.

(10) Patent No.: US 11,078,188 B2
(45) Date of Patent: Aug. 3, 2021

(54) DIHYDROQUINOXALINE BROMODOMAIN RECOGNITION PROTEIN INHIBITOR, PREPARATION METHOD AND USE THEREOF

(71) Applicant: SHANGHAI INSTITUTE OF MATERIA MEDICA, CHINESE ACADEMY OF SCIENCES, Shanghai (CN)

(72) Inventors: Bing Xiong, Shanghai (CN); Jingkang Shen, Shanghai (CN); Zehong Miao, Shanghai (CN); Jianping Hu, Shanghai (CN); Yingqing Wang, Shanghai (CN); Shanshan Song, Shanghai (CN); Tao Meng, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 16/491,202

(22) PCT Filed: Mar. 5, 2018

(86) PCT No.: PCT/CN2018/078051
§ 371 (c)(1),
(2) Date: Sep. 5, 2019

(87) PCT Pub. No.: WO2018/161876
PCT Pub. Date: Sep. 13, 2018

(65) Prior Publication Data
US 2020/0031802 A1     Jan. 30, 2020

(30) Foreign Application Priority Data

Mar. 8, 2017    (CN) .......................... 201710134549.3

(51) Int. Cl.
| | |
|---|---|
| *A61K 31/498* | (2006.01) |
| *C07D 403/04* | (2006.01) |
| *A61P 35/00* | (2006.01) |
| *C07D 403/14* | (2006.01) |
| *C07D 405/14* | (2006.01) |
| *C07D 413/04* | (2006.01) |
| *C07D 417/04* | (2006.01) |
| *C07D 487/08* | (2006.01) |
| *C07D 491/107* | (2006.01) |
| *C07F 5/02* | (2006.01) |

(52) U.S. Cl.
CPC ............ *C07D 403/04* (2013.01); *A61P 35/00* (2018.01); *C07D 403/14* (2013.01); *C07D 405/14* (2013.01); *C07D 413/04* (2013.01); *C07D 417/04* (2013.01); *C07D 487/08* (2013.01); *C07D 491/107* (2013.01); *C07F 5/027* (2013.01)

(58) Field of Classification Search
None
See application file for complete search history.

(56) References Cited

U.S. PATENT DOCUMENTS 6,348,461 B1    2/2002   Takano et al.

FOREIGN PATENT DOCUMENTS

| CN | 1269794 A | 10/2000 | |
|---|---|---|---|
| WO | 2010/020366 A1 | 2/2010 | |
| WO | WO 2015/157093 | * 10/2015 | ........... C07D 401/14 |

OTHER PUBLICATIONS

English Translation of the International Search Report corresponding to PCT/CN2018/078051 dated Jun. 11, 2018; 2 pages.

* cited by examiner

*Primary Examiner* — Samantha L Shterengarts
(74) *Attorney, Agent, or Firm* — Mintz Levin Cohn Ferris Glovsky and Popeo PC

(57) ABSTRACT

The present invention relates to dihydroquinoxaline bromodomain recognition protein inhibitor, preparation method and use thereof. The inhibitor of the present invention is compound represented by general formula (I), or stereoisomer, pharmaceutically acceptable salt, prodrug, solvate, hydrate and crystal form thereof. The definition of each substituent is as described in the description and claims. The compound represented by general formula (I) of the present invention may inhibit bromodomain recognition protein and may be used for preparing medicament which regulates the apparent state of cells and treats series of diseases and symptoms which are mediated by the bromodomain recognition protein.

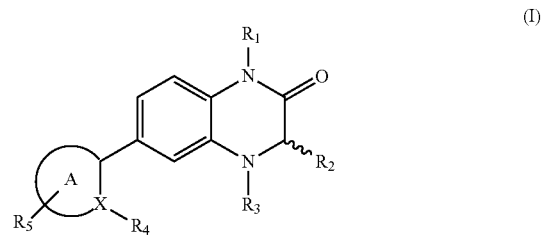

(I)

11 Claims, No Drawings

DIHYDROQUINOXALINE BROMODOMAIN RECOGNITION PROTEIN INHIBITOR, PREPARATION METHOD AND USE THEREOF

TECHNICAL FIELD

The present invention relates to a class of bromodomain recognition protein inhibitors having novel structures and a preparation method thereof, and to the use of such compounds in the manufacture of a medicament for the treatment of a disease mediated by a bromodomain recognition protein.

BACKGROUND TECHNIQUE

A region was found in female sterile homologous proteins of *drosophila* in 1992 and was named as bromodomains (BRDs). The bromodomain is a conserved domain in many chromatin and transcription-related proteins that can recognize acetylated lysine. So far, 61 bromodomains have been found in 46 different proteins in the human genome, which can be divided into eight major families, among which there are many studies on the BET (Bromo- and Extra-terminal) family. The BET family includes BRD2, BRD3, BRD4 widely expressed in tissues, and BRDT specifically expressed in testis tissue.

Studies have found that abnormalities in bromodomain protein are closely related to many diseases, such as cancer, inflammation, immune diseases, cardiovascular diseases and the like. The relationship between abnormalities in bromodomain protein and tumors is complex, and there is no specific pathway that causes tumors. One of the mechanisms may be that a bromodomain protein can form an oncogenic fusion protein, such as an oncogenic fusion protein found in NUT (a gene located on chromosome 15) midline cancer (NMC). In most NMCs, the NUT coding region is inserted into chromosome 19 at the 3' end of the BRD4 gene to form the BRD4-NUT fusion protein, and in a few cases, it is found to be a BRD3-NUT fusion protein. Knockout of the BRD4-NUT and BRD3-NUT fusion proteins results in squamous cell differentiation and cell replication arrest. Moreover, the bromodomain protein recognizes acetylated lysine and then can recruit transcription factors to induce downstream gene expression, such as the oncogene C-MYC, etc., and it is difficult to find small molecules to directly inhibit these genes, so gene expression can be indirectly inhibited by inhibiting bromodomain proteins. Therefore, it is meaningful to study the synthesis of selective inhibitors of bromodomain proteins.

In 2010, two BET family selective inhibitors (+)-JQ1 and I-BET762 were discovered, which led to widespread concern about bromodomain inhibitors. With the continuous efforts of researchers, more and more BET family selective inhibitors have been discovered and more and more researches on inhibitors of non-BET family bromodomain proteins have been made in recent years. These bromodomain protein inhibitors can facilitate better understand the function of the protein and its associated diseases.

In recent years, it has been found that many kinase inhibitors can also inhibit bromodomain proteins, especially BRD4, and it has been found that BRD4 exhibits the properties of atypical kinases, which can phosphorylate of serine at position 2 at C-terminal of the RNAC II. Among these kinase inhibitors, the PLK1 inhibitor BI2536 and the JAK2 inhibitor TG101209 have good activity against BRD4 with $IC_{50}$ of 25 nM and 130 nM, respectively.

There is still a need in the art to develop selective bromodomain recognition protein inhibitors, for reducing off-target side effects or providing more possibilities for future medicament combination.

SUMMARY OF THE INVENTION

The object of the present invention is to provide a selective bromodomain recognition protein inhibitor.

The first aspect of the invention provides a compound of the formula (I), or a stereoisomer, prodrug, solvate, hydrate, crystal form, or a pharmaceutically acceptable salt thereof:

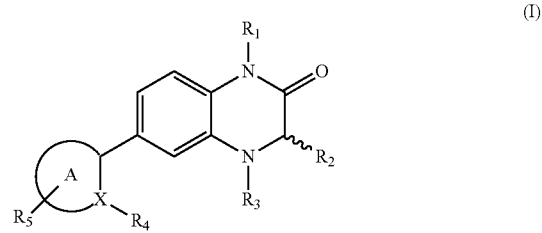

(I)

wherein, $R_1$, $R_2$, and $R_3$ are each independently hydrogen, substituted or unsubstituted C1-C6 alkyl, substituted or unsubstituted C1-C6 alkoxy, substituted or unsubstituted C3-C10 cycloalkyl, substituted or unsubstituted 3-8 membered heterocyclyl, substituted or unsubstituted —C(=O)Rx or substituted or unsubstituted benzyl; wherein Rx is C1-C6 alkyl, C1-C6 alkoxy or C3-C10 cycloalkyl;

the wavy line indicates that the configuration is R-type or S-type or a racemate;

A ring is 5-10 membered heteroaryl, 5-8 membered heterocyclyl, or C6-C10 aryl;

X is C or N;

$R_4$ is substituted or unsubstituted C6-C20 aryl, substituted or unsubstituted benzyl, 5-10 membered heterocyclyl or 5-10 membered heteroaryl;

$R_5$ is absent, hydrogen, substituted or unsubstituted C1-C6 alkyl,

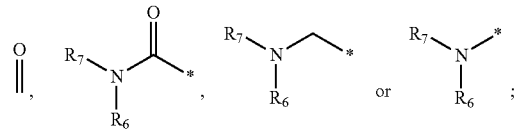

wherein $R_6$ and $R_7$ are each independently hydrogen, substituted or unsubstituted C1-C6 alkyl, substituted or unsubstituted C3-C10 cycloalkyl, substituted or unsubstituted C6-C20 aryl, substituted or unsubstituted benzyl, substituted or unsubstituted 5-10 membered heterocyclyl, or substituted or unsubstituted 5-10 membered heteroaryl; or $R_6$ and $R_7$ together with the nitrogen atom to which they are attached form substituted or unsubstituted 5-15 membered heterocyclyl;

the substitution means that there is one or more substituents selected from the group consisting of halogen, hydroxy, nitro, cyano, tert-butoxycarbonyl, C1-C6 alkyl, C1-C6 alkoxy, C3-C10 cycloalkyl and $NR_8R_9$; $R_8$ and $R_9$ are each independently hydrogen, C1-C6 alkyl, C3-C10 cycloalkyl, benzyloxycarbonyl (Cbz), tert-butoxycarbonyl (Boc), fluorenylmethoxycarbonyl (Fmoc), methoxycarbonyl, ethoxycarbonyl, phthaloyl (Pht), p-toluenesulfonyl (Tos), trifluoroacetyl (Tfa), pivaloyl, benzoyl, trityl (Trt), 2,4-dimethoxybenzyl (Dmb), p-methoxybenzyl (PMB), or benzyl (Bn).

In another preferred embodiment, A ring is C6-C10 aryl, 5-6 membered heterocyclyl or 5-6 membered heteroaryl.

In another preferred embodiment, $R_1$ is hydrogen, substituted or unsubstituted C1-C4 alkyl, or substituted or unsubstituted C1-C4 alkoxy, and the substituent is halogen, hydroxyl, amino, nitro or cyano.

In another preferred embodiment, $R_2$ is substituted or unsubstituted C1-C4 alkyl, substituted or unsubstituted C1-C4 alkoxy, and the substituent is halogen, hydroxyl, amino, nitro or cyano.

In another preferred embodiment, $R_3$ is substituted or unsubstituted C1-C4 alkyl, substituted or unsubstituted C1-C4 alkoxy, substituted or unsubstituted C3-C6 cycloalkyl, substituted or unsubstituted 3-8 membered heterocyclyl, substituted or unsubstituted —C(=O)Rx or substituted or unsubstituted benzyl, wherein Rx is C1-C6 alkyl, C1-C6 alkoxy or C3-C6 cycloalkyl, and the substituent is selected from the group consisting of halogen, hydroxy, amino, nitro, cyano, C1-C3 alkyl, and C1-C3 alkoxy.

In another preferred embodiment, $R_4$ is substituted or unsubstituted C6-C14 aryl, substituted or unsubstituted benzyl, substituted or unsubstituted group having 1-3 heteroatoms selected from N, O or S as follows: 5-8 membered heterocyclyl or 5-8 membered heteroaryl, the substitution means that there is 1-3 substituents and each substituent is independently halogen, hydroxy, amino, nitro, cyano, C1-C4 alkyl, or C1-C4 alkoxy.

In another preferred embodiment, $R_5$ is absent, hydrogen, substituted or unsubstituted C1-C4 alkyl,

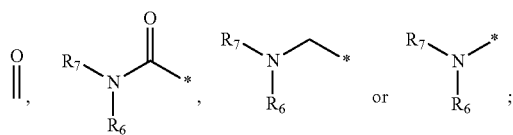

wherein $R_6$ and $R_7$ are each independently hydrogen, substituted or unsubstituted C1-C4 alkyl, substituted or unsubstituted C3-C8 cycloalkyl, substituted or unsubstituted C6-C14 aryl, substituted or unsubstituted benzyl, substituted or unsubstituted group having 1-3 heteroatoms selected from N, O or S as follows: 5-8 membered heterocyclyl, or 5-8 membered heteroaryl; the substitution means that there is 1-3 substituents and each substituent is independently halogen, hydroxy, amino, methylamino, cyano, N(C1-C4 alkyl)(C1-C4 alkyl), C1-C4 alkyl or C1-C4 alkoxy;

alternatively, $R_6$ and $R_7$ together with the nitrogen atom to which they are attached form substituted or unsubstituted 5-10 membered heterocyclyl containing 1-3 N, O, S heteroatoms, said substitution means that there is 1-3 substitutions and each substituent is independently halogen, $NR_8R_9$, hydroxy, nitro, cyano, tert-butyloxycarbyl, C1-C4 alkyl, C3-C8 cycloalkyl, or C1-C4 alkoxy; $R_8$ and $R_9$ are each independently hydrogen, benzyloxycarbonyl (Cbz), tert-butoxycarbonyl (Boc), methoxycarbonyl, ethoxycarbonyl, p-toluenesulfonyl (Tos), trifluoroacetyl (Tfa), pivaloyl, benzoyl, 2,4-dimethoxybenzyl (Dmb), p-methoxybenzyl (PMB) or benzyl (Bn).

In another preferred embodiment, the A ring is selected from the group consisting of phenyl, pyridyl, pyrimidinyl, triazolyl, tetrazolyl, thiazolidinyl, pyrazolyl, oxazolyl, isoxazolyl and imidazolyl.

In another preferred embodiment, $R_1$ is methyl, ethyl, n-propyl or isopropyl.

In another preferred embodiment, $R_2$ is methyl, ethyl, n-propyl or isopropyl.

In another preferred embodiment, $R_3$ is cyclopropyl, cyclobutyl, cyclopentyl, cyclohexyl,

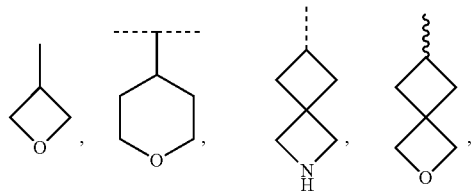

or —C(=O)Rx; wherein Rx is C1-C4 alkyl or C3-C6 cycloalkyl.

In another preferred embodiment, $R_4$ is substituted or unsubstituted C6-C10 aryl, substituted or unsubstituted benzyl, substituted or unsubstituted group having 1-3 hetero atom selected from N, O and S as follows: 5-6 membered heterocyclyl or 5-6 membered heteroaryl, substitution means that there is 1-3 substitutions, each of which is independently: fluorine, chlorine, bromine, hydroxy, amino, nitro, cyano, methyl, ethyl, n-propyl, isopropyl, methoxy, ethoxy, n-propoxy or isopropoxy.

In another preferred embodiment, $R_5$ is a hydrogen atom, substituted or unsubstituted methyl, substituted or unsubstituted ethyl, substituted or unsubstituted n-propyl, substituted or unsubstituted isopropyl,

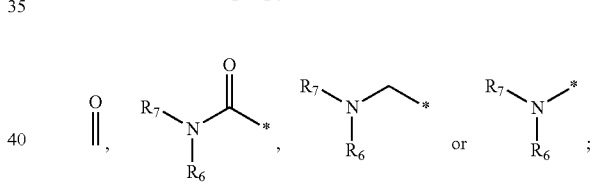

wherein $R_6$ and $R_7$ are each independently selected from a hydrogen atom, substituted or unsubstituted methyl, substituted or unsubstituted ethyl, substituted or unsubstituted n-propyl, substituted or unsubstituted isopropyl, substituted or unsubstituted piperidyl; substitution means that there is 1-3 substitutions, each of which is independently fluorine, chlorine, bromine, hydroxyl, amino, methylamino, cyano, —N(CH$_3$)$_2$, —N(CH$_2$CH$_3$)$_2$, —N(CH$_3$)(CH$_2$CH$_3$), methyl, ethyl, n-propyl, isopropyl, methoxy, ethoxy, n-propoxy or isopropoxy;

or $R_6$ and $R_7$ together with the nitrogen atom to which they are attached form substituted or unsubstituted group: piperazinyl, homopiperazinyl, piperidinyl,

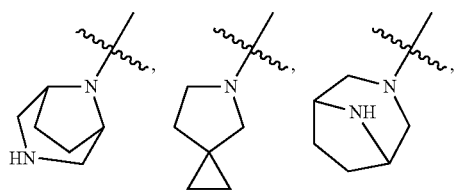

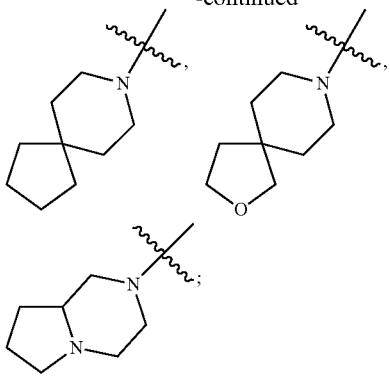

the substitution means there is 1 to 3 substituents and each substituent is independently fluorine, chlorine, bromine, hydroxyl, nitro, cyano, methyl, ethyl, n-propyl, isopropyl, cyclopropyl, cyclobutyl, cyclopentyl, cyclohexyl, tert-butoxycarbonyl or $NR_8R_9$; $R_5$ and $R_9$ are each independently hydrogen, tert-butoxycarbonyl (Boc), methoxycarbonyl, ethoxycarbonyl, pivaloyl, benzoyl or benzyl (Bn).

In another preferred embodiment, the A ring is selected from the group consisting of phenyl, triazolyl, tetrazolyl, thiazolidinyl, pyrazolyl and isoxazolyl; and X is C or N.

In another preferred embodiment, $R_1$ is a methyl.

In another preferred embodiment, $R_2$ is a methyl.

In another preferred embodiment, $R_3$ is cyclopropyl, cyclopentyl,

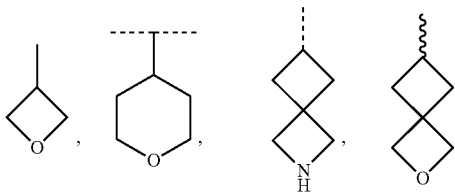

or —C(=O)Rx; wherein Rx is C1-C4 alkyl or C3-C6 cycloalkyl.

In another preferred embodiment, $R_4$ is substituted or unsubstituted group as follows: phenyl, oxazolyl, 1,3-dioxolanyl, and the substitution means there is 1 to 3 substituents, each of which is independently fluorine, chlorine and methyl.

In another preferred embodiment, $R_5$ is absent, hydrogen atom, methyl,

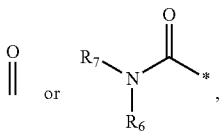

wherein $R_6$ and $R_7$ are each independently selected from a hydrogen atom, substituted or unsubstituted methyl, substituted or unsubstituted ethyl; and the substitution means there is 1 to 3 substituents, each of which is independently —$N(CH_3)_2$, methyl (preferably the substitution means substitution by —$N(CH_3)_2$); or, $R_6$ and $R_7$ together with the nitrogen atom to which they are attached form the following substituted or unsubstituted group: piperazinyl, homopiperazinyl,

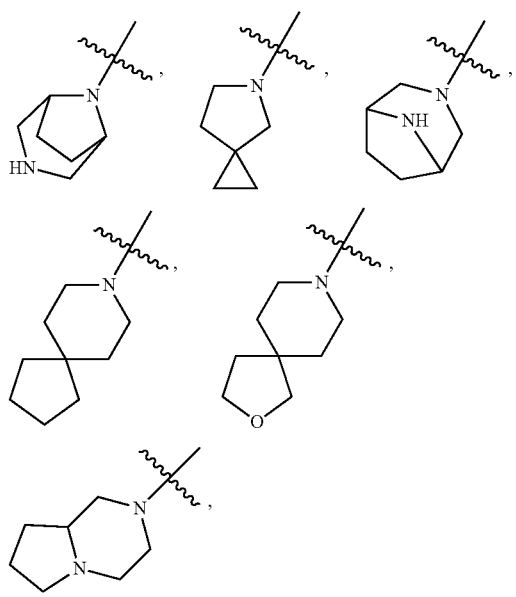

the substitution means there is 1 to 3 substituents, each of which is independently methyl, ethyl, isopropyl, cyclopropyl, $NH_2$, $N(CH_3)_2$, NHBoc.

In another preferred embodiment, the $R_1$, $R_2$, $R_3$, $R_4$, $R_5$, X, A ring and the wavy line are each independently the corresponding group of each specific compound in the examples.

In another preferred embodiment, the compound is:

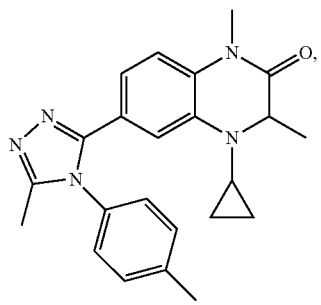

1

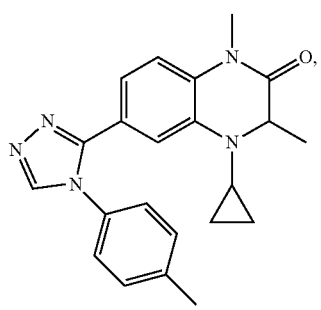

2

3
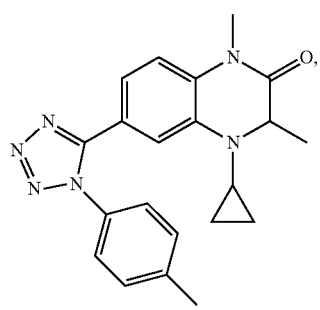
4
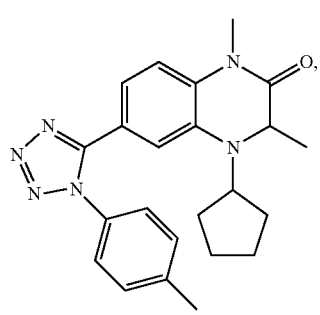
5
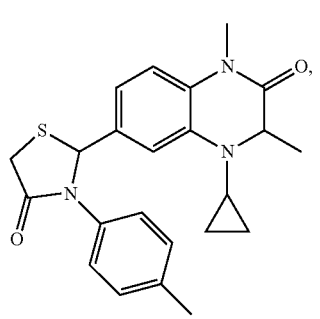
6
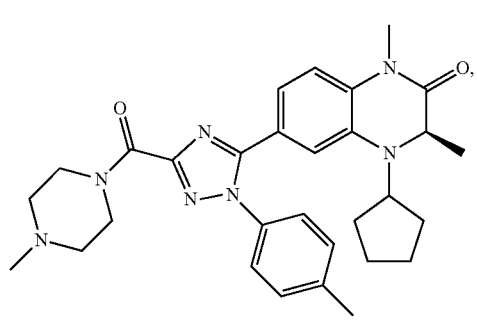
7
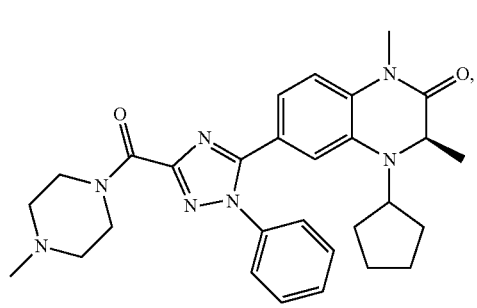
8
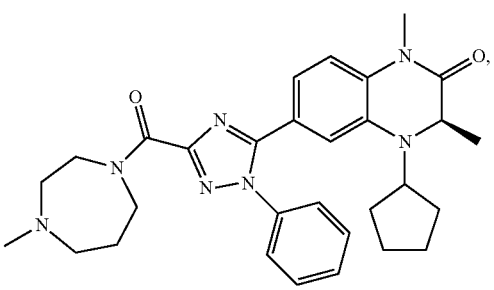
9
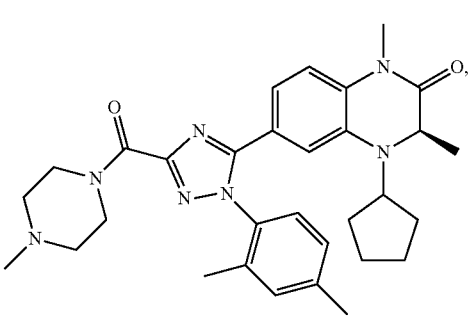
10
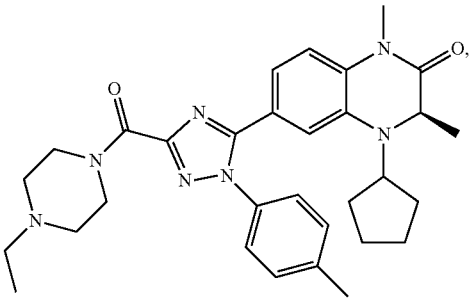
11
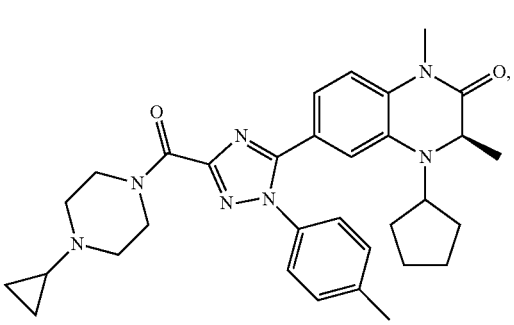
12
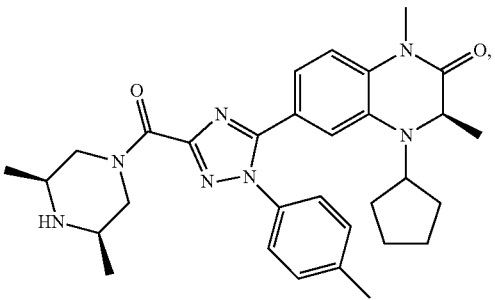

-continued
13
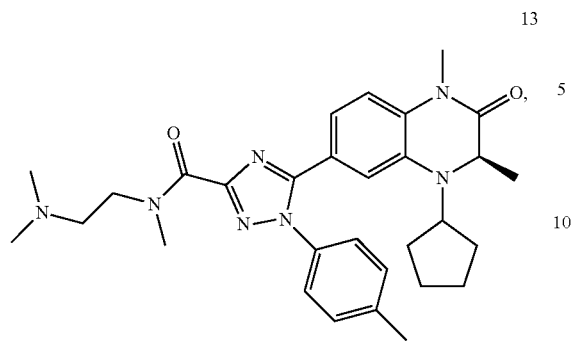
14
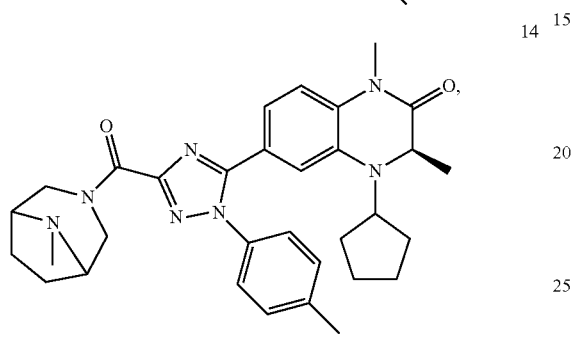
15
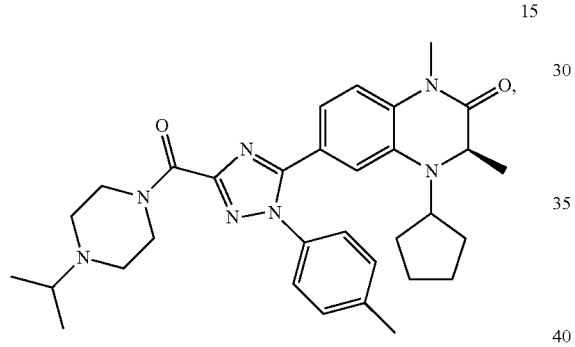
16
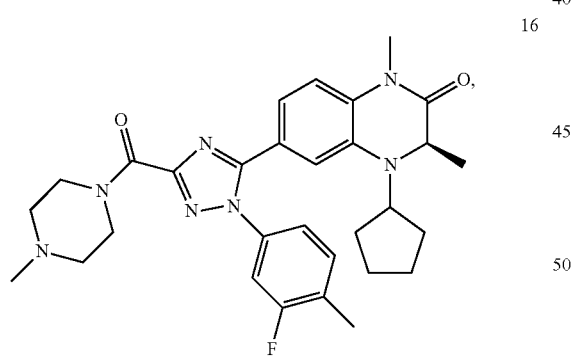
17
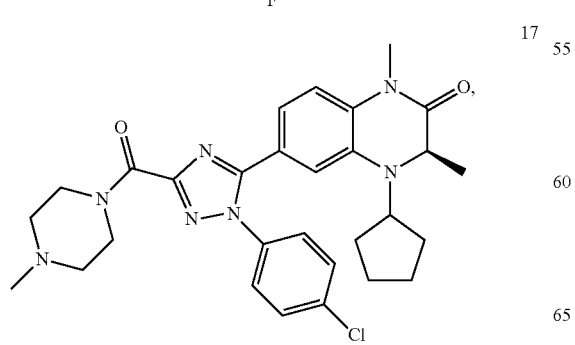
-continued
18
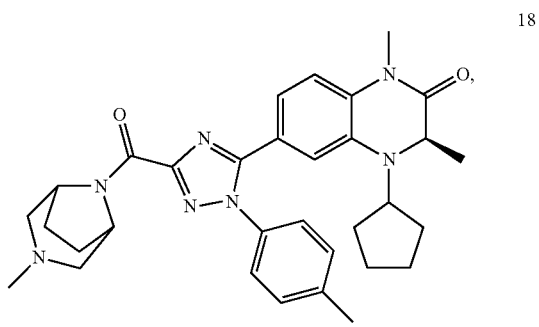
19
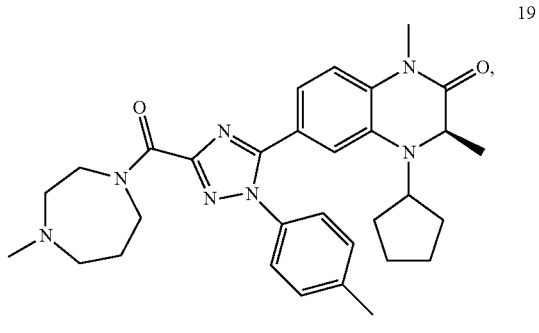
20
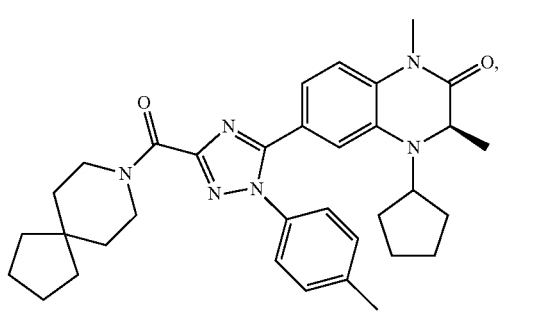
21
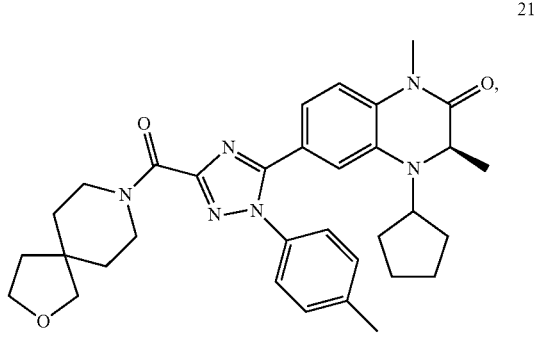
22
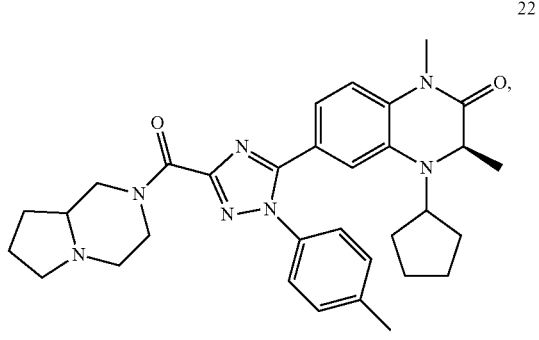

23
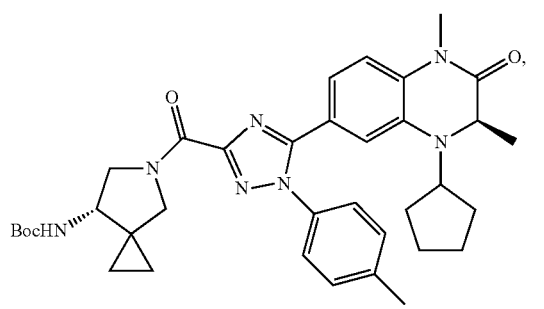
24
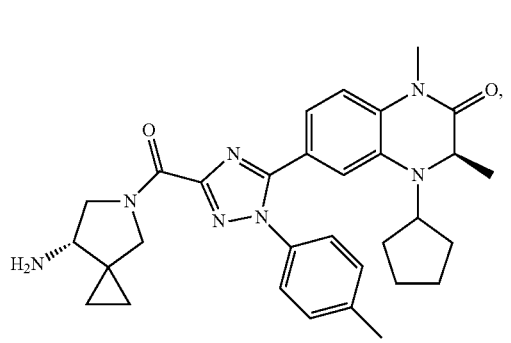
25
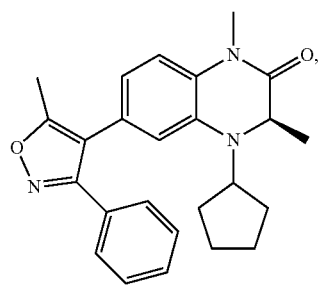
26
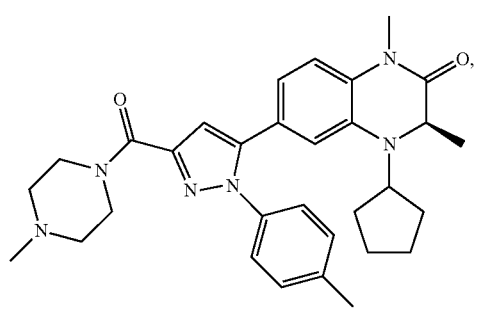
27
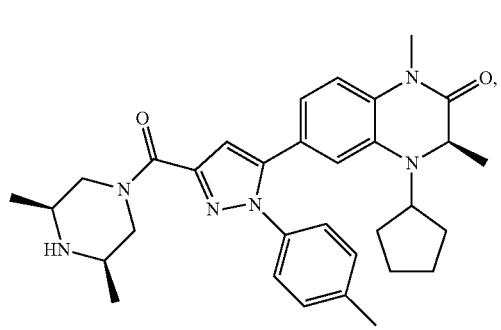
28
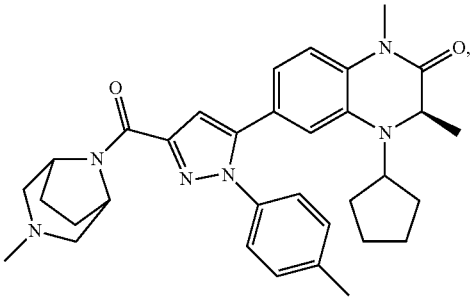
29
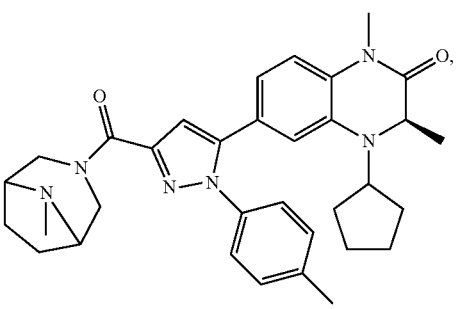
30
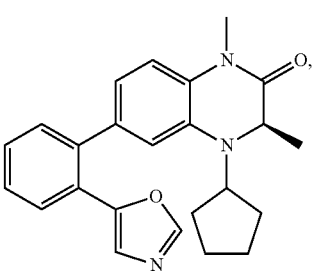
31
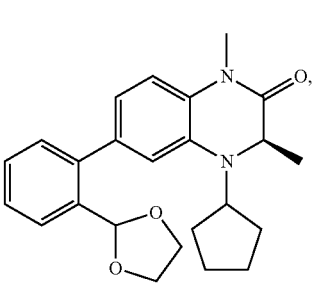
32
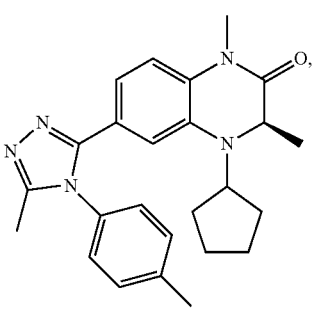

33
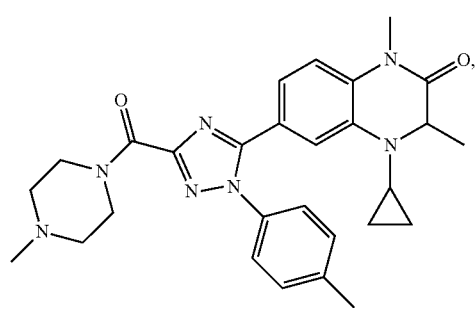
34
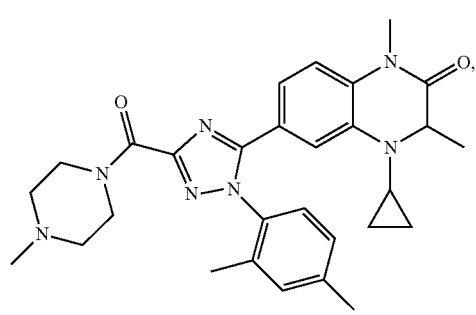
35
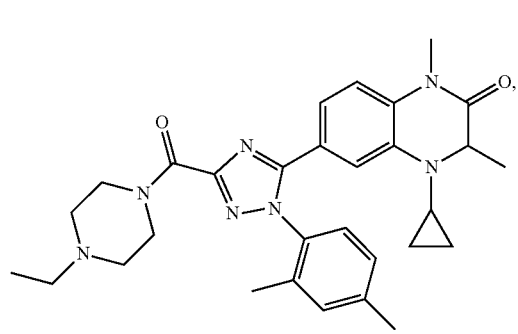
B1
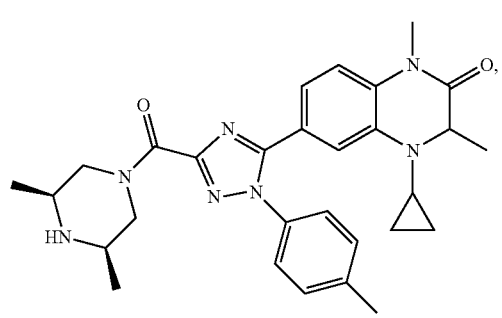
B2
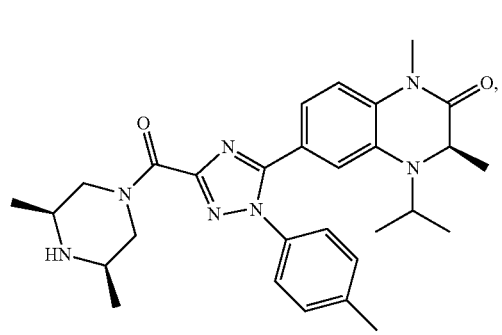
B3
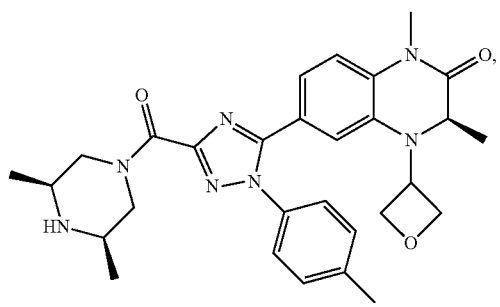
B4
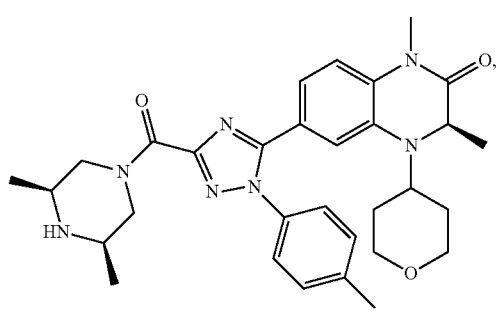
B5
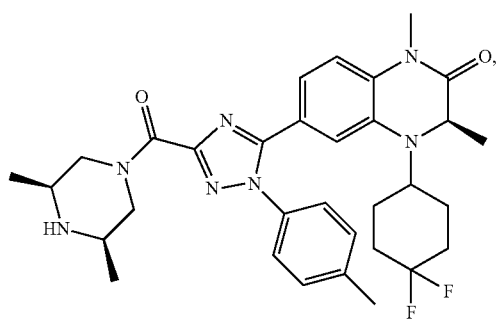
B6
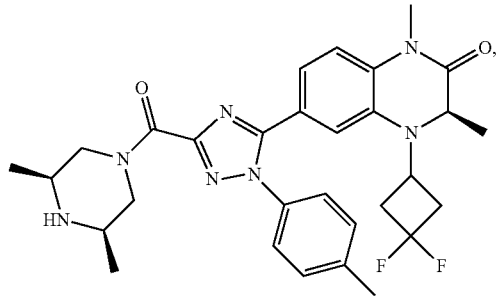

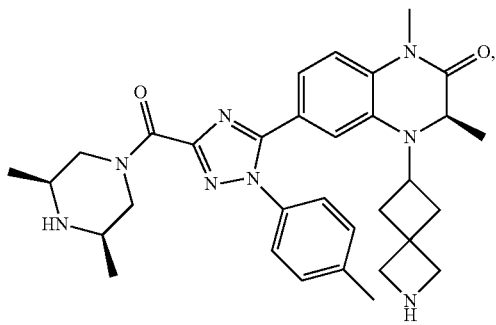
B7

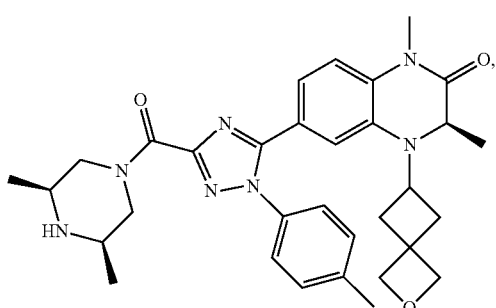
B8

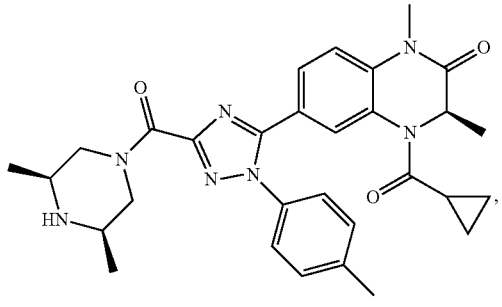
B9

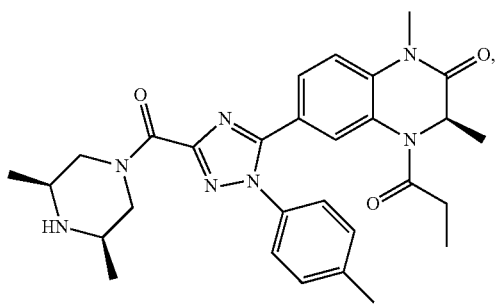
B10

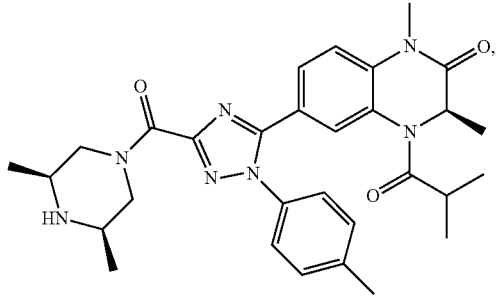
B11

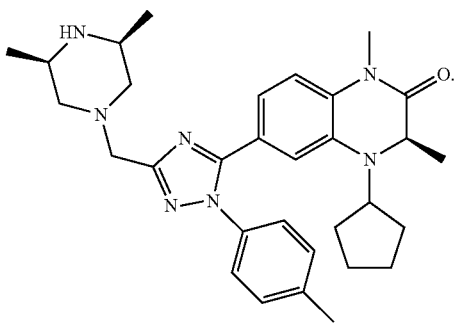
B12

The second aspect of the invention provides a method for the preparation of a compound of the first aspect, which comprises the step of preparing a compound of the formula I from a compound of the formula V,

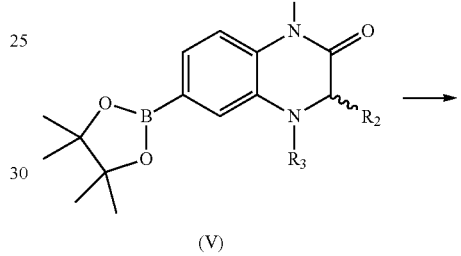

(V)

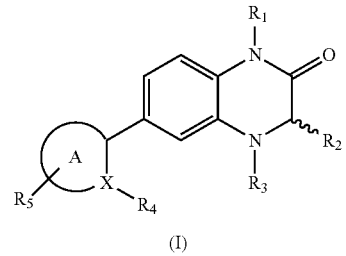

(I)

the preparation method comprises the step of preparing a compound of the formula I from a compound of the formula V, in each formula, the definition of each substituent and wavy line is as described above.

In another preferred embodiment, the preparation of the compound is as shown in the following scheme,

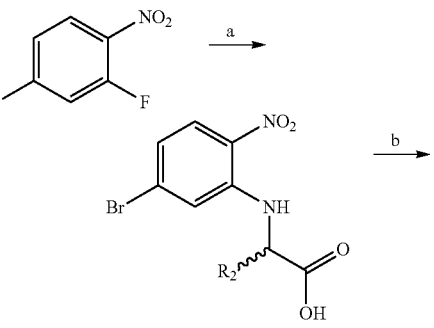

-continued

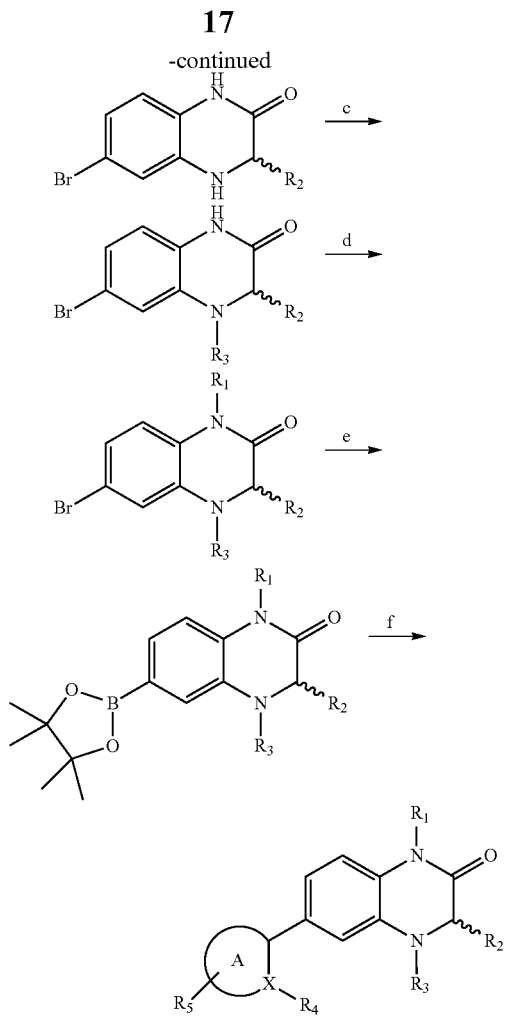

in each formula, the definition of each substituent and wavy line is as described above.

The third aspect of the invention provides a pharmaceutical composition comprising one or more of the compound of the formula (I), or the stereoisomer, prodrug, protein targeted degradation conjugate, solvant, hydrate, crystal form, or the pharmaceutically acceptable salt thereof according to the first aspect, and a pharmaceutically acceptable carrier.

The fourth aspect of the invention provides use of the compound of the formula (I), or the stereoisomer, prodrug, protein targeted degradation conjugate, solvant, hydrate, crystal form, or the pharmaceutically acceptable salt thereof according to the first aspect or use of the pharmaceutical composition of the third aspect, (i) for the manufacture of a selective inhibitor of a bromodomain recognition protein; or (ii) for the manufacture of a medicament for preventing or treating a related disease mediated by a bromodomain recognition protein.

In another preferred embodiment, the related disease mediated by the bromodomain recognition protein is selected from the group consisting of a malignant tumor, an immune disease, a cardiovascular disease, and an inflammation.

In another preferred embodiment, the malignant tumor is selected from the group consisting of acute lymphoblastic leukemia, acute myeloid leukemia, B cell chronic lymphocytic leukemia, chronic myelomonocytic leukemia, midline cancer, lung cancer, B cell lymphoma, prostate cancer, gastric cancer, colorectal cancer, kidney cancer, liver cancer, breast cancer and pancreatic cancer.

In a preferred embodiment of the invention, the protein targeted degradation conjugate is synthesized using a PROTAC (proteolysis targeting chimeric molecule) technique.

It should be understood that within the scope of the present invention, the various technical features of the present invention and the various technical features specifically described hereinafter (as in the examples) may be combined with each other to constitute a new or preferred technical solution. Due to space limitations, they will not be repeated herein.

DETAILED DESCRIPTION OF THE INVENTION

The inventors of the present application have extensively and intensively studied and developed for the first time a dihydroquinoxaline-based bromodomain recognition protein inhibitor having a novel structure shown in formula I. On the basis of this, the present invention has been completed.

Definition

Unless otherwise stated, the following terms used in this specification and claims have the meanings discussed below. The variables defined in this section, for example, $R_1$-$R_5$ and X, etc., are for reference only in this section and are not meant to have the same meaning as may be used in the definitions. Furthermore, many of the groups defined herein are optionally substituted. The list of typical substituents in this definition section is by way of example and is not intended to limit the substituents defined elsewhere in this specification and claims.

C1-C6 means that there is 1 to 6 carbon atoms, and C3-C10 means that there is 3 to 10 carbon atoms, and so on.

"5-8 membered" means that there are 5-8 atoms on the ring, and "5-10 membered" means 5-10 atoms on the ring, and so on.

"Alkyl" means a saturated aliphatic hydrocarbon group which is a branched alkyl or a linear alkyl.

"Cycloalkyl" means an all-carbon monocyclic ring, spiro ring, bridged ring or fused ring such as cyclopropyl, cyclopentyl or cyclohexyl.

"Alkoxy" means —O-(alkyl), such as methoxy, ethoxy;

"Aryl" means an all-carbon monocyclic ring or a fused ring polycyclic group having a complete conjugated n-electron system, and examples of aryls are, but not limited to, phenyl, naphthyl, and anthracenyl.

"Heterocyclyl" means a monocyclic ring, spiro ring, bridged ring or fused ring containing one, two, three, four or five ring heteroatoms selected from N, O, S or P, and the remaining ring atoms, if any, are C, such a ring may also have one or more double bonds, but such a ring does not have a complete conjugated n-electron system.

"Heteroaryl" means a monocyclic or fused ring containing one, two, three or four ring heteroatoms selected from N, O, S or P, the remaining ring atoms, if any, are C, and furthermore, and the ring has a complete conjugated n-electron system.

Compound of the Formula I

In the present invention, the compound represented by the formula (I), the compound of the formula I, and the compound as shown in the formula I all refer to a bromodomain recognition protein inhibitor having the following structure:

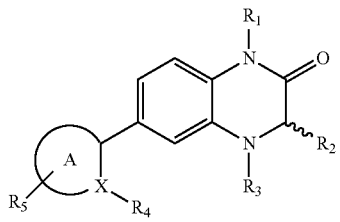

(I)

the definitions of each substituent and wavy line are as described above.

The compound represented by the formula (I) may contain an asymmetric or chiral center and thus may exist in different stereoisomeric forms. All stereoisomeric forms of the compounds of the invention, including but not limited to, are diastereomers, enantiomers, atropisomers, and mixtures thereof (e.g., racemic mixtures), which are included in the scope of the present invention.

The compounds of the formula (I) may also exist in different tautomeric forms, all of which are included in the scope of the present invention. The term "tautomer" or "tautomeric form" refers to structural isomers having different energies that are converted to each other via a low energy barrier.

The compound of the formula (I) may exist in unsolvated as well as solvated forms containing pharmaceutically acceptable solvents such as water, ethanol, and the like, and the compounds of the present invention include both solvated and unsolvated forms.

The compound represented by the formula (I) has a basic group and thus can form a pharmaceutically acceptable salt (ie, a medicinal salt) with an inorganic or organic acid, including a pharmaceutically acceptable acid addition salt. The pharmaceutically acceptable salt can be obtained by treating the free base of the compound of the formula (I) with an inorganic acid or an organic acid. The inorganic acid is, such as hydrochloric acid, hydrobromic acid, phosphoric acid or sulfuric acid, and the organic acid is, such as ascorbic acid, niacin, citric acid, tartaric acid, lactic acid, maleic acid, malonic acid, fumaric acid, oxalic acid, malic acid, glycolic acid, succinic acid, propionic acid, acetic acid, methanesulfonic acid, trifluoromethanesulfonic acid, benzenesulfonic acid, p-toluenesulfonic acid, etc.

The invention also encompasses isotopically-labeled compounds of the present invention, in addition to the fact that one or more atoms are replaced by an atom having an atomic mass or mass number different from the atomic mass or mass number common in nature. The others are the same as described above. Examples of isotopes which may be incorporated into the compounds of the present invention include isotopes of hydrogen, carbon, nitrogen, oxygen, phosphorus, sulfur, fluorine, iodine and chlorine, such as: $^{2}H$, $^{3}H$, $^{11}C$, $^{13}C$, $^{14}C$, $^{13}N$, $^{15}N$, $^{15}O$, $^{17}O$, $^{18}O$, $^{31}F$, $^{32}F$, $^{35}S$, $^{18}F$, $^{123}I$, $^{125}I$ and $^{35}Cl$.

Certain isotopically-labeled compounds of the present invention (such as those labeled with $^{3}H$ and $^{14}C$) are used in compound and/or substrate tissue distribution assays. Deuterated (i.e., $^{3}H$) and carbon-14 (i.e., $^{14}C$) isotopes are particularly preferred because of easy preparation and detection. Moreover, substitution by heavier isotopes such as deuterium (ie, $^{2}H$) may provide certain therapeutic advantages resulting from greater metabolic stability (eg, increased in vivo half-life or reduced dosage requirements), and thus it may be preferred in some cases. Positron emission isotopes, such as $^{15}O$, $^{13}N$, $^{11}C$, and $^{18}F$, are used in positron emission tomography (PET) studies to examine substrate receptor occupancy. Isotopically labeled compounds of the present invention can generally be prepared by replacing the non-isotopically labeled reagent with an isotopically labeled reagent, following procedures similar to those disclosed in the schemes and/or the examples below.

Unless otherwise defined, all professional and scientific terms used herein have the same meaning as known by those skilled in the art. In addition, any methods and materials similar or equivalent to those described herein may be employed in the methods of the present invention. The preferred embodiments and materials described herein are for illustrative purposes only.

Preparation Method

For illustrative purposes, the reaction schemes shown below provide possible pathways for the synthesis of the compounds of the present invention as well as key intermediates. For a more detailed description of the individual reaction step, please see the examples section below. The compounds of the formula (I) of the present invention can be synthesized by methods including those well known in the chemical arts, especially in accordance with the description of the present invention. The starting materials are generally available from commercial sources such as Sigma Aldrich or are readily prepared using methods well known to those skilled in the art.

The compound in the reaction scheme includes a salt thereof, for example, a salt as defined by the compound of the formula (I), etc., i.e., a free base of the compound treated with an organic acid or a mineral acid, to give a salt of the corresponding compound.

The preparation method of the above compound represented by the structural formula (I) includes:

Reaction route 1:

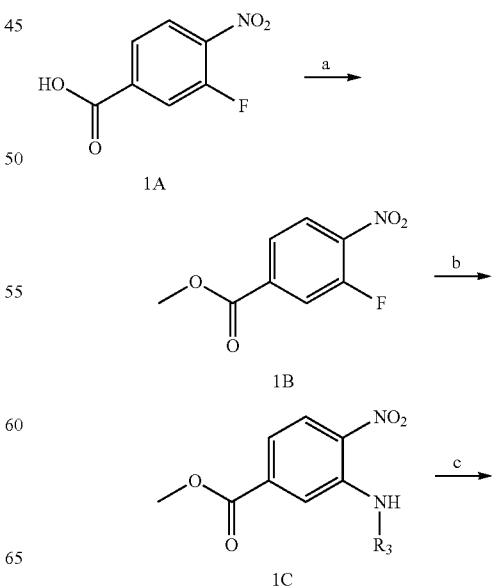

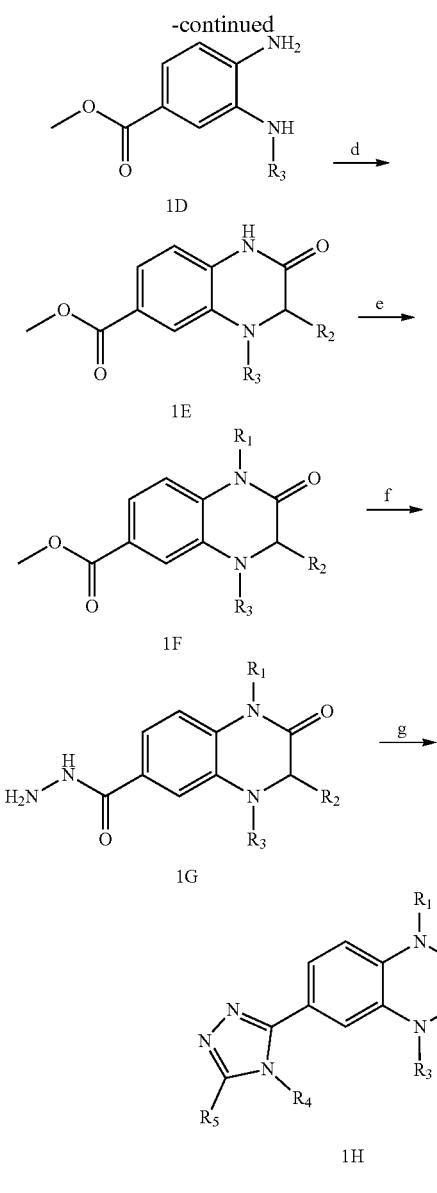

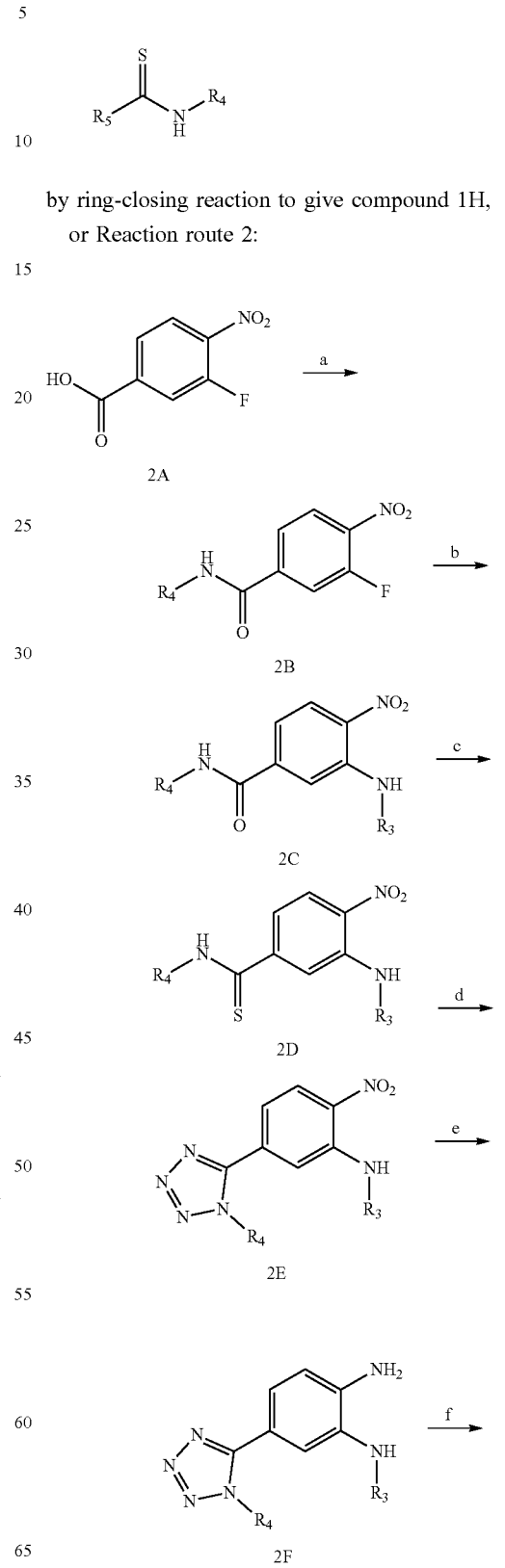

step f: reacting compound 1F with hydrazine hydrate to obtain compound 1G;

step g: reacting compound 1G with a different sulfamide

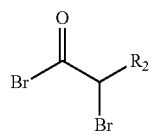

by ring-closing reaction to give compound 1H, or Reaction route 2:

step a: reacting compound 1A with thionyl chloride and methanol to obtain compound 1B;

step b: reacting compound 1B with a different primary amine R₃NH₂ by nucleophilic substitution to give compound 1C;

step c: reducing compound 1C under iron powder and ammonium chloride to obtain compound 1D;

step d: 1) reacting compound 1D with a different 2-bromoalkanoyl bromide to give an intermediate, 2) reacting the intermediate by intramolecular nucleophilic reaction in the presence of N,N-diisopropylethylamine to obtain compound 1E;

step e: reacting compound 1E with R₁I or R₁Br in the presence of sodium hydride to obtain compound 1F;

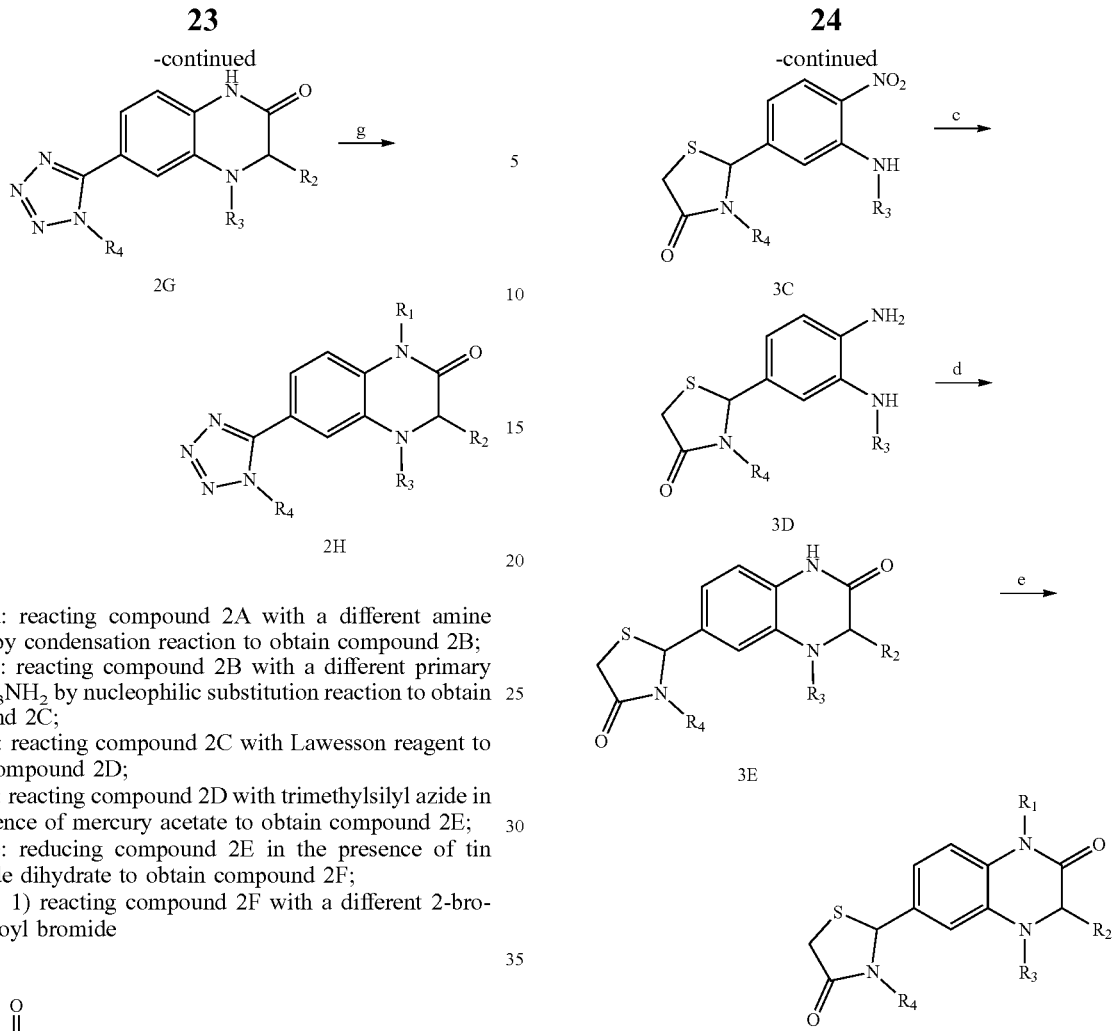

step a: reacting compound 2A with a different amine $R_4NH_2$ by condensation reaction to obtain compound 2B;

step b: reacting compound 2B with a different primary amine $R_3NH_2$ by nucleophilic substitution reaction to obtain compound 2C;

step c: reacting compound 2C with Lawesson reagent to obtain compound 2D;

step d: reacting compound 2D with trimethylsilyl azide in the presence of mercury acetate to obtain compound 2E;

step e: reducing compound 2E in the presence of tin dichloride dihydrate to obtain compound 2F;

step f: 1) reacting compound 2F with a different 2-bromoalkanoyl bromide

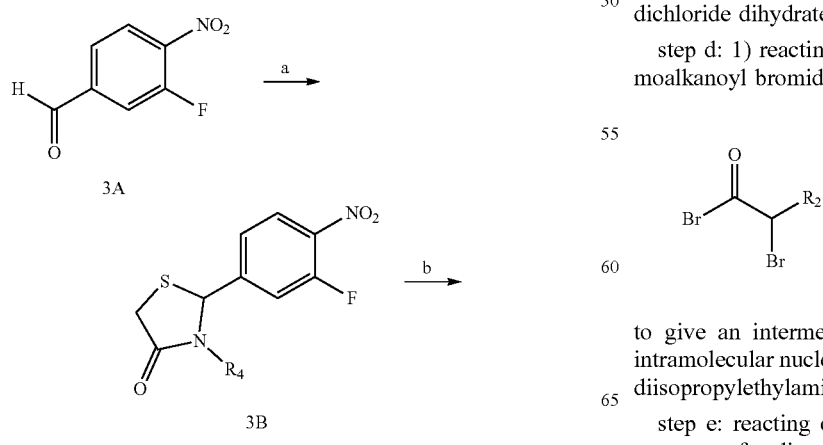

to give an intermediate, 2) reacting the intermediate by intramolecular nucleophilic reaction in the presence of N,N-diisopropylethylamine to obtain compound 2G;

step g: reacting compound 2G with $R_1I$ or $R_1Br$ in the presence of sodium hydride to obtain compound 2H, or Reaction route 3:

step a: reacting compound 3A with thioglycolic acid and a different amine $R_4NH_2$ in the presence of dicyclohexylcarbodiimide conditions by ring-closing reaction to give compound 3B;

step b: reacting compound 3B with a different primary amine $R_3NH_2$ by nucleophilic substitution reaction to obtain compound 3C;

step c: reducing compound 3C in the presence of tin dichloride dihydrate to obtain compound 3D;

step d: 1) reacting compound 3D with a different 2-bromoalkanoyl bromide to give an intermediate, 2) reacting the intermediate by intramolecular nucleophilic reaction in the presence of N,N-diisopropylethylamine to obtain compound 3E;

step e: reacting compound 3E with $R_1I$ or $R_1Br$ in the presence of sodium hydride to obtain compound 3F, or Reaction route 4:

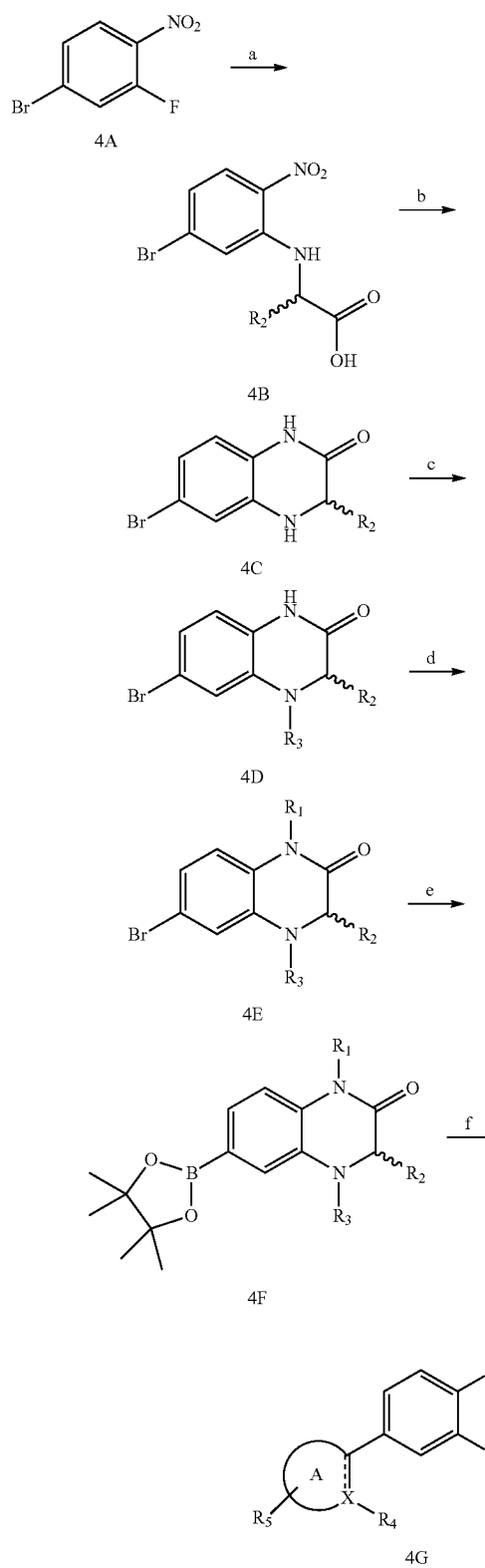

step a: reacting compound 4A with amino acid NH₂R₂COOH in the presence of potassium carbonate to obtain compound 4B;

step b: reacting compound 4B in the presence of sodium dithionite and potassium carbonate to obtain compound 4C;

step c: reacting compound 4C and different ketone

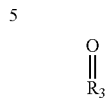

in the presence of phenylsilane and dibutyltin dichloride by reductive amination reaction or with different acid chloride by condensation reaction with to obtain compound 4D;

step d: reacting compound 4D with $R_1I$ or $R_1Br$ in the presence of sodium hydride to obtain compound 4E;

step e: reacting compound 4E and bis(pinacolato)diboron in the presence of potassium acetate and [1,1'-bis(diphenylphosphino)ferrocene]palladium chloride dichloromethane complex to obtain compound 4F;

step f: coupling compound 4F with a different ring

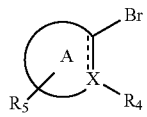

in the presence of sodium bicarbonate and [1,1'-bis(diphenylphosphino)ferrocene]palladium dichloride dichloromethane complex to obtain compound 4G, or Reaction route 5:

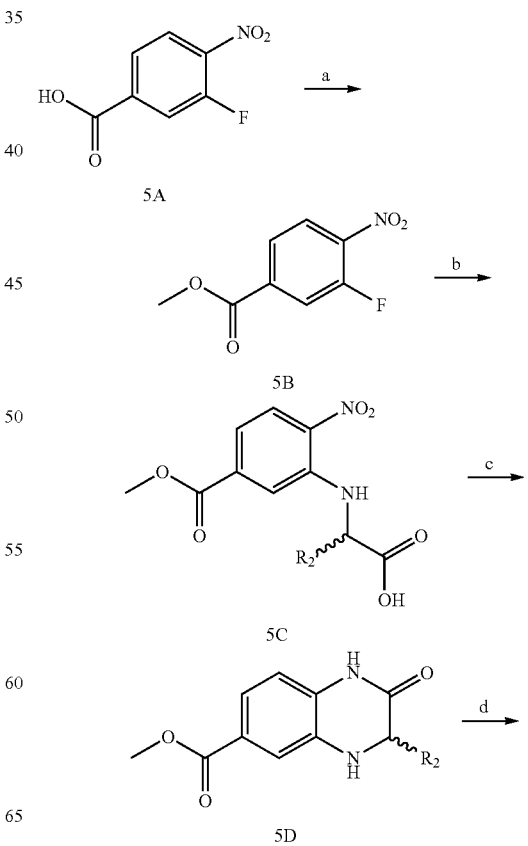

-continued

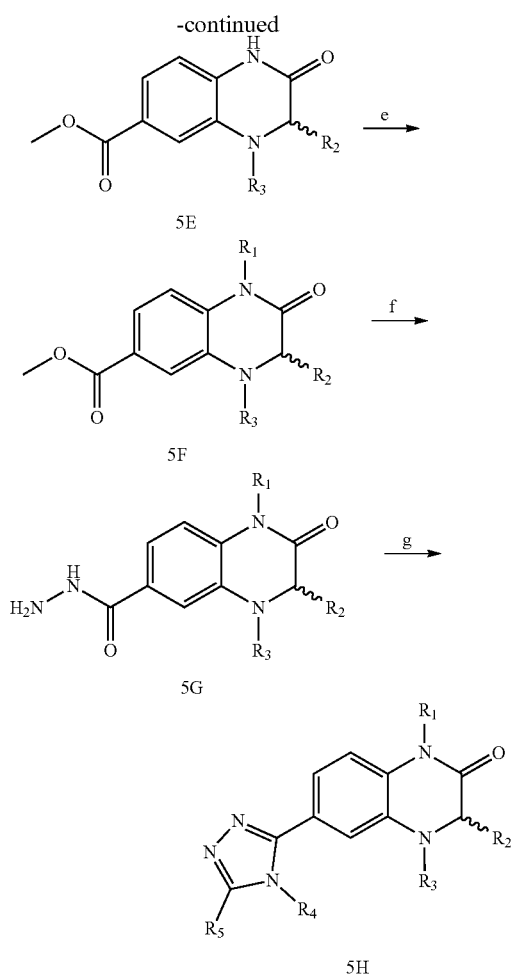

step a: reacting compound 5A with thionyl chloride and methanol to obtain compound 5B;

step b: reacting compound 5B with amino acid $NH_2R_2COOH$ in the presence of potassium carbonate to obtain compound 5C;

step c: reacting compound 5C in the presence of sodium dithionite and potassium carbonate to obtain compound 5D;

step d: reacting compound 5D and different ketone

in the presence of phenylsilane and dibutyltin dichloride to obtain compound 5E;

step e: reacting compound 5E with $R_1I$ or $R_1Br$ in the presence of sodium hydride to obtain compound 5F;

step f: reacting compound 5F with hydrazine hydrate to obtain compound 5G;

step g: reacting compound 5G with a different sulfamide

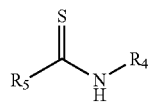

by ring-closing reaction to give compound 5H.

The Reaction route 5 provides another method for synthesizing the compound wherein A ring is a triazole, similar to Reaction route 1, but Reaction route 5 provides a synthetic method for the compound having a parent core with $R_2$ being an R form, an S form, or a racemate. Reaction route 1 only provides the synthesis method for the compound having a parent core with $R_2$ being a racemate.

In the above reaction scheme, $R_1$-$R_5$, X and A ring are as defined above, and the dotted line indicates the absence or single bond.

Pharmaceutical Composition

A "pharmaceutical composition" comprises one or more compounds described herein, or a physiologically/pharmaceutically acceptable salt, solvate, hydrate or prodrug thereof, and a pharmaceutically acceptable carrier, for example, a mixture of other chemical components such as physiologically/pharmaceutically acceptable carriers and excipients. The purpose of the pharmaceutical composition is to facilitate the administration of the compound to an organism.

As used herein, the term "physiologically/pharmaceutically acceptable carrier" means that the carrier, excipient or diluent does not cause significant irritation to the organism and does not abrogate the biological activity and properties of the administered compound.

The term "pharmaceutically acceptable excipient" means an inert material that is added to a pharmaceutical composition to further aid in the administration of the compound. Examples of excipients include, but are not limited to, calcium carbonate, calcium phosphate, various sugars and starches, cellulose derivatives, gelatin, vegetable oils and polyethylene glycols.

In another preferred embodiment, the pharmaceutical composition of the present invention comprises a therapeutically effective amount of one or more of the compound represented by the formula (I), and stereoisomer, pharmaceutically acceptable salt, prodrug, solvate, hydrate and crystal form thereof, and at least one excipient, diluent or carrier.

The term "therapeutically effective amount" means an amount of a compound administered which will alleviate one or more conditions of the conditions being treated to some extent, and for the treatment of cancer, a therapeutically effective amount means that the amount has at least one of the following effects:

(1) reducing tumor size;
(2) inhibiting (i.e, slowing down to some extent, preferably stopping) tumor metastasis;
(3) inhibiting tumor growth to a certain extent (ie, slowing down to some extent, preferably stopping)
(4) alleviating one or more conditions associated with cancer to some extent (or preferably eliminating).

Further, the compound represented by the general formula (I) of the present invention, and a stereoisomer, pharmaceutically acceptable salt, prodrug, solvate, hydrate or crystal form thereof can be used in monotherapy or combination therapy.

When used in combination therapy, the compound of the formula (I) of the present invention, and stereoisomer, pharmaceutically acceptable salt, prodrug, solvates, hydrate and crystal form thereof are generally used in combination with a therapy based on small molecule compound, radiation, antibody (e.g., Herceptin and Rituxima), anti-cancer vaccination, gene therapy, cell therapy, hormone therapy, or cytokine therapy.

A typical formulation is prepared by mixing the compound of the formula (I) of the present invention with a carrier, diluent or excipient. Suitable carriers, diluents or excipients are well known to those skilled in the art and include, for example, carbohydrates, waxes, water soluble and/or swellable polymers, hydrophilic or hydrophobic materials, gelatin, oil, solvent or water. The particular carrier, diluent or excipient used will depend on the mode and purpose for which the compound of the present invention is applied. The solvent is generally selected based on a solvent which is considered safely (GRAS) to a mammal in the art. In general, safe solvents are non-toxic aqueous solvents such as water, as well as other non-toxic solvents that are soluble in water or miscible with water. Suitable aqueous solvents include mixtures of one or more of water, ethanol, propylene glycol, polyethylene glycol (e.g., PEG400, PEG300), and the like. The formulation may also include one or more buffers, stabilizers, surfactants, wetting agents, lubricants, emulsifiers, suspending agents, preservatives, antioxidants, opacifiers, glidants, processing aids, coloring agents, sweeteners, flavoring agents, flavoring agents or other known additives to provide a beautiful presentation of the medicament (ie, a compound of the present invention or a pharmaceutical composition thereof), or to assist the manufacture of the pharmaceutical product (also that is, medicaments).

This formulation can be prepared using conventional dissolution mixing procedures. For example, in the presence of one or more of the above-mentioned excipients, a block-like medicament substance (i.e., a compound represented by the formula (I) of the present invention or a stabilized form of the compound (e.g., a complex of dextrin derivative or other known complexing agents) is dissolved in a suitable solvent. The compound represented by the general formula (I) of the present invention is typically formulated into a pharmaceutical dosage form to provide an easily controlled dose of the medicament, and to provide a patient with an easily treatable product.

In accordance with the methods of the present invention, a compound of the present invention or a combination of a compound of the present invention and at least one other agent (referred to herein as "combination") is preferably administered in the form of a pharmaceutical composition. Thus, the compounds or combinations of the present invention can be administered orally, rectally, transdermally, parenterally (e.g., intravenously, intramuscularly, or subcutaneously), intracisternally, intravaginally, intraperitoneally, intravesically, locally (e.g., powder, ointment or droplet), or in a buccal or nasal dosage forms, administered separately or together to a patient.

The composition suitable for parenteral injection generally comprises a pharmaceutically acceptable sterile aqueous or nonaqueous solution, dispersion liquid, suspension liquid or emulsion, and sterile powder for reconstitution into a sterile injectable solution or dispersion liquid. Suitable aqueous or non-aqueous vehicles or diluents (including solvents and carriers) include one of water, ethanol, polyol (propylene glycol, polyethylene glycol, glycerol, etc.) and mixture thereof; vegetable oils (such as olive oil); and injectable organic esters such as ethyl oleate. The required particle size can be maintained, for example, by the use of a coating such as lecithin in the case of dispersion liquid, or the suitable fluidity can be maintained by using surfactants.

These compositions may also contain excipients such as preservatives, wetting agents, emulsifying agents and dispersing agents. Microbial contamination of the composition can be avoided by various bactericides and fungicides, such as paraben, chlorobutanol, phenol, sorbic acid, and the like. These compositions may also include isotonic agents such as sugars, sodium chloride, and the like. The absorption of the injectable pharmaceutical compositions can also be extended by the use of agents which delay absorption, such as aluminum monostearate and gelatin.

Solid dosage forms for oral administration can include capsules, tablets, powders, and granules. In a solid dosage form, the compound or combination of the present invention is admixed with at least one inert excipient, diluent or carrier. Suitable excipients, diluents or carriers include those such as sodium citrate or dicalcium phosphate, or (a) fillers or extenders (such as starch, lactose, sucrose, mannitol, silicic acid, etc.); (b) binders (such as carboxymethylcellulose, alginate, gelatin, polyvinylpyrrolidone, sucrose, gum arabic, etc.); (c) wetting agents (such as glycerin, etc.); (d) disintegrants (such as agar, calcium carbonate, potato or tapioca starch, alginic acid, specific complex silicate, sodium carbonate, etc.); (e) solution blockers (such as paraffin, etc.); (f) accelerated absorbers (such as quaternary ammonium compounds); (g) wetting agents (such as acetyl alcohol, glyceryl monostearate, etc.); (h) adsorbents (such as kaolin, bentonite, etc.); and/or i) lubricants (such as talc, calcium stearate, magnesium stearate, solid polyethylene glycol, sodium lauryl sulfate, etc.). In the case of capsules and tablets, the dosage form may also include a buffer. A similar type of solid compositions may also be employed as fillers in soft and hard-filled gelatin capsules using lactose as well as high molecular weight polyethylene glycols and the like as excipients.

Liquid dosage forms for oral administration include pharmaceutically acceptable emulsions, solutions, suspensions, syrups and elixirs. In addition to the compound of the present invention or a composition thereof, the liquid dosage form may contain an inert diluent commonly used in the art, such as water or other solvents; solubilizers and emulsifiers such as ethanol, isopropyl alcohol, ethyl carbonate, ethyl acetate, benzyl alcohol, benzyl benzoate, propylene glycol, 1,3-butanediol, dimethylformamide; oils (such as cottonseed oil, groundnut oil, corn germ oil, olive oil, castor oil, sesame oil, etc.); glycerin; tetrahydrofurfuryl alcohol; fatty acid ester of polyethylene glycol and sorbitan; or a mixture thereof.

In addition to these inert diluents, the composition may also include excipients such as one or more of wetting agents, emulsifying agents, suspending agents, sweetening agents, flavoring agents, and flavoring agents.

In the case of a suspension, in addition to the compound or combination of the present invention, a carrier such as a suspending agent such as ethoxylated isostearyl alcohol, polyoxyethylene sorbitol, sorbitan ester, microcrystalline cellulose, boehmite, bentonite, agar and tragacanth, or a mixture thereof may be further contained.

The composition for rectal or vaginal administration preferably includes suppositories, which may be prepared by admixing the compound or combination of the present invention with a suitable non-irritating excipient or carrier, such as a cocoa butter, polyethylene glycol or suppository wax, which is solid at room temperature and liquid at body temperature, and thus can be melted in the rectum or vagina to release the active compound.

The dosage form of the compound of the present invention and the combination of the compound of the present invention and a medicament for blood cancer or inflammation may include ointments, powders, sprays, and inhalants. The medicament can be mixed under sterile conditions with a pharmaceutically acceptable excipient, diluent or carrier, and any preservative, buffer or propellant required. Ophthalmic formulations, ophthalmic ointments, powders and solutions are also intended to be encompassed within the scope of the present invention.

It is known that the compounds (or compositions) of the present invention can be placed in drinking water whereby a therapeutic dose of the compound is ingested along with the daily water supply. The compound can be metered directly into the drinking water, preferably in the form of a liquid water-soluble concentrate such as an aqueous solution of a water-soluble salt.

A paste formulation can be prepared by dispersing the medicament in a pharmaceutically acceptable oil such as peanut oil, sesame oil, corn oil or the like.

A pill containing an effective amount of a compound, pharmaceutical composition or combination of the present invention may be prepared by mixing a compound or composition of the present invention with a diluent such as a carbow wax, palm wax or the like. And a lubricant such as magnesium stearate or calcium stearate can be added to enhance the pelleting process.

Use

The compound represented by the formula (I) of the present invention, and the stereoisomer, pharmaceutically acceptable salt, prodrug, solvate, hydrate or crystal form thereof, is a selective inhibitor of bromodomain recognition protein and can inhibit the recognition effect of bromodomain recognition protein on lysine acetylation.

Accordingly, the present invention also provides use of the compound represented by the formula (I) of the present invention, and the stereoisomer, pharmaceutically acceptable salt, prodrug, solvate, hydrate or crystal form thereof as selective inhibitor of romodomain recognition protein, and use in the manufacture of a medicament for the treatment of a disease, condition and/or dysfunction mediated by a bromodomain recognition protein.

Preliminary studies indicate that the following diseases, disorders, and/or disorders are mediated by bromodomain recognition protein inhibitors: hematologic malignancy such as acute lymphoblastic leukemia, acute myeloid leukemia, B-cell chronic lymphocytic leukemia, chronic myelomonocytic leukemia, etc.; midline cancer; lung cancer; B cell lymphoma; prostate cancer; stomach cancer; colorectal cancer; kidney cancer; liver cancer; breast cancer; pancreatic cancer; immune diseases; cardiovascular diseases; and inflammation. However, related diseases mediated by bromodomain recognition proteins include, but are not limited to, hematological malignancy, midline cancer, inflammation and the like.

In another preferred embodiment, the compound represented by the formula (I) of the present invention, and the stereoisomer, pharmaceutically acceptable salt, prodrug, solvate, hydrate or crystal form thereof can be used in the manufacture of a medicament for the treatment of hematological malignancy, midline cancer, inflammation and the like, preferably in the manufacture of a medicament for the treatment of a disease including, but not limited to, hematologic malignancy such as acute lymphoblastic leukemia, acute myeloid leukemia, B-cell chronic lymphocytic leukemia, chronic myelomonocytic leukemia, etc.; midline cancer; lung cancer; B cell lymphoma; prostate cancer; stomach cancer; colorectal cancer; kidney cancer; liver cancer; breast cancer; pancreatic cancer; immune diseases; cardiovascular diseases; inflammation and the like.

Treatment Method

Accordingly, the present invention also provides a method of treating a disease, condition and/or dysfunction mediated by a bromodomain recognition protein inhibitor, comprising administering to a patient an effective amount of the compound of the formula (I), and a stereoisomer, pharmaceutically acceptable salt, prodrug, solvate, hydrate and crystal form thereof.

The above-mentioned features mentioned in the present invention, or the features mentioned in the examples, may be arbitrarily combined. All of the features disclosed in the present specification can be used in combination with any of the compositions, and the various features disclosed in the specification can be replaced by any alternative feature that provides the same, equal or similar purpose. Therefore, unless otherwise stated, the disclosed features are only general examples of equal or similar features.

The present invention is further illustrated below in conjunction with specific examples. It should be understood that the examples are only for illustrating the invention and not intended to limit the scope of the present invention. The experimental methods in the following examples which do not specify the specific conditions are usually carried out according to the conventional conditions such as those described in Sambrook et al., Molecular Cloning: Laboratory Manual (New York: Cold Spring Harbor Laboratory Press, 1989), or according to the conditions suggested by the manufacturer. Unless otherwise stated, percentages are by weight and parts by weight.

Starting materials can be obtained commercially, or by methods known in the art, or prepared according to the methods described herein.

The structure of the compound is determined by nuclear magnetic resonance ($^1$H-NMR) and/or mass spectrometry (MS). The NMR measurement was carried out by a Varian Mercury-400 nuclear magnetic resonance apparatus, and the solvent was deuterated chloroform ($CDCl_3$), deuterated methanol ($CD_3OD$), deuterated dimethyl sulfoxide ($DMSO\text{-}d_6$) or deuterated acetonitrile ($CD_3CN$), and TMS is an internal standard. The measurement of MS was carried out using a Thermo Finnigan LCQ-Deca XP type (ESI) liquid chromatography-mass spectrometer. The separation and purification of the product by the column chromatography was carried outby using an ISCO CombiFlash® Rf 75 rapid preparative chromatograph. The carrier was a 200-300 mesh silica gel from Qingdao Ocean Chemical Plant.

In the examples, the synthesis yield is a molar yield.

Example 1

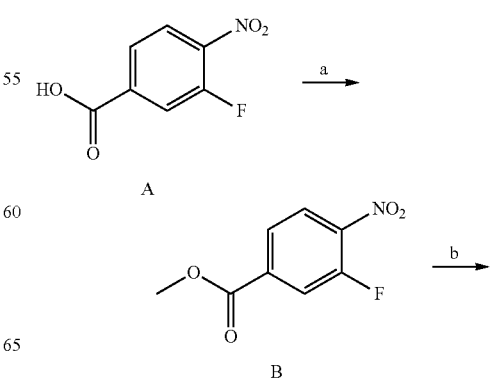

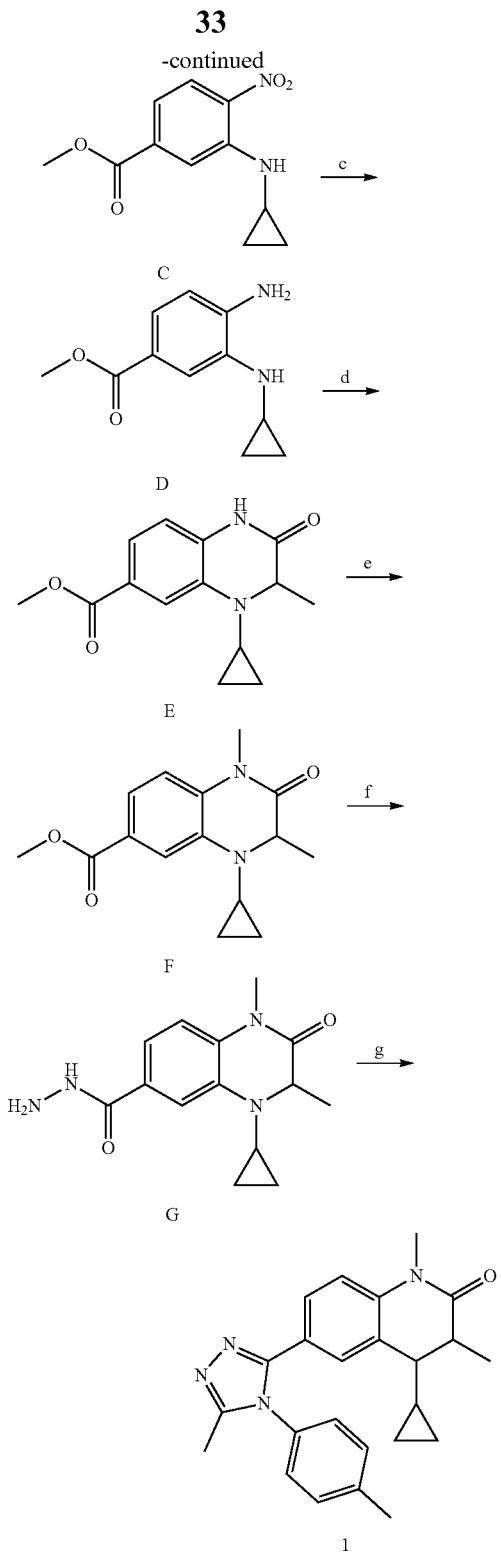

Reagents and conditions: a) thionyl chloride (SOCl₂), methanol, refluxed at 60° C. for 12 hours; b) cyclopropylamine, 1,2-dichloroethane, refluxed at 80° C. for 12 hours; c) iron powder, ammonium chloride solution, ethanol, reacted at 80° C. for 1 hour; d) 1.2-bromopropionyl bromide, N,N-diisopropylethylamine (DIPEA), dichloromethane, reacted at room temperature for 2 hours; 2. acetonitrile, DIPEA, reacted at 80° C. overnight; e) sodium hydride, N,N-dimethylformamide (DMF), methyl iodide, reacted at room temperature for 1 hour; f) hydrazine hydrate, ethanol, reacted at 80° C. for 24 hours; g) N-(p-tolyl)ethylthioamide, mercuric acetate, acetic acid, tetrahydrofuran (THF), reacted at 0° C. for 3 hours, room temperature for 24 hours.

a) Compound A (10 g, 54.02 mmol) was dissolved in EtOAc, cooled to 0° C., and SOCl₂ (8.24 mL, 113.45 mmol) was slowly added and refluxed at 60° C. for 12 h. The reaction was monitored with TLC. After the reaction was completed and the solvent was removed, the residue was cooled to 0° C., and the pH was adjusted to 7-8 with saturated NaHCO₃. Then the mixture was extracted with dichloromethane (40 mL*2) and 40 mL of water. The organic layers were combined and washed once with 80 mL of saturated brine. The organic phase was dried over anhydrous sodium sulfate, filtrated and dried to give 10.2 g of pale yellow solid B, yield 95%. MS(EI) [M]⁺: 199; ¹H NMR (400 MHz, CDCl₃) δ 8.11 (t, J=7.8 Hz, 1H), 7.97 (s, 1H), 7.94 (d, J=3.0 Hz, 1H), 3.98 (s, 3H).

b) Compound B (10 g, 50.25 mmol) was dissolved in 50 mL of 1,2-dichloroethane, cyclopropylamine (6.95 mL, 100.50 mmol) was added, then refluxed at 80° C. for 12 hours, and monitored by TLC plate. After the reaction was completed and the solvent was removed, the mixture was extracted with dichloromethane (40 mL*2) and 50 mL of water. The organic layers were combined and washed once with 100 mL of saturated brine. The organic phase was dried over anhydrous sodium sulfate and dried to give 10.2 g of red solid C, yield 86%. MS(EI)[M]⁺: 236; ¹H NMR (400 MHz, DMSO-d₆) δ 8.15 (d, J=8.8 Hz, 1H), 8.03 (s, 1H), 7.92 (d, J=1.7 Hz, 1H), 7.22 (dd, J=8.8, 1.8 Hz, 1H), 3.89 (s, 3H), 2.72-2.65 (m, 1H), 0.94-0.84 (m, 2H), 0.70-0.60 (m, 2H).

c) Compound C (10 g, 42.33 mmol) was dissolved in 30 mL of ethanol, ammonium chloride solution (11.33 g, 10 mL H₂O) was added, and then iron powder (11.86 g, 211.67 mmol) was added. The mixture was reacted at 80° C. for 1 hour, and monitored by TLC plate. After the reaction was completed, the iron powder was filtered off with celite, and the mixture was extracted with ethyl acetate (40 mL*2) and 40 mL of water. The organic layers were combined, washed with 80 mL of saturated brine, and dried over anhydrous sodium sulfate. The organica phase was dried by rotary evaporation to give 5.2 g of a yellow solid D, yield 60%. MS (ESI)[M+H]⁺: 207.67.

d) Compound D (5.2 g, 25.21 mmol) was dissolved in 20 mL anhydrous dichloromethane, cooled to 0° C., and DIPEA (8.78 mL, 50.42 mmol) and 2-bromopropionyl bromide (3.96 mL, 37.82 mmol) were added and then reacted at room temperature for 2 hr and monitored by TLC plate. After the reaction was completed, the mixture was extracted with dichloromethane (40 mL*2) and 40 mL of water. The organic layers were combined and washed once with 80 mL of saturated brine. The organic phase was dried over anhydrous sodium sulfate, filtrated and dried to give an intermediate. The intermediate was dissolved in 20 mL of acetonitrile, and then 9 mL of DIPEA was added, reacted at 80° C. overnight, and monitored by TLC plate. After the reaction was completed, the solvent was evaporated and the residue was extracted with dichloromethane (40 mL*2) and 40 mL of water. The organic layers were combined and washed with 80 mL of saturated brine. The organic phase was dried over anhydrous sodium sulfate, and the organic phase was purified by silica gel chromatography and eluted with gradient ethyl acetate/petroleum ether (0-40%) to give 3 g of white solid E, yield 46%. MS (ESI)[M+H]⁺: 261.20; ¹H NMR (400 MHz, CDCl₃) δ 8.61 (s, 1H), 7.75 (d, J=1.6 Hz, 1H), 7.53 (dd, J=8.1, 1.8 Hz, 1H), 6.78 (d, J=8.1 Hz, 1H), 4.09 (q, J=6.9 Hz, 1H), 3.90 (s, 3H), 2.54-2.45 (m, 1H), 1.24 (d, J=6.9 Hz, 3H), 1.09-1.02 (m, 1H), 0.87-0.78 (m, 1H), 0.69-0.60 (m, 1H), 0.60-0.52 (m, 1H).

e) Compound E (3 g, 11.53 mmol) was dissolved in 8 mL of DMF, cooled to 0° C., sodium hydride (0.83 g, 34.58 mmol) was added, and the mixture was reacted at 0° C. for half an hour and then iodomethane (1.08 mL, 17.30 mmol) was added. Then, the mixture was reacted at room temperature for 1 hour, and monitored by TLC plate. After the reaction was completed, the mixture was cooled to 0° C., adjusted to pH 7-8 with dilute hydrochloric acid, and then extracted with dichloromethane (20 mL*2) and 40 mL of water. The organic layers were combined and washed once with 40 mL of saturated brine. The organic phase was dried over anhydrous sodium sulfate, and the organic phase was purified by silica gel chromatography and eluted with gradient ethyl acetate/petroleum ether (0 to 25%) to give 2.8 g of colorless transparent liquid F, yield 89%. MS (ESI)[M+H]$^+$: 275.18; $^1$H NMR (400 MHz, CDCl$_3$) δ 7.75 (d, J=1.9 Hz, 1H), 7.59 (dd, J=8.3, 1.9 Hz, 1H), 6.93 (d, J=8.4 Hz, 1H), 4.12 (q, J=6.9 Hz, 1H), 3.89 (s, 3H), 3.35 (s, 3H), 2.48-2.42 (m, 1H), 1.15 (d, J=6.9 Hz, 3H), 1.07-0.99 (m, 1H), 0.84-0.76 (m, 1H), 0.66-0.58 (m, 1H), 0.56-0.48 (m, 1H).

f) Compound F (2.8 g, 10.21 mmol) was dissolved in 20 mL of ethanol, hydrazine hydrate (2.48 mL, 51.05 mmol) was added, then reacted at 80° C. for 24 hours, and monitored by TLC plate. The solvent was evaporated and the water was removed several times with toluene and then the residue was dried to give 2.5 g of white foamy solid G, yield 89%.

g) Compound G (0.6 g, 2.19 mmol) was dissolved in 3 mL of THF and 4.2 mL of acetic acid. N-(p-tolyl)ethylthioamide (0.36 g, 2.19 mmol) was added and cooled to 0° C. Mercury acetate (1.05 g, 3.29 mmol) was added, and the reaction was carried out at 0° C. for 3 hours, then at room temperature for 24 hours, and monitored by TLC plate. After the reaction was completed, the pH was neutralized with saturated sodium bicarbonate to 7-8, then the mixture was extracted with ethyl acetate (20 mL*2) and 20 mL of water. The organic layers were combined, washed once with 40 mL of saturated brine. The organic phase was dried over anhydrous sodium sulfate, purified by silica gel column chromatography and eluted with gradient methanol/dichloromethane (0~10%) to give 300 mg of white powder compound 1 in a yield of 35%. MS (ESI)[M+H]$^+$: 388.41; $^1$H NMR (400 MHz, CDCl$_3$) δ 7.30 (d, J=8.0 Hz, 2H), 7.15 (d, J=1.9 Hz, 1H), 7.09 (d, J=8.3 Hz, 2H), 6.98 (dd, J=8.3, 1.9 Hz, 1H), 6.81 (d, J=8.4 Hz, 1H), 4.04 (q, J=6.8 Hz, 1H), 3.29 (s, 3H), 2.43 (s, 3H), 2.34 (s, 3H), 2.20-2.15 (m, 1H), 1.09 (d, J=6.8 Hz, 3H), 0.73-0.65 (m, 1H), 0.64-0.56 (m, 1H), 0.55-0.48 (m, 1H), 0.23-0.14 (m, 1H).

Example 2

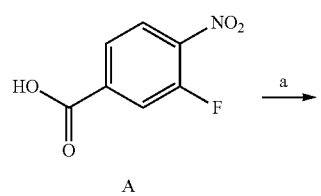

A

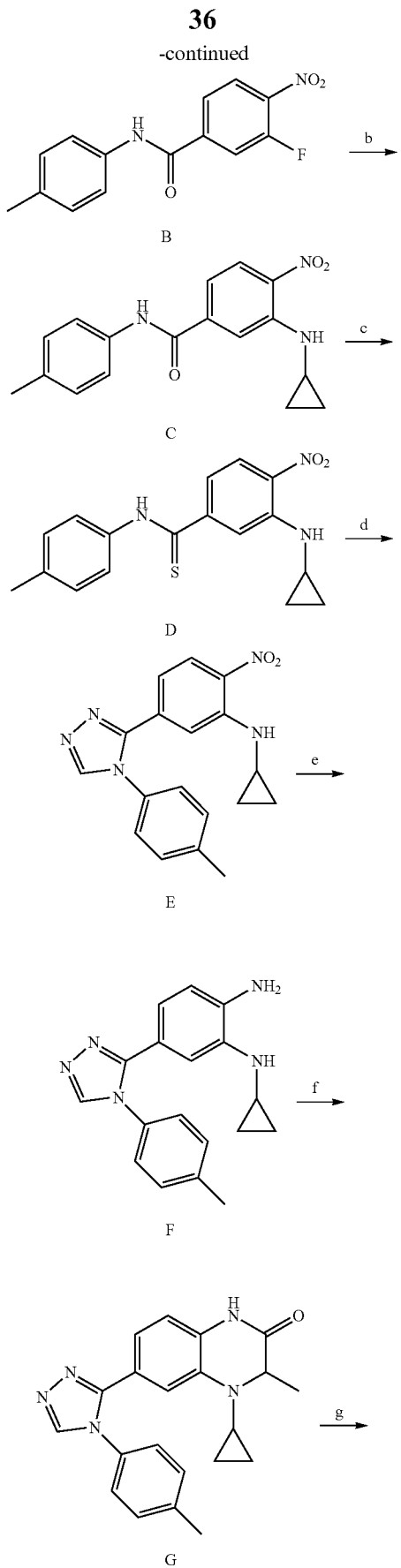

-continued

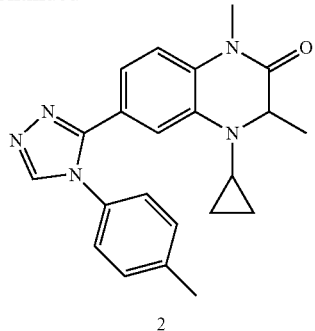

2

Reagents and conditions: a) p-methylaniline, 2-(7-oxobenzotriazole)-N,N,N',N'-tetramethyluronium hexafluorophosphate (HATU), DIPEA, DMF, reacted overnight at room temperature; b) cyclopropylamine, 1,2-dichloroethane, refluxed at 80° C. for 12 hours; c) Lawesson reagent, toluene, refluxed at 110° C. overnight; d) 1. hydrazine hydrate, reacted at room temperature for 4 hours; 2. trimethyl orthoformate, DMF, acetic acid, reacted overnight at room temperature; e) tin dichloride dihydrate, concentrated hydrochloric acid, reacted at room temperature for 3 hours; f) 1.2-bromopropionyl bromide, DIPEA, dichloromethane, reacted at room temperature for 2 hours; 2. acetonitrile, DIPEA, reacted at 80° C. overnight; g) sodium hydride, N,N-dimethylformamide (DMF), iodomethane, reacted at room temperature for 1 hour.

a) Compound A (2 g, 10.80 mmol) was dissolved in 10 mL DMF, HATU (4.11 g, 10.80 mmol) was added and reacted at room temperature for half an hour, then p-methylaniline (1.16 g, 10.80 mmol) and DIPEA (1.88 mL, 10.80) were added. The mixture was reacted at room temperature overnight, and monitored with TLC plate. After the reaction was completed, the mixture was extracted with ethyl acetate (20 mL*2) and 60 mL of saturated sodium bicarbonate. The organic layers were combined and washed with 40 mL of diluted hydrochloric acid and 40 mL of saturated brine. The organic phase was dried over anhydrous sodium sulfate to give 2.2 g of a yellow solid B, yield 74%. $^1$H NMR (400 MHz, DMSO-$d_6$) δ 10.49 (s, 1H), 8.31 (t, J=8.1 Hz, 1H), 8.10 (d, J=12.0 Hz, 1H), 7.96 (d, J=8.5 Hz, 1H), 7.65 (d, J=8.4 Hz, 2H), 7.19 (d, J=8.3 Hz, 2H), 2.29 (s, 3H).

b) Compound B (2 g, 7.29 mmol) was dissolved in 10 mL of 1,2-dichloroethane, and cyclopropylamine (1.01 mL, 14.58 mmol) was added, then refluxed at 80° C. for 12 hours. The reaction was monitored by TLC plate. After the reaction was completed, the solvent was removed and the residue was extracted with dichloromethane (20 mL*2) and 20 mL of water. The organic layers were combined and washed with 40 mL of saturated brine. The organic phase was dried over anhydrous sodium sulfate and then dried by rotary evaporation to give 2.1 g of a red solid C, yield 93%. $^1$H NMR (400 MHz, CDCl$_3$) δ 8.23 (d, J=8.8 Hz, 1H), 8.12 (s, 1H), 7.86 (s, 1H), 7.80 (s, 1H), 7.53 (d, J=8.1 Hz, 2H), 7.19 (d, J=8.3 Hz, 2H), 7.01 (d, J=8.7 Hz, 1H), 2.69-2.62 (m, 1H), 2.35 (s, 3H), 1.00-0.94 (m, 2H), 0.71-0.66 (m, 2H).

c) Compound C (2 g, 6.42 mmol) was dissolved in 10 mL of toluene, and Lawesson reagent (1.36 g, 3.37 mmol) was added, then refluxed at 110° C. overnight, and the reaction was monitored by TLC plate. After the reaction was completed, the solvent was evaporated and the residue was dissolved in 50 ml of methyl chloride. The mixture was purified by silica gel column chromatography and eluted with gradient ethyl acetate/petroleum ether (0 to 15%) to give 1.8 g of red solid D, yield 86%. MS (ESI) [M+H]$^+$: 328.11; $^1$H NMR (400 MHz, DMSO-$d_6$) δ 11.97 (s, 1H), 8.12 (d, J=8.8 Hz, 2H), 7.73 (d, J=8.2 Hz, 2H), 7.65 (s, 1H), 7.26 (d, J=8.2 Hz, 2H), 7.07 (d, J=8.8 Hz, 1H), 2.71 (s, 1H), 2.33 (s, 3H), 0.89 (d, J=5.0 Hz, 2H), 0.68 (s, 2H).

d) Compound D (1.8 g, 5.50 mmol) was dissolved in a mixed solvent of 5 mL methanol and 20 mL of THF, and hydrazine hydrate (2.67 mL, 55.05 mmol) was added, and then reacted at room temperature for 4 hours, monitored by TLC plate. After the reaction was completed, the solvent was evaporated to give an intermediate. The intermediate was dissolved in 5 mL of DMF, and 4 mL of acetic acid and trimethyl orthoformate (1.62 mL, 14.85 mmol) were added, and then reacted at room temperature overnight, and monitored by TLC plate. After the reaction was completed, the pH was adjusted with saturated NaHCO$_3$ to 7-8, and the mixture was extracted with ethyl acetate (40 mL*2) and 80 mL of saturated sodium bicarbonate. The organic layers were combined and wash once with 80 mL of saturated brine. The organic phase was purified by silica gel column chromatography and eluted with gradient ethyl acetate/petroleum ether (0 to 30%) to give 1.5 g of red solid E, yield 81%. $^1$H NMR (400 MHz, CDCl$_3$) δ 8.34 (s, 1H), 8.10 (d, J=8.8 Hz, 1H), 8.03 (s, 1H), 7.45 (s, 1H), 7.31 (d, J=7.9 Hz, 2H), 7.17 (d, J=8.2 Hz, 2H), 6.81 (d, J=8.8 Hz, 1H), 2.44 (s, 3H), 2.36-2.29 (m, 1H), 0.74-0.68 (m, 2H), 0.51-0.46 (m, 2H).

e) Compound E (1.5 g, 4.47 mmol) was dissolved in 4 mL of concentrated hydrochloric acid, and a solution of tin dichloride dihydrate (5.04 g, 22.35 mmol) in concentrated hydrochloric acid (4 mL) was added and then reacted at room temperature for 3 hours and monitored by TLC. After the reaction was completed, the solvent was evaporated, and then the mixture was adjusted to pH 7-8 with saturated sodium bicarbonate, and then extracted with ethyl acetate (20 mL*2) and 20 mL of water. The organic layers were combined and washed once with 40 mL of saturated brine. After dried over anhydrous sodium sulfate, the organic layer was dried by rotary evaporation to give 1.2 g of a yellow foamy powder F, yield 88%.

f) Compound F (1.2 g, 3.93 mmol) was dissolved in 8 mL of dry dichloromethane and cooled to 0° C., and DIPEA (1.37 mL, 7.86 mmol) and 2-bromopropionyl bromide (0.62 mL, 5.90 mmol) were added, then reacted at room temperature for 2 h. The mixture was monitored by TLC plate. After the reaction was completed, the mixture was extracted with dichloromethane (20 mL*2) and 20 mL of water. The organic layers were combined, washed once with 40 mL of saturated brine, dried over anhydrous sodium sulfate, filtrated and dried by rotary evaporation to give 0.7 g of the red oily intermediate. The intermediate was dissolved in 5 mL of acetonitrile, and then 2 mL of DIPEA was added and reacted at 80° C. overnight. The reaction was monitored by TLC plate. After the reaction was completed, the solvent was evaporated and the residue was extracted with dichloromethane (20 mL*2) and 20 mL of water. The organic layers were combined, and washed once with 40 mL of saturated brine. The organic phase was dried over anhydrous sodium sulfate, purified by silica gel column chromatography and eluted with gradient ethyl acetate/petroleum ether (0 to 20%) to give 0.8 g of pale yellow powder G in a yield of 57%.

g) Compound G (0.8 g, 2.23 mmol) was dissolved in 2 mL DMF, cooled to 0° C., sodium hydride (0.16 g, 6.69 mmol) was added, and reacted at 0° C. for half an hour, and methyl iodide (0.21 mL, 3.35 mmol) was added at 0° C., then reacted for 1 hour at room temperature. The reaction was monitored with TLC plate. After the reaction was completed, the mixture was neutralized with saturated sodium bicarbonate to pH 7-8, and then extracted with ethyl acetate (20 mL*2) and 40 mL of water. The organic layers were combined, washed once with 40 mL of saturated brine, dried over anhydrous sodium sulfate, and the organic phase was purified by silica gel column chromatography and eluted with gradient methanol/dichloromethane (0 to 10%) to give 0.22 g of compound 2 as pale yellow powder in a yield of 26%. MS(ESI)[M+H]$^+$: 374.31; $^1$H NMR (400 MHz, CDCl$_3$) δ 8.28 (s, 1H), 7.29-7.24 (m, 2H), 7.17-7.14 (m, 2H), 7.14-7.12 (m, 1H), 7.04 (dd, J=8.3, 1.9 Hz, 1H), 6.85 (d, J=8.3 Hz, 1H), 4.05 (q, J=6.9 Hz, 1H), 3.31 (s, 3H), 2.42 (s, 3H), 2.22-2.14 (m, 1H), 1.10 (d, J=6.8 Hz, 3H), 0.72-0.64 (m, 1H), 0.58-0.47 (m, 2H), 0.21-0.13 (m, 1H).

Example 3

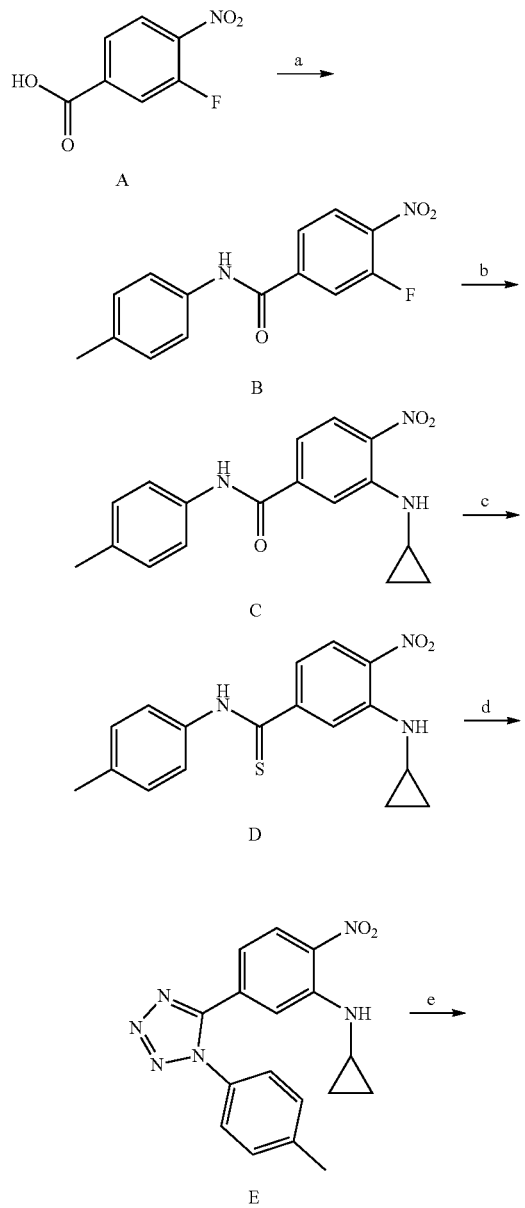

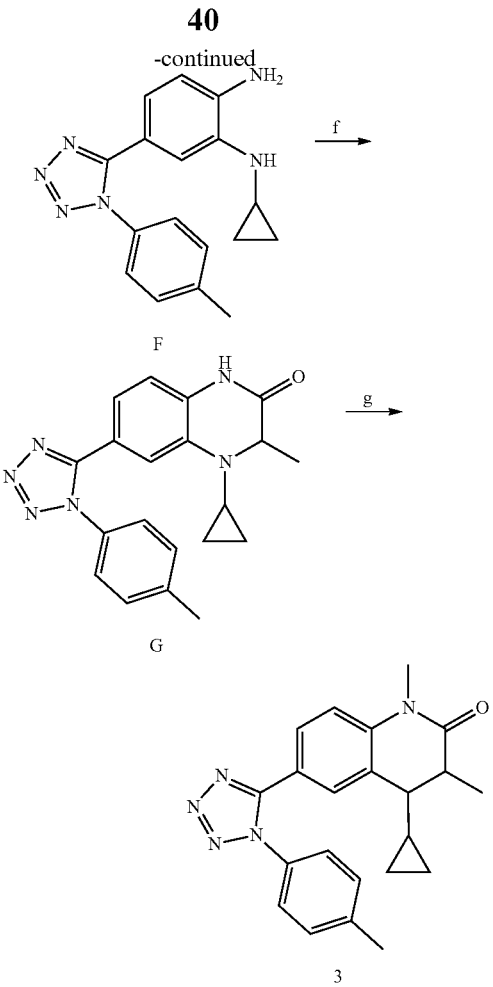

Reagents and conditions: a) p-methylaniline, 2-(7-oxobenzotriazole)-N,N,N',N'-tetramethyluronium hexafluorophosphate (HATU), DIPEA, DMF, reacted overnight at room temperature; b) cyclopropylamine, 1,2-dichloroethane, refluxed at 80° C. for 12 hours; c) Lawson's reagent, toluene, refluxed at 110° C. overnight; d) tetrahydrofuran, mercury acetate, trimethylsilyl azide, reacted at 0° C. for 4 hours; e) tin dichloride dihydrate, concentrated hydrochloric acid, reacted at room temperature for 3 hours; f) 1. 2-bromopropionyl bromide, DIPEA, dichloromethane, reacted at room temperature for 2 hours; 2. acetonitrile, DIPEA, reacted at 80° C. overnight; g) sodium hydride, N,N-dimethylformamide (DMF), iodomethane, reacted at room temperature for 1 hour.

Compound D was prepared by referring to the steps a-c in the preparation method of Compound 2.

d) Compound D (2 g, 6.12 mmol) was dissolved in 10 mL of tetrahydrofuran, cooled to 0° C., mercury acetate (3.88 g, 12.24 mmol) and trimethylsilyl azide (8.05 mL, 61.2 mmol) were added and reacted at 0° C. for 4 hours. The reaction was monitored by TLC plate. After the reaction was completed, the solvent was evaporated and the residue was extracted with ethyl acetate (30 mL*2) and 30 mL of water. The combined organic phase was purified by silica gel column chromatography and eluted with ethyl acetate/petroleum ether (0 to 10%) to afford 1.8 g of red solid E in a yield of 87%. MS(ESI)[M+H]$^+$: 337.09; $^1$H NMR (400 MHz, CDCl$_3$) δ 8.14 (d, J=8.9 Hz, 1H), 8.03 (s, 1H), 7.53 (d, J=1.8 Hz, 1H), 7.35 (d, J=8.2 Hz, 2H), 7.32-7.27 (m, 2H), 6.86 (dd, J=8.9, 1.9 Hz, 1H), 2.46 (s, 3H), 2.39-2.31 (m, 1H), 0.76-0.68 (m, 2H), 0.55-0.44 (m, 2H).

e) Compound E (1.8 g, 5.35 mmol) was dissolved in 4 mL of concentrated hydrochloric acid, and a solution of tin dichloride dihydrate (6.04 g, 26.75 mmol) in concentrated hydrochloric acid (4 mL) was added, and then reacted at room temperature for 3 hours. The reaction was monitored by TLC plate. After the reaction was completed, the pH was adjusted to 7-8 with saturated sodium bicarbonate, and then the mixture was extracted with ethyl acetate (20 mL*2) and 20 mL of water. The organic layers were combined, washed with 40 mL of saturated brine, and dried over anhydrous sodium sulfate. The organic phase was dried by rotary evaporation to give 1.6 g of yellow foamy powder F, yield 93%.

f) Compound F (1.5 g, 4.90 mmol) was dissolved in 8 mL dichloromethane, cooled to 0° C., DIPEA (1.71 mL, 9.80 mmol) and 2-bromopropionyl bromide (0.77 mL, 7.35 mmol) were added and reacted at room temperature for 2 hours. The reaction was monitored by TLC plate. After the reaction was completed, the mixture was extracted with dichloromethane (20 mL*2) and 20 mL of water. The organic layers were combined, washed with 40 mL of saturated brine, dried over anhydrous sodium sulfate, filtrated and dried by rotary evaporation to obtain 0.8 g of a red oily intermediate. It was then dissolved in 5 mL of acetonitrile, 2 mL of DIPEA was added, and then reacted at 80° C. overnight, and the reaction was monitored by TLC plate. After the reaction was completed, the solvent was evaporated and the residue was extracted with dichloromethane (20 mL*2) and 20 mL of water. The combined organic layer was washed with 40 mL of saturated brine, and the organic phase was dried over anhydrous sodium sulfate, and purified by silica gel column chromatography and eluted with gradient ethyl acetate/petroleum ether (0 to 20%) to obtain 1.0 g of pale yellow powder G in a yield of 57%. MS(ESI)[M+H]$^+$: 361.11; $^1$H NMR (400 MHz, CDCl$_3$) δ 9.62 (s, 1H), 7.33-7.28 (m, 4H), 7.23 (d, J=1.8 Hz, 1H), 7.02 (dd, J=8.1, 1.8 Hz, 1H), 6.82 (d, J=8.1 Hz, 1H), 4.02 (q, J=6.8 Hz, 1H), 2.44 (s, 3H), 2.27-2.22 (m, 1H), 1.20 (d, J=6.9 Hz, 3H), 0.84-0.80 (m, 1H), 0.76-0.68 (m, 1H), 0.56-0.53 (m, 1H), 0.26-0.20 (m, 1H).

g) Compound G (0.6 g, 1.67 mmol) was dissolved in 2 mL DMF, cooled to 0° C., sodium hydride (0.12 g, 5.01 mmol) was added, and reacted at 0° C. for half an hour, and then iodomethane (0.19 mL, 3.01 mmol) was added at 0° C. and reacted at room temperature for 1 h. The reaction was monitored by TLC plate. After the reaction was completed, the mixture was neutralized the pH to 7-8 with saturated sodium bicarbonate, extracted with ethyl acetate (20 mL*2) and 40 mL of water. The organic layers were combined, washed with 40 mL of saturated brine, and dried over anhydrous sodium sulfate. The organic phase was purified by silica gel column chromatography and eluted with gradient methanol/dichloromethane (0 to 10%) to give 180 mg of pale yellow powder compound 3, yield 29%. MS(ESI)[M+H]$^+$: 375.20; $^1$H NMR (400 MHz, CDCl$_3$) δ 7.36-7.28 (m, 4H), 7.23 (d, J=1.7 Hz, 1H), 7.15 (dd, J=8.3, 1.8 Hz, 1H), 6.91 (d, J=8.3 Hz, 1H), 4.08 (q, J=6.9 Hz, 1H), 3.33 (s, 3H), 2.45 (s, 3H), 2.25-2.15 (m, 1H), 1.13 (d, J=6.8 Hz, 3H), 0.76-0.65 (m, 1H), 0.58-0.48 (m, 2H), 0.26-0.15 (m, 1H).

Example 4

Compound 4 was prepared in the same manner as in example 3 except that cyclopropylamine was replaced by cyclopentylamine in step b.

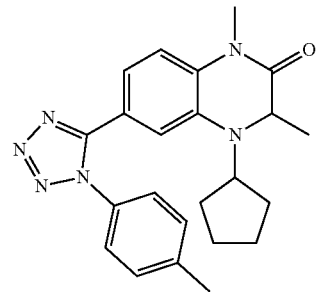

MS(ESI)[M+H]$^+$: 403.13. $^1$H NMR (400 MHz, CDCl$_3$) δ 7.30 (q, J=8.4 Hz, 4H), 7.13 (d, J=8.3 Hz, 1H), 6.93 (d, J=8.1 Hz, 2H), 4.15 (q, J=6.7 Hz, 1H), 3.48 (dd, J=14.9, 7.4 Hz, 1H), 3.34 (s, 3H), 2.43 (s, 3H), 1.83 (dd, J=14.2, 8.8 Hz, 2H), 1.74-1.66 (m, 1H), 1.64-1.48 (m, 5H), 0.99 (d, J=6.8 Hz, 3H).

Example 5

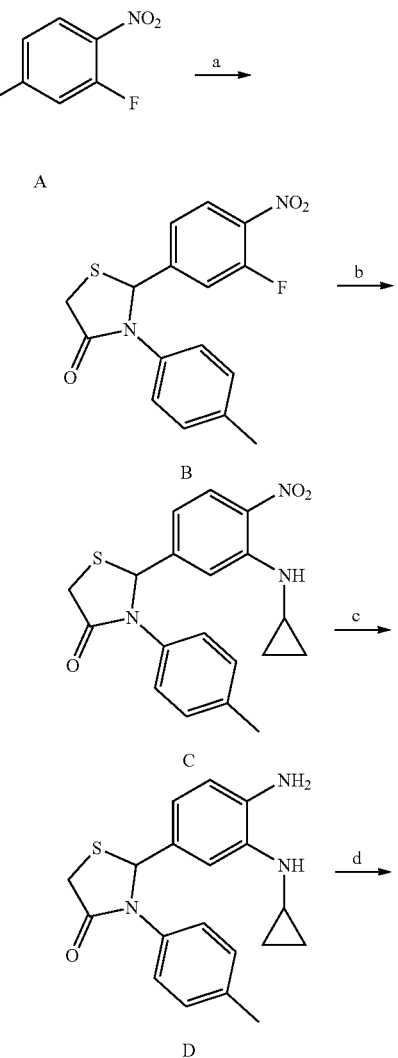

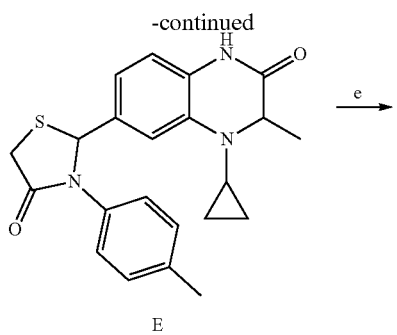

E

[Structure 5]

Reagents and conditions: a) p-toluidine, thioglycolic acid, dicyclohexylcarbodiimide, tetrahydrofuran, 0° C.—room temperature, 12 hours; b) cyclopropylamine, 1,2-dichloroethane, refluxed at 80° C. for 12 hours; c) tin dichloride dihydrate, concentrated hydrochloric acid, 0° C.—room temperature, 3 hours; d) 1. 2-bromopropionyl bromide, N,N-diisopropylethylamine (DIPEA), dichloromethane, reacted at room temperature for 2 hours; 2. acetonitrile, DIPEA, reacted at 80° C. overnight; e) sodium hydride, N,N-dimethylformamide (DMF), iodomethane, and reacted at room temperature for 1 hour.

a) p-Toluidine (2 g, 18.69 mmol) and compound A (6.3 g, 37.38 mmol) were dissolved in dry tetrahydrofuran at 0° C., stirred at 0° C. for 10 min, then thioglycolic acid (3.9 mL, 56.07) was added and stirred at 0° C. for another 10 min. Then dicyclohexylcarbodiimide (4.62 g, 22.43 mmol) was added and then stirred at room temperature overnight. The reaction was monitored by TLC plate. After the reaction was completed, the mixture was filtrated and the filtrate was purified by silica gel column chromatography and eluted with gradient ethyl acetate/petroleum ether (0-10%) to give 3.5 g of pale yellow solid B, yield 56%. $^1$H NMR (400 MHz, DMSO-$d_6$) δ 8.06 (t, J=8.1 Hz, 1H), 7.70 (d, J=12.0 Hz, 1H), 7.47 (d, J=8.5 Hz, 1H), 7.24 (d, J=8.2 Hz, 2H), 7.12 (d, J=8.2 Hz, 2H), 6.61 (s, 1H), 4.11 (d, J=15.6 Hz, 1H), 3.89 (d, J=15.6 Hz, 1H), 2.21 (s, 3H).

b) Compound B (2 g, 6.02 mmol) was dissolved in 10 mL of 1,2-dichloroethane, then cyclopropylamine (0.83 mL, 12.04 mmol) was added, then reacted at 80° C. overnight. The reaction was monitored by TLC plate. After the reaction was completed, the solvent was evaporated, and the residue was extracted with dichloromethane (20 mL*2) and 30 mL of water. The organic layers were combined, washed once with 40 mL of saturated brine. The organic phase was dried over anhydrous sodium sulfate, and purified by silica gel column chromatography and eluted with gradient ethyl acetate/petroleum ether (0 to 15%) to give 1.8 g of a red solid C, yield 81%. $^1$H NMR (400 MHz, CDCl$_3$) δ 8.11 (d, J=8.9 Hz, 1H), 8.07 (s, 1H), 7.13-7.11 (m, 4H), 6.66 (dd, J=8.9, 1.9 Hz, 1H), 6.05 (d, J=1.0 Hz, 1H), 3.99 (dd, J=15.8, 1.6 Hz, 1H), 3.87 (d, J=15.8 Hz, 1H), 2.54-2.47 (m, 1H), 2.28 (s, 3H), 0.92-0.84 (m, 2H), 0.60-0.54 (m, 2H).

c) Compound C (1.5 g, 4.06 mmol) was dissolved in 4 mL of concentrated hydrochloric acid, cooled to 0° C., and a solution of tin dichloride dichloride (4.35 g, 19.29 mmol) in concentrated hydrochloric acid (4 mL) was added and then reacted at room temperature for 4 h. The reaction was monitored by TLC plate. After the reaction was completed, the mixture was neutralized the pH to 7-8 with 6 N NaOH, then extracted with ethyl acetate (40 mL*2) and 20 mL of water. The organic layers were combined, washed once with 40 mL of saturated brine. The organic phase was dried over anhydrous sodium sulfate and dried by rotary evaporation to give 1.1 g of pale yellow powder D, yield 80%.

d) Compound D (1.1 g, 3.24 mmol) was dissolved in 8 mL dry dichloromethane, cooled to 0° C., DIPEA (1.13 mL, 6.48 mmol) and 2-bromopropionyl bromide (0.41 mL, 3.89 mmol) were added and then reacted at room temperature for 2 h. The reaction was monitored by TLC plate. After the reaction was completed, the mixture was extracted with dichloromethane (20 mL*2) and 20 mL of water. The organic layers were combined and washed once with 40 mL of saturated brine. The organic phase was dried over anhydrous sodium sulfate, purified by silica gel column chromatography and eluted with gradient ethyl acetate/petroleum ether (0-30%) to give 200 mg of yellow solid intermediate. $^1$H NMR (400 MHz, CDCl$_3$) δ 7.78 (s, 1H), 7.18 (d, J=8.0 Hz, 1H), 7.06 (s, 4H), 7.03 (d, J=1.9 Hz, 1H), 6.70 (dd, J=8.1, 2.0 Hz, 1H), 6.04 (s, 1H), 4.56-4.47 (m, 1H), 3.96 (dd, J=15.8, 1.6 Hz, 1H), 3.84 (d, J=15.8 Hz, 1H), 2.42-2.34 (m, 1H), 2.24 (s, 3H), 1.88 (d, J=7.0 Hz, 3H), 0.80-0.70 (m, 2H), 0.47-0.38 (m, 2H). The intermediate was dissolved in 5 mL acetonitrile, 1 mL DIPEA was added and then reacted at 80° C. overnight. The reaction was monitored by TLC plate. After the reaction was completed, the solvent was evaporated and the residue was extracted with dichloromethane (20 mL*2) and 20 mL of water. The organic layers were combined, and washed once with 40 mL of saturated brine. The organic phase was dried over anhydrous sodium sulfate and directly dried by rotary evaporation without purification to give 0.1 g of white solid E, yield 8%.

e) Compound E (0.1 g, 0.25 mmol) was dissolved in 2 mL DMF, cooled to 0° C., sodium hydride (0.02 g, 0.76 mmol) was added and reacted at 0° C. for half an hour, then iodomethane (0.03 mL, 0.51 mmol) was added at 0° C. and then reacted at room temperature for 1 h. The reaction was monitored by TLC plate. After the reaction was completed, the mixture was neutralized the pH to 7-8 with saturated sodium bicarbonate, extracted with ethyl acetate (20 mL*2) and 40 mL of water. The organic layers were combined, washed once with 40 mL of saturated brine. The organic phase was dried over anhydrous sodium sulfate, purified by silica gel column chromatography, and eluted with gradient ethyl acetate/petroleum ether (0-30%) to give 15 mg white powder compound 5, yield 15%. MS (ESI) [M+H]$^+$: 408.21; $^1$H NMR (400 MHz, CDCl$_3$) δ 7.11-7.04 (m, 3H), 7.02 (s, 1H), 7.01-6.97 (m, 1H), 6.86-6.79 (m, 1H), 6.78-6.75 (m, 1H), 6.04 (d, J=34.1 Hz, 1H), 4.06 (q, J=6.9 Hz, 1H), 3.96 (dd, J=15.8, 9.5 Hz, 1H), 3.87 (d, J=15.8 Hz, 1H), 3.27 (d, J=4.1 Hz, 3H), 2.38-2.30 (m, 1H), 2.25 (d, J=3.0 Hz, 3H), 1.11 (dd, J=8.7, 7.1 Hz, 3H), 0.94-0.85 (m, 1H), 0.82-0.71 (m, 1H), 0.63-0.54 (m, 1H), 0.41-0.29 (m, 1H).

Example 6

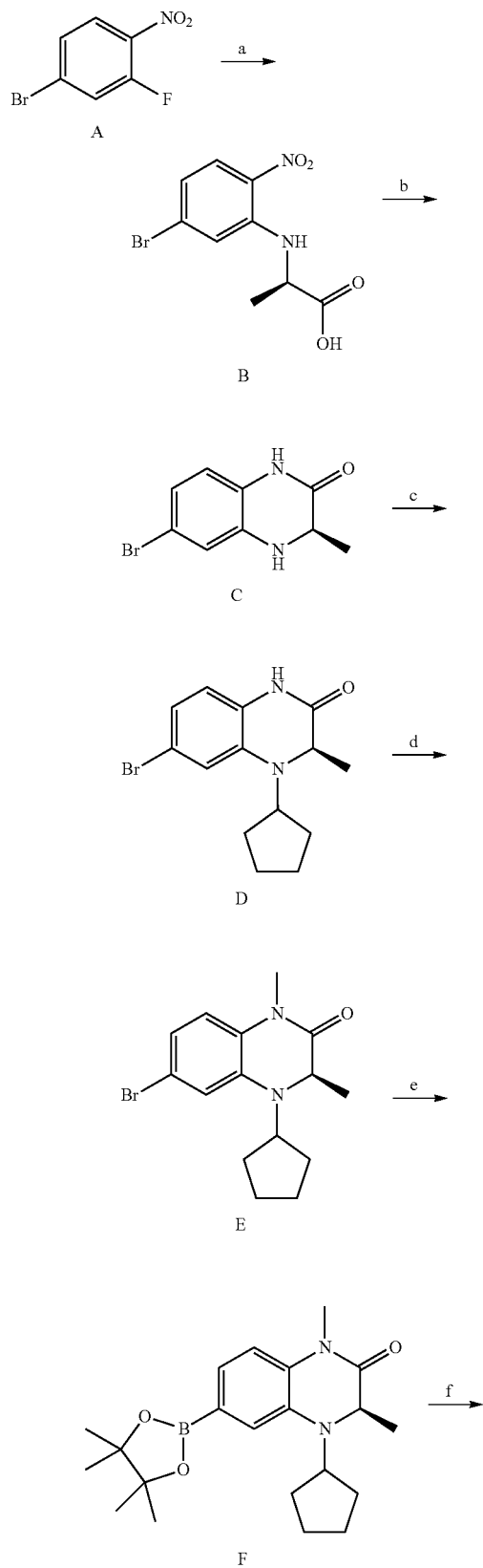

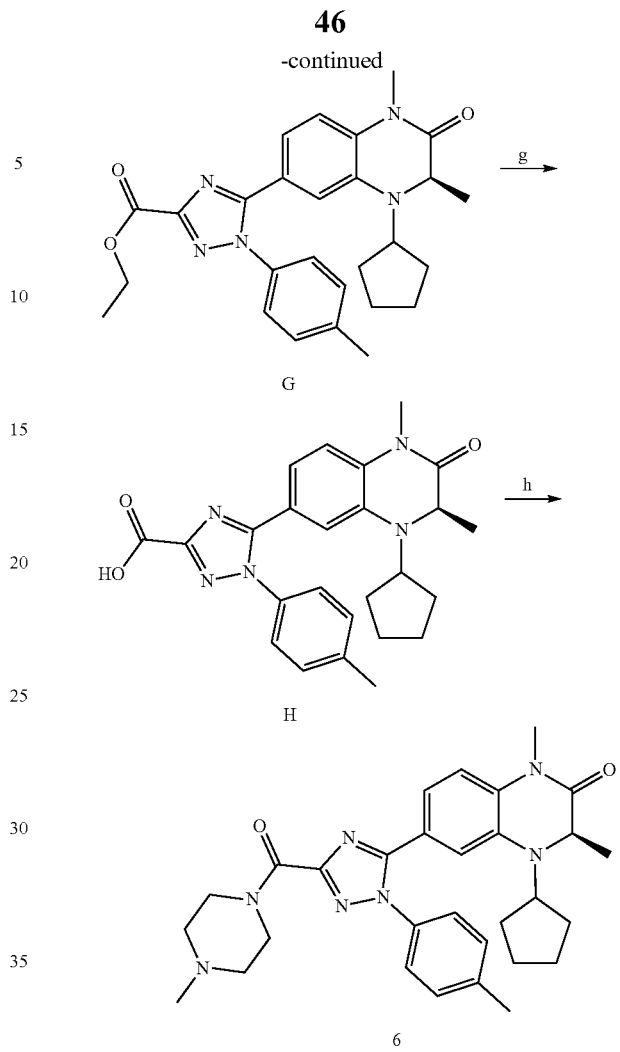

Reagents and conditions: a) D-aminopropionic acid, potassium carbonate, ethanol, water, 80° C., 8 hours; b) potassium carbonate, sodium dithionite, water, reacted at 60° C. overnight; c) phenylsilane, cyclopentanone, tin dibutyl dichloride, THF, room temperature, 10 hours; d) NaH, DMF, iodomethane, 0° C.—room temperature, 4 hours; e) bis(pinacolato)diboron, potassium acetate, dioxane, [1,1'-bis(diphenylphosphino)ferrocene]palladium dichloride dichloromethane complex, refluxed at 120° C. overnight; f) 5-bromo-1-(p-tolyl)-1H-1,2,4-triazole-3-carboxylate, sodium bicarbonate, THF, [1,1'-bis(diphenylphosphino)ferrocene]palladium dichloride dichloromethane complex, refluxed at 80° C. overnight; g) lithium hydroxide, THF, $H_2O$, room temperature, 12 hours; h) HATU, DMF, N-methylpiperazine, DIPEA, reacted at room temperature overnight.

a) 4-bromo-2-fluoronitrobenzene (25 g, 113.64 mmol), D-aminopropionic acid (11.12 g, 125.0 mmol) and potassium carbonate (17.25 g, 125.0 mmol) were dissolved in 500 mL mixed solvent of ethanol and water (3:1). The mixture was heated under reflux for 8 hours. The reaction was monitored by TLC plate. After the reaction was completed, the mixture was cooled to room temperature, the pH was adjusted to 2-3 with 1N HCl, and the solid was filtered, washed with 200 mL of petroleum ether, filtered and dried by rotary evaporation to give 28.7 g of a yellow solid B in a yield of 88%. $^1$H NMR (400 MHz, $CDCl_3$) δ 8.35 (d, J=6.9

Hz, 1H), 8.06 (d, J=9.1 Hz, 1H), 6.90 (s, 1H), 6.85 (d, J=9.2 Hz, 1H), 4.33 (p, J=7.0 Hz, 1H), 1.67 (d, J=7.0 Hz, 3H).

b) B (28.7 g, 99.31 mmol) and $K_2CO_3$ (27.41 g, 198.22 mmol) were dissolved in 500 mL water, and sodium dithionite (86.45 g, 496.55 mmol) was added portionwise and allowed to react overnight at 60° C. and then a large amount of precipitate was produced. The reaction was monitored by TLC plate. After the reaction was completed, the solid was filtered, washed with 300 mL of water and dried to give 9 g of a yellow solid C, yield 38%. $^1$H NMR (400 MHz, $CDCl_3$) δ 9.42 (s, 1H), 6.89-6.83 (dd, J=8.2, 2.0 Hz, 1H), 6.81 (s, 1H), 6.68-6.59 (dd, J=13.1, 7.6 Hz, 1H), 4.02 (q, J=6.7 Hz, 1H), 3.92 (s, 1H), 1.45 (d, J=6.7 Hz, 3H).

c) C (9 g, 37.34 mmol), phenylsilane (11.90 g, 113.14 mmol), cyclopentanone (10.0 mL, 113.14 mmol) and tin dibutyl dichloride (17.02 g, 56.01 mmol) were dissolved in 100 mL THF. The mixture was stirred at room temperature for 10 hours and the reaction was monitored by TLC plate. After the reaction was completed, the solvent was evaporated, and the organic phase was purified by silica gel chromatography and eluted with gradient ethyl acetate/petroleum ether (0-30%) to give 10.4 g of brown oil D, yield 90%. MS (ESI) [M+H]$^+$: 309.03; $^1$H NMR (400 MHz, $CDCl_3$) δ 9.68 (s, 1H), 6.92 (d, J=1.9 Hz, 1H), 6.88 (dd, J=8.2, 2.0 Hz, 1H), 6.69 (d, J=8.2 Hz, 1H), 4.10 (q, J=6.8 Hz, 1H), 3.88-3.75 (m, 1H), 2.08-1.94 (m, 2H), 1.78-1.55 (m, 6H), 1.14 (d, J=6.8 Hz, 3H).

d) NaH (1.61 g, 67.27 mmol) was suspended in 100 mL of dry DMF, stirred for 5 min in an ice-bath, and 80 mL solution of compound D (10.4 g, 33.63 mmol) in DMF was added and stirred for 20 minutes. Iodomethane (3.14 mL, 50.45 mmol) was slowly added dropwise, and the system was reacted at room temperature for 4 hours. The reaction was monitored by TLC plate. After the reaction was completed, the reaction was quenched by adding water in an ice bath, 300 mL of water was added, and the mixture was extracted with ethyl acetate twice. The combined organic phase was washed once with 600 mL of saturated brine, dried over anhydrous sodium sulfate and the solvent was evaporated. The organic phase was purified by silica gel column chromatography and eluted with ethyl acetate/petroleum ether (0-25%) to give 10 g of brown oil E, yield 92%. $^1$H NMR (400 MHz, $CDCl_3$) δ 6.97 (dd, J=8.4, 2.1 Hz, 1H), 6.92 (d, J=2.1 Hz, 1H), 6.78 (d, J=8.5 Hz, 1H), 4.17 (q, J=6.8 Hz, 1H), 3.81-3.72 (m, 1H), 3.33 (s, 3H), 2.08-1.96 (m, 2H), 1.84-1.74 (m, 1H), 1.72-1.58 (m, 5H), 1.05 (d, J=6.8 Hz, 3H).

e) E (10 g, 30.96 mmol), bis(pinacolato)diboron (8.65 g, 34.06 mmol) and potassium acetate (6.08 g, 61.92 mmol) were dissolved in 400 mL anhydrous dioxane, argon gas was ventilated for 10 minutes. [1,1'-bis(diphenylphosphino)ferrocene]palladium dichloride dichloromethane complex (1.26 g, 1.55 mmol) was added and argon gas was ventilated for 2 minutes. The mixture was heated to 120° C. under argon protection and refluxed overnight. The reaction was monitored by TLC plate. After the reaction was completed, the mixture was extracted with dichloromethane (400 mL*2) and 40 mL of water. The organic layers were combined, washed once with 800 mL of saturated brine, dried over anhydrous sodium sulfate. The organic phase was purified by silica gel column chromatography and eluted with gradient ethyl acetate/petroleum ether (0-10%) to give 9.5 g of brown oil F, yield 83%. MS (ESI) [M+H]$^+$: 371.14; $^1$H NMR (400 MHz, $CDCl_3$) δ 7.36 (d, J=8.3 Hz, 1H), 7.29 (s, 1H), 6.95 (d, J=7.9 Hz, 1H), 4.17 (q, J=6.8 Hz, 1H), 3.94-3.85 (m, 1H), 3.37 (s, 3H), 2.09-1.98 (m, 2H), 1.83-1.74 (m, 1H), 1.73-1.58 (m, 5H), 1.35 (s, 12H), 1.03 (d, J=6.9 Hz, 3H).

f) F (1 g, 2.70 mmol), ethyl 5-bromo-1-(p-tolyl)-1H-1,2,4-triazole-3-carboxylate (1.17 g, 3.78 mmol) and a saturated solution of sodium bicarbonate (0.45 g, 5.40 mmol) were dissolved in 10 mL of THF, and argon gas was ventilated for 10 minutes. [1,1'-bis(diphenylphosphino)ferrocene]palladium dichloride dichloromethane complex (0.22 g, 0.27 mmol) was added and argon gas was ventilated for another 2 minutes. The mixture was heated to 80° C. under argon protection and refluxed overnight. The reaction was monitored by TLC plate. After the reaction was completed, the mixture was extracted with 40 mL dichloromethane, washed with saturated brine, and dried over anhydrous sodium sulfate. The organic phase was purified by silica gel column chromatography and eluted with ethyl acetate/petroleum ether (0-25%) to give 0.8 g of brown oil G, yield 63%. MS (ESI) [M+H]$^+$: 474.35; $^1$H NMR (400 MHz, $CDCl_3$) δ 7.29 (d, J=8.4 Hz, 2H), 7.24 (d, J=8.3 Hz, 2H), 7.20-7.16 (m, 1H), 6.90 (d, J=8.4 Hz, 1H), 6.85 (s, 1H), 4.53 (q, J=7.3 Hz, 2H), 3.52-3.42 (m, 1H), 3.35 (s, 3H), 2.40 (s, 3H), 1.84-1.77 (m, 1H), 1.74-1.64 (m, 3H), 1.61-1.48 (m, 5H), 1.45 (t, J=7.1 Hz, 3H), 0.97 (d, J=6.8 Hz, 3H).

g) G (0.8 g, 1.69 mmol) and lithium hydroxide (0.28 g, 6.76 mmol) were dissolved in 10 mL mixed solvent of THF and $H_2O$ (4:1) and then reacted at room temperature for 12 hours. The reaction was monitored by TLC plate. After the reaction was completed, the mixture was adjust to pH 5-6 with 1N HCl, extracted with ethyl acetate (20 mL*2) and 20 mL of water. The organic layers were combined, washed once with 20 mL saturated brine. The organic phase was dried over anhydrous sodium sulfate, filtrated, and directly dried by rotary evaporation to give 0.75 g of white powder H, yield 99%. MS (ESI) [M+H]$^+$: 446.30; $^1$H NMR (400 MHz, $CDCl_3$) δ 8.81 (s, 1H), 7.30 (d, J=8.2 Hz, 2H), 7.26-7.19 (m, 3H), 6.93 (d, J=8.2 Hz, 1H), 6.84 (s, 1H), 4.19 (q, J=6.7 Hz, 1H), 3.50-3.40 (m, 1H), 3.35 (s, 3H), 2.39 (s, 3H), 1.84-1.74 (m, 1H), 1.71-1.62 (m, 1H), 1.61-1.42 (m, 5H), 1.36-1.24 (m, 1H), 0.98 (d, J=6.8 Hz, 3H).

h) Compound H (0.75 g, 1.69 mmol) was dissolved in 5 mL of DMF, then HATU (0.64 g, 1.69 mmol) was added and reacted at room temperature for half an hour, then N-methylpiperazine (0.19 mL, 1.69 mmol) and DIPEA (0.29) were added, and then reacted at room temperature overnight. The reaction was monitored by TLC plate. After the reaction was completed, the mixture was extracted with ethyl acetate (20 mL*2) and 60 mL of saturated sodium bicarbonate. The organic layers were combined, washed once with 40 mL of saturated brine. The organic phase was dried over anhydrous sodium sulfate, purified by silica gel column chromatography and eluted with methanol/dichloromethane (0-10%) to give 0.5 g of white solid compound 6, yield 56%. MS (ESI) [M+H]$^+$: 528.41; $^1$H NMR (400 MHz, $CDCl_3$) δ 7.29-7.26 (m, 2H), 7.25-7.22 (m, 2H), 7.14 (dd, J=8.3, 1.9 Hz, 1H), 6.90 (d, J=8.4 Hz, 1H), 6.84 (d, J=1.9 Hz, 1H), 4.12 (q, J=6.8 Hz, 1H), 4.01-3.92 (m, 2H), 3.90-3.83 (m, 2H), 3.48-3.40 (m, 1H), 3.34 (s, 3H), 2.54-2.49 (m, 2H), 2.49-2.45 (m, 2H), 2.39 (s, 3H), 2.32 (s, 3H), 1.84-1.74 (m, 1H), 1.72-1.63 (m, 1H), 1.61-1.43 (m, 5H), 1.35-1.27 (m, 1H), 0.97 (d, J=6.8 Hz, 3H); $^{13}$C NMR (126 MHz, $CDCl_3$) δ 169.08, 160.70, 156.86, 154.45, 139.61, 135.72, 135.52, 132.26, 130.15 (2×C), 125.67 (2×C), 122.18, 120.21, 116.16, 114.56, 59.05, 55.48, 54.71, 54.56, 47.10, 46.10, 42.43, 30.78, 30.35, 29.24, 24.01, 23.55, 21.30, 14.14.

Example 7

Compound 7 was prepared in the same manner as in example 6 except that ethyl 5-bromo-1-(p-tolyl)-1H-1,2,4- triazole-3-carboxylate was replaced by ethyl 5-bromo-1-phenyl-1H-1,2,4-triazole-3-carboxylate in step f.

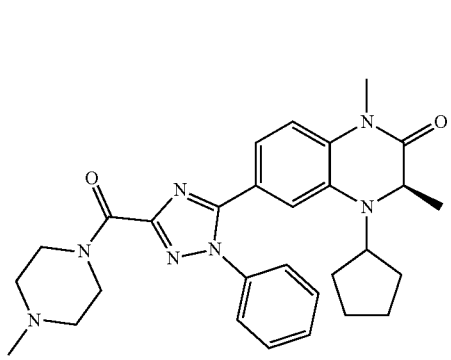

7

MS (ESI)[M+H]⁺: 514.44; ¹H NMR (400 MHz, CDCl₃) δ 7.47-7.36 (m, 5H), 7.11 (dd, J=8.3, 1.5 Hz, 1H), 6.89 (d, J=8.3 Hz, 1H), 6.84 (s, 1H), 4.11 (q, J=6.7 Hz, 1H), 3.99-3.92 (m, 2H), 3.89-3.82 (m, 2H), 3.47-3.37 (m, 1H), 3.33 (s, 3H), 2.54-2.44 (m, 4H), 2.31 (s, 3H), 1.82-1.72 (m, 1H), 1.70-1.61 (m, 1H), 1.60-1.42 (m, 5H), 1.34-1.25 (m, 1H), 0.96 (d, J=6.8 Hz, 3H); ¹³C NMR (126 MHz, CDCl₃) δ 169.01, 160.59, 156.96, 154.52, 138.14, 135.53, 132.29, 129.57 (2×C), 129.29, 125.78 (2×C), 122.03, 120.14, 116.13, 114.54, 59.02, 55.43, 54.65, 54.49, 47.06, 46.05, 42.40, 30.72, 30.32, 29.20, 23.96, 23.50, 14.16.

Example 8

Compound 8 was prepared in the same manner as in example 6 except that ethyl 5-bromo-1-(p-tolyl)-1H-1,2,4-triazole-3-carboxylate was replaced by ethyl 5-bromo-1-phenyl-1H-1,2,4-triazole-3-carboxylate in step f and N-methylpiperazine were replaced by 1-methyl-1,4-diazo-cycloheptane in step h.

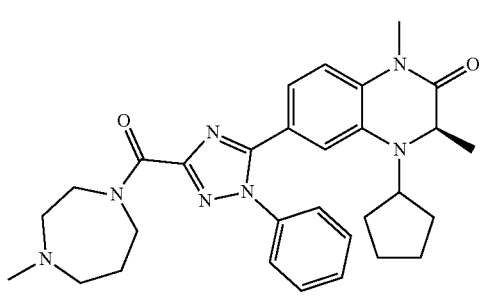

8

MS (ESI)[M+H]⁺: 528.43; ¹H NMR (400 MHz, CDCl₃) δ 7.47-7.42 (m, 3H), 7.41-7.37 (m, 2H), 7.14-7.08 (m, 1H), 6.89 (d, J=8.3 Hz, 1H), 6.86 (dd, J=4.2, 1.8 Hz, 1H), 4.16-4.09 (m, 1H), 3.99-3.94 (m, 1H), 3.93-3.85 (m, 2H), 3.83 (t, J=6.3 Hz, 1H), 3.49-3.39 (m, 1H), 3.34 (s, 3H), 2.82-2.77 (m, 2H), 2.71-2.63 (m, 2H), 2.40 (d, J=8.1 Hz, 3H), 2.10-1.99 (m, 2H), 183-1.74 (m, 1H), 1.71-1.62 (m, 1H), 1.61-1.42 (m, 6H), 0.98 (dd, J=6.8, 1.3 Hz, 3H).

Example 9

Compound 9 was prepared in the same manner as in example 6 except that ethyl 5-bromo-1-(p-tolyl)-1H-1,2,4-triazole-3-carboxylate was replaced by ethyl 5-bromo-1-(2,4-dimethylphenyl)-1H-1,2,4-triazole-3-carboxylate in step f.

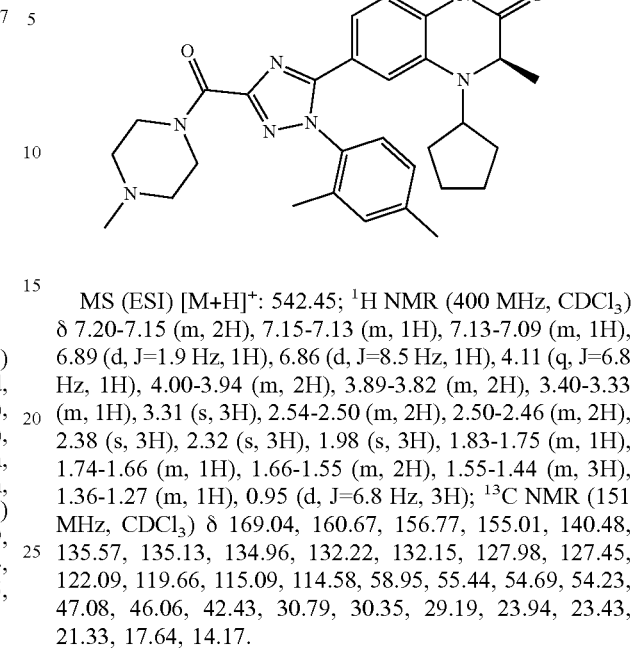

9

MS (ESI) [M+H]⁺: 542.45; ¹H NMR (400 MHz, CDCl₃) δ 7.20-7.15 (m, 2H), 7.15-7.13 (m, 1H), 7.13-7.09 (m, 1H), 6.89 (d, J=1.9 Hz, 1H), 6.86 (d, J=8.5 Hz, 1H), 4.11 (q, J=6.8 Hz, 1H), 4.00-3.94 (m, 2H), 3.89-3.82 (m, 2H), 3.40-3.33 (m, 1H), 3.31 (s, 3H), 2.54-2.50 (m, 2H), 2.50-2.46 (m, 2H), 2.38 (s, 3H), 2.32 (s, 3H), 1.98 (s, 3H), 1.83-1.75 (m, 1H), 1.74-1.66 (m, 1H), 1.66-1.55 (m, 2H), 1.55-1.44 (m, 3H), 1.36-1.27 (m, 1H), 0.95 (d, J=6.8 Hz, 3H); ¹³C NMR (151 MHz, CDCl₃) δ 169.04, 160.67, 156.77, 155.01, 140.48, 135.57, 135.13, 134.96, 132.22, 132.15, 127.98, 127.45, 122.09, 119.66, 115.09, 114.58, 58.95, 55.44, 54.69, 54.23, 47.08, 46.06, 42.43, 30.79, 30.35, 29.19, 23.94, 23.43, 21.33, 17.64, 14.17.

Example 10

Compound 10 was prepared in the same manner as in example 6 except that N-methylpiperazine was replaced by 1-ethylpiperazine in step h.

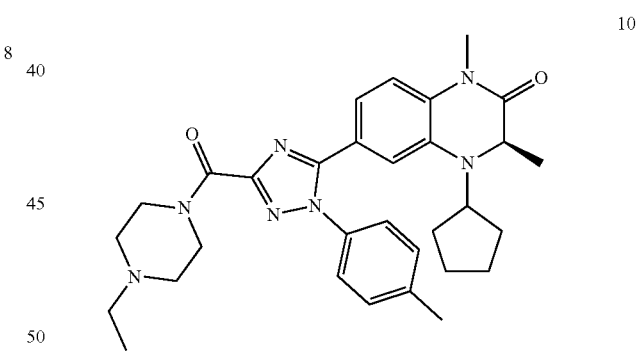

10

MS (ESI) [M+H]⁺: 542.42; ¹H NMR (400 MHz, CDCl₃) δ 7.30-7.26 (m, 2H), 7.25-7.22 (m, 2H), 7.15 (dd, J=8.3, 1.8 Hz, 1H), 6.90 (d, J=8.4 Hz, 1H), 6.86 (d, J=1.8 Hz, 1H), 4.13 (q, J=6.8 Hz, 1H), 4.05-3.95 (m, 2H), 3.94-3.84 (m, 2H), 3.50-3.41 (m, 1H), 3.35 (s, 3H), 2.59-2.51 (m, 4H), 2.47 (q, J=7.2 Hz, 2H), 2.40 (s, 3H), 1.84-1.75 (m, 1H), 1.73-1.64 (m, 1H), 1.62-1.44 (m, 5H), 1.36-1.28 (m, 1H), 1.11 (t, J=7.2 Hz, 3H), 0.98 (d, J=6.8 Hz, 3H).

Example 11

Compound 11 was prepared in the same manner as in example 6 except that N-methylpiperazine was replaced by 1-cyclopropylpiperazine in step h.

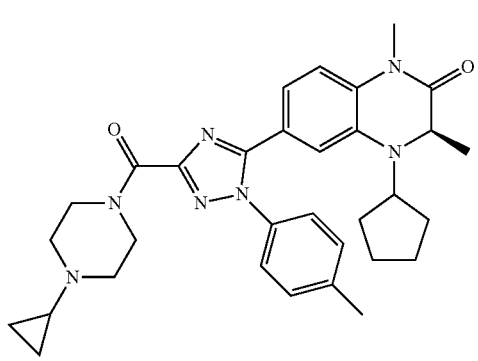

11

MS (ESI) [M+H]⁺: 554.44; ¹H NMR (400 MHz, CDCl₃) δ 7.30-7.21 (m, 4H), 7.15 (d, J=7.2 Hz, 1H), 6.90 (d, J=8.4 Hz, 1H), 6.85 (s, 1H), 4.21-4.04 (m, 1H), 3.93-3.86 (m, 2H), 3.84-3.76 (m, 2H), 3.50-3.39 (m, 1H), 3.34 (s, 3H), 2.75-2.62 (m, 4H), 2.39 (s, 3H), 2.28-2.15 (m, 1H), 1.82-1.74 (m, 1H), 1.69-1.63 (m, 2H), 1.58-1.46 (m, 5H), 0.97 (d, J=6.7 Hz, 3H), 0.87-0.82 (m, 2H), 0.49-0.43 (m, 2H); ¹³C NMR (126 MHz, CDCl₃) δ 169.05, 160.68, 156.92, 154.41, 139.56, 135.72, 135.50, 132.24, 130.13 (2×C), 125.66 (2×C), 122.19, 120.20, 116.16, 114.53, 59.03, 54.54, 53.77, 52.97, 47.21, 42.53, 38.41, 30.77, 30.34, 29.77, 29.21, 24.00, 23.53, 21.28, 14.12, 5.99.

Example 12

Compound 12 was prepared in the same manner as in example 6 except that N-methylpiperazine was replaced by (2S,6R)-2,6-dimethylpiperazine in step h.

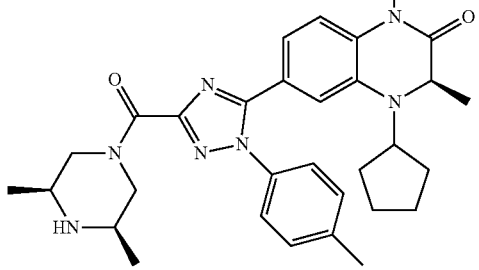

12

MS (ESI)[M+H]⁺: 542.43; ¹H NMR (400 MHz, CDCl₃) δ 7.30-7.21 (m, 4H), 7.16-7.11 (m, 1H), 6.90 (dd, J=8.3, 2.7 Hz, 1H), 6.85 (d, J=7.3 Hz, 1H), 4.68 (d, J=12.9 Hz, 1H), 4.44 (d, J=11.9 Hz, 1H), 4.12 (q, J=6.8 Hz, 1H), 3.49-3.39 (m, 1H), 3.33 (s, 3H), 3.04-2.89 (m, 2H), 2.89-2.78 (m, 1H), 2.48-2.40 (m, 1H), 2.38 (s, 3H), 2.34 (s, 1H), 1.82-1.74 (m, 1H), 1.72-1.63 (m, 1H), 1.62-1.42 (m, 6H), 1.14 (d, J=6.2 Hz, 3H), 1.07 (d, J=5.8 Hz, 3H), 0.97 (d, J=6.6 Hz, 3H); ¹³C NMR (151 MHz, CDCl₃) δ 169.04, 160.50 (d, J=5.1 Hz), 156.88, 154.42, 139.60, 135.63, 135.50, 132.22, 130.13 (2×C), 125.63 (2×C), 122.10, 120.15, 116.07, 114.55 (d, J=4.2 Hz), 58.95, 54.52, 53.49 (d, J=4.0 Hz), 51.62, 50.79, 48.70, 30.77, 30.32 (d, J=4.3 Hz), 29.21, 23.98, 23.51, 21.28, 19.38, 19.19, 14.07 (d, J=5.5 Hz).

Example 13

Compound 13 was prepared in the same manner as in example 6 except that N-methylpiperazine was replaced by N¹,N¹,N²-trimethylethane-1,2-diamine in step h.

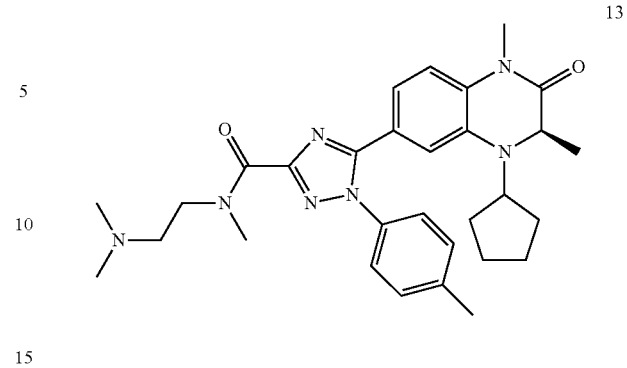

13

MS (ESI)[M+H]⁺: 530.32. ¹H NMR (400 MHz, CDCl₃) δ 7.26-7.19 (m, 4H), 7.13 (dt, J=8.3, 2.1 Hz, 1H), 6.90 (dd, J=8.4, 4.1 Hz, 1H), 6.77 (dd, J=19.2, 1.6 Hz, 1H), 4.10 (q, J=6.7 Hz, 1H), 3.85-3.79 (m, 1H), 3.78-3.69 (m, 2H), 3.45-3.35 (m, 1H), 3.34 (s, 2H), 3.32 (s, 3H), 2.84 (t, J=6.5 Hz, 1H), 2.74-2.66 (m, 1H), 2.49 (s, 3H), 2.37 (s, 3H), 2.24 (s, 3H), 1.81-1.70 (m, 1H), 1.69-1.59 (m, 1H), 1.60-1.40 (m, 5H), 1.31-1.24 (m, 1H), 0.95 (dd, J=6.8, 2.7 Hz, 3H).

Example 14

Compound 14 was prepared in the same manner as in example 6 except that N-methylpiperazine was replaced by 8-methyl-3,8-diazabicyclo[3.2.1]octane in step h.

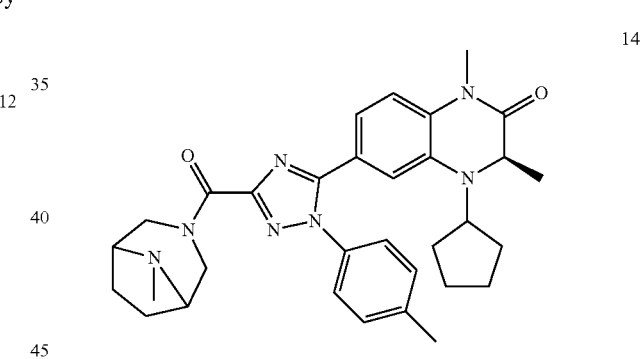

14

MS (ESI) [M+H]⁺: 554.44; ¹H NMR (400 MHz, CDCl₃) δ 7.30-7.20 (m, 4H), 7.14 (d, J=8.2 Hz, 1H), 6.89 (d, J=8.4 Hz, 1H), 6.85 (s, 1H), 5.15 (s, 1H), 4.87 (d, J=5.9 Hz, 1H), 4.12 (q, J=6.7 Hz, 1H), 3.51-3.39 (m, 1H), 3.33 (s, 3H), 2.74 (d, J=10.1 Hz, 2H), 2.50-2.42 (m, 2H), 2.38 (s, 3H), 2.25 (s, 3H), 2.03-1.91 (m, 4H), 1.83-1.74 (m, 1H), 1.71-1.63 (m, 1H), 1.61-1.42 (m, 6H), 0.97 (d, J=6.8 Hz, 3H); ¹³C NMR (126 MHz, CDCl₃) δ 169.03, 157.24, 157.01, 154.41, 139.52, 135.80, 135.44, 132.18, 130.08 (2×C), 125.67 (2×C), 122.27, 120.20, 116.18, 114.49, 61.95, 60.28, 59.03, 56.44, 54.57, 52.85, 45.18, 30.74, 30.32, 29.20, 28.66, 26.78, 23.97, 23.52, 21.28, 14.11.

Example 15

Compound 15 was prepared in the same manner as in example 6 except that N-methylpiperazine was replaced by 1-isopropylpiperazine in step h.

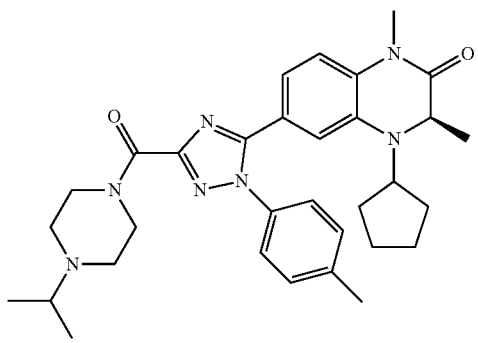

15

MS (ESI) [M+H]⁺: 556.44; ¹H NMR (400 MHz, CDCl₃) δ 7.30-7.26 (m, 2H), 7.26-7.22 (m, 2H), 7.15 (dd, J=8.3, 1.9 Hz, 1H), 6.91 (d, J=8.4 Hz, 1H), 6.84 (d, J=1.8 Hz, 1H), 4.13 (q, J=6.8 Hz, 1H), 4.01-3.94 (m, 2H), 3.91-3.83 (m, 2H), 3.48-3.40 (m, 1H), 3.34 (s, 3H), 2.83-2.70 (m, 1H), 2.69-2.57 (m, 4H), 2.39 (s, 3H), 1.84-1.75 (m, 1H), 1.72-1.64 (m, 1H), 1.63-1.44 (m, 5H), 1.34-1.27 (m, 1H), 1.06 (d, J=6.6 Hz, 6H), 0.98 (d, J=6.8 Hz, 3H); ¹³C NMR (151 MHz, CDCl₃) δ 169.10, 160.58, 156.87, 154.47, 139.62, 135.70, 135.53, 132.26, 130.17 (2×C), 125.69 (2×C), 122.18, 120.22, 116.16, 114.58, 59.01, 54.84, 54.58, 49.31, 48.32, 47.45, 42.75, 30.80, 30.35, 29.25, 24.03, 23.56, 21.32, 18.45 (2×C), 14.11.

Example 16

Compound 16 was prepared in the same manner as in example 6 except that ethyl 5-bromo-1-(p-tolyl)-1H-1,2,4-triazole-3-carboxylate was replaced by ethyl 5-bromo-1-(3-fluoro-4-methylphenyl)-1H-1,2,4-triazole-3-carboxylate in step f.

16

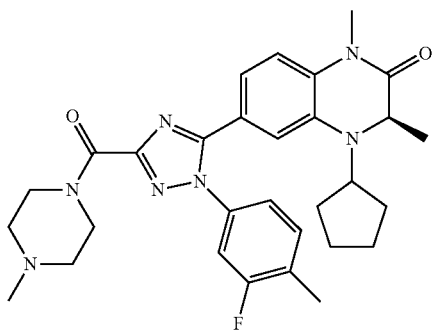

MS (ESI) [M+H]⁺: 546.40; ¹H NMR (400 MHz, CDCl₃) δ 7.22 (t, J=8.0 Hz, 1H), 7.11-7.03 (m, 3H), 6.89 (d, J=8.4 Hz, 1H), 6.83 (d, J=1.7 Hz, 1H), 4.11 (q, J=6.8 Hz, 1H), 3.94-3.88 (m, 2H), 3.87-3.79 (m, 2H), 3.53-3.43 (m, 1H), 3.32 (s, 3H), 2.52-2.42 (m, 4H), 2.29 (s, 3H), 2.28 (d, J=1.5 Hz, 3H), 1.84-1.75 (m, 1H), 1.72-1.62 (m, 1H), 1.60-1.43 (m, 5H), 1.37-1.24 (m, 1H), 0.96 (d, J=6.8 Hz, 3H).

Example 17

Compound 17 was prepared in the same manner as in example 6 except that ethyl 5-bromo-1-(p-tolyl)-1H-1,2,4-triazole-3-carboxylate was replaced by ethyl 5-bromo-1-(4-chlorophenyl)-1H-1,2,4-triazole-3-carboxylate in step f.

17

MS (ESI) [M+H]⁺: 548.38; ¹H NMR (400 MHz, CDCl₃) δ 7.44-7.39 (m, 2H), 7.37-7.32 (m, 2H), 7.08 (dd, J=8.3, 1.7 Hz, 1H), 6.91 (d, J=8.3 Hz, 1H), 6.82 (d, J=1.7 Hz, 1H), 4.14 (q, J=6.8 Hz, 1H), 4.00-3.90 (m, 2H), 3.90-3.79 (m, 2H), 3.55-3.43 (m, 1H), 3.34 (s, 3H), 2.55-2.50 (m, 2H), 2.50-2.45 (m, 2H), 2.32 (s, 3H), 1.87-1.78 (m, 1H), 1.74-1.66 (m, 1H), 1.63-1.46 (m, 5H), 1.37-1.28 (m, 1H), 0.99 (d, J=6.8 Hz, 3H); ¹³C NMR (126 MHz, CDCl₃) δ 169.00, 160.42, 157.21, 154.67, 136.56, 135.71, 135.35, 132.52, 129.80 (2×C), 127.00 (2×C), 121.74, 120.14, 116.06, 114.67, 59.11, 55.46, 54.68, 54.55, 47.07, 46.08, 42.45, 30.81, 30.43, 29.25, 24.05, 23.57, 14.22.

Example 18

Compound 18 was prepared in the same manner as in example 6 except that N-methylpiperazine was replaced by 3-methyl-3,8-diazabicyclo[3.2.1]octane in step h.

18

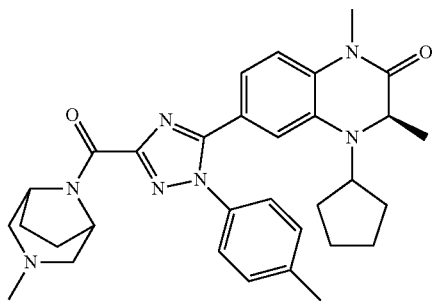

MS (ESI) [M+H]⁺: 554.42; ¹H NMR (400 MHz, CDCl₃) δ 7.29-7.21 (m, 4H), 7.15 (d, J=8.3 Hz, 1H), 6.90 (d, J=8.4 Hz, 1H), 6.83 (t, J=2.0 Hz, 1H), 5.21 (s, 1H), 4.88 (d, J=6.2 Hz, 1H), 4.12 (q, J=6.8 Hz, 1H), 3.47-3.38 (m, 1H), 3.33 (s, 3H), 2.85-2.77 (m, 2H), 2.50 (dd, J=15.8, 11.1 Hz, 2H), 2.38 (s, 3H), 2.29 (d, J=2.2 Hz, 3H), 2.06-1.86 (m, 4H), 1.82-1.73 (m, 1H), 1.73-1.63 (m, 1H), 1.60-1.42 (m, 6H), 0.96 (d, J=6.8 Hz, 3H); ¹³C NMR (151 MHz, CDCl₃) δ 169.03, 157.06, 156.97, 154.50, 139.59, 135.69, 135.43, 132.20, 130.11 (2×C), 125.65 (2×C), 122.14, 120.19, 116.12, 114.54, 61.83, 60.20, 58.96, 56.33, 54.56, 52.81, 45.12, 30.73, 30.28, 29.19, 28.52, 26.59, 23.96, 23.50, 21.27, 14.06 (d, J=2.9 Hz).

Example 19

Compound 19 was prepared in the same manner as in example 6 except that N-methylpiperazine was replaced by 1-methyl-1,4-diazacycloheptane in step h.

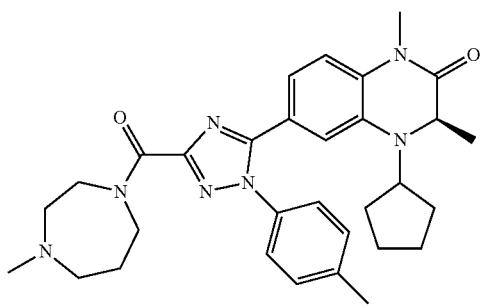

19

MS (ESI) [M+H]+: 542.39. 1H NMR (400 MHz, CDCl3) δ 7.30-7.26 (m, 2H), 7.25-7.22 (m, 2H), 7.14 (ddd, J=8.1, 6.2, 1.8 Hz, 1H), 6.91 (d, J=8.4 Hz, 1H), 6.86 (dd, J=3.9, 1.8 Hz, 1H), 4.18-4.10 (m, 1H), 4.00-3.95 (m, 1H), 3.91 (t, J=6.4 Hz, 1H), 3.89-3.86 (m, 1H), 3.83 (t, J=6.4 Hz, 1H), 3.50-3.41 (m, 1H), 3.35 (s, 3H), 2.85-2.78 (m, 2H), 2.73-2.64 (m, 2H), 2.45-2.38 (m, 6H), 2.09-1.98 (m, 2H), 1.84-1.76 (m, 1H), 1.73-1.65 (m, 1H), 1.63-1.45 (m, 5H), 1.37-1.27 (m, 1H), 0.99 (dd, J=6.8, 1.3 Hz, 3H).

Example 20

Compound 20 was prepared in the same manner as in example 6 except that N-methylpiperazine was replaced by 8-azaspiro[4.5]decane in step h.

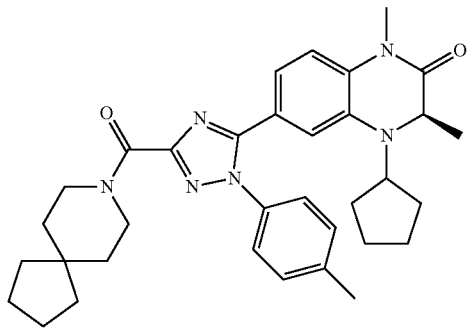

20

1H NMR (400 MHz, CDCl3) δ 7.28-7.24 (m, 2H), 7.21 (d, J=8.3 Hz, 2H), 7.13 (dd, J=8.3, 1.9 Hz, 1H), 6.88 (d, J=8.4 Hz, 1H), 6.84 (d, J=1.8 Hz, 1H), 4.11 (q, J=6.8 Hz, 1H), 3.80-3.70 (m, 4H), 3.48-3.38 (m, 1H), 3.32 (s, 3H), 2.37 (s, 3H), 1.83-1.73 (m, 1H), 1.69-1.58 (m, 5H), 1.56-1.43 (m, 13H), 1.33-1.24 (m, 1H), 0.96 (d, J=6.8 Hz, 3H); 13C NMR (126 MHz, CDCl3) δ 168.99, 160.82, 157.27, 154.26, 139.39, 135.73, 135.42, 132.12, 130.04 (2×C), 125.60 (2×C), 122.27, 120.15, 116.13, 114.46, 58.98, 54.49, 45.36, 41.48, 40.54, 38.21, 37.78, 37.73, 37.01, 30.72, 30.29, 29.16, 24.34 (2×C), 23.95, 23.48, 21.23, 14.07.

Example 21

Compound 21 was prepared in the same manner as in example 6 except that N-methylpiperazine was replaced by 2-oxo-8-azaspiro[4.5]decane in step h.

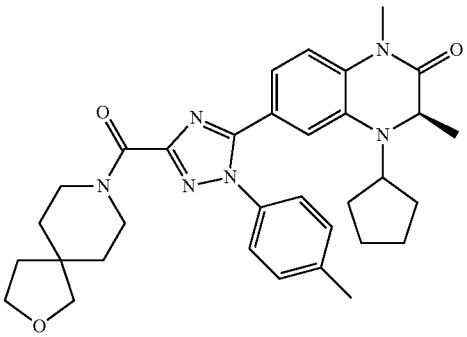

21

MS (ESI) [M+H]+: 569.49. 1H NMR (400 MHz, CDCl3) δ 7.31-7.26 (m, 2H), 7.23 (d, J=8.3 Hz, 2H), 7.14 (dd, J=8.3, 1.5 Hz, 1H), 6.90 (d, J=8.4 Hz, 1H), 6.85 (s, 1H), 4.13 (q, J=6.8 Hz, 1H), 3.89 (t, J=7.1 Hz, 3H), 3.80-3.69 (m, 2H), 3.60 (d, J=1.0 Hz, 2H), 3.47-3.39 (m, 1H), 3.34 (s, 3H), 2.39 (s, 3H), 1.86-1.76 (m, 4H), 1.72-1.65 (m, 5H), 1.60-1.45 (m, 6H), 0.98 (d, J=6.8 Hz, 3H); 13C NMR (126 MHz, CDCl3) δ 169.06, 160.90, 157.08, 154.43, 139.56, 135.74, 135.52, 132.26, 130.14 (2×C), 125.66 (2×C), 122.23, 120.20, 116.16, 114.54, 67.42, 59.05, 54.55, 45.37, 42.38, 40.73, 37.33, 37.29, 35.78, 34.60, 30.79, 30.36, 29.23, 24.02, 23.55, 21.30, 14.15.

Example 22

Compound 22 was prepared in the same manner as in example 6 except that N-methylpiperazine was replaced by 1,4-diazabicyclo[4.3.0]decane in step h.

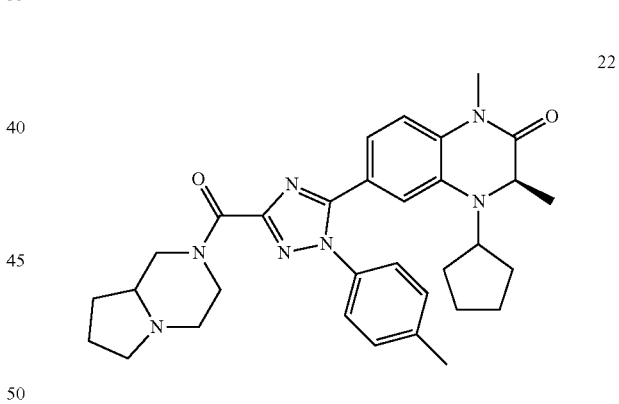

22

MS (ESI) [M+H]+: 554.46. 1H NMR (400 MHz, CDCl3) δ 7.31-7.20 (m, 4H), 7.14 (d, J=8.1 Hz, 1H), 6.90 (d, J=8.4 Hz, 1H), 6.88-6.83 (m, 1H), 4.84 (dd, J=54.8, 12.9 Hz, 1H), 4.56 (dd, J=26.1, 13.0 Hz, 1H), 4.12 (q, J=6.9 Hz, 1H), 3.49-3.39 (m, 1H), 3.34 (s, 3H), 3.11 (t, J=8.5 Hz, 2H), 3.07-2.98 (m, 1H), 2.70-2.61 (m, 1H), 2.39 (s, 3H), 2.30 (t, J=11.1 Hz, 1H), 2.23-2.14 (m, 1H), 2.12-2.01 (m, 1H), 1.95-1.63 (m, 6H), 1.62-1.41 (m, 6H), 0.97 (d, J=6.7 Hz, 3H).

Example 23

Compound 23 was prepared in the same manner as in example 6 except that N-methylpiperazine was replaced by tert-butyl (7S)-5-azaspiro[2.4]heptan-7-yl carbamate in step h.

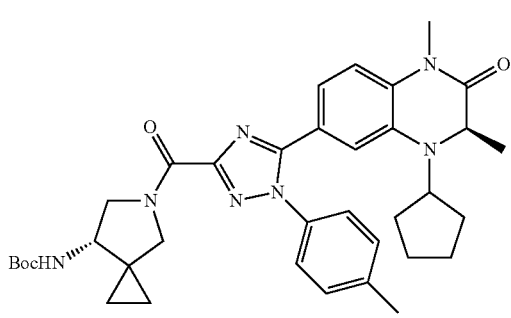

23

MS (ESI) [M+H]⁺: 640.31. ¹H NMR (400 MHz, CDCl₃) δ 7.27-7.19 (m, 5H), 7.16-7.09 (m, 1H), 6.87 (dd, J=8.4, 3.2 Hz, 1H), 6.82 (d, J=3.5 Hz, 1H), 4.89-4.79 (m, 1H), 4.29 (dd, J=12.1, 5.3 Hz, 1H), 4.18-4.07 (m, 2H), 4.00 (dd, J=12.9, 5.7 Hz, 1H), 3.92-3.85 (m, 1H), 3.83-3.69 (m, 2H), 3.53-3.38 (m, 2H), 3.31 (d, J=2.7 Hz, 3H), 2.37 (s, 3H), 1.81-1.72 (m, 1H), 1.69-1.61 (m, 1H), 1.59-1.44 (m, 6H), 1.42-1.36 (m, 10H), 0.95 (dd, J=6.8, 1.4 Hz, 3H).

Example 24

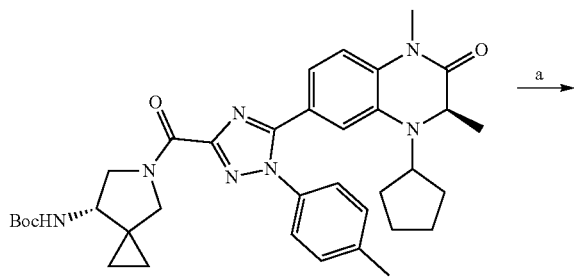

23 a →

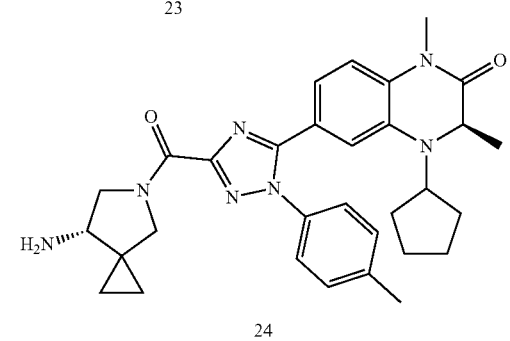

24 a) Compound 23 (0.1 g, 0.16 mmol) was dissolved in 1 mL of dichloromethane, 0.5 mL of trifluoroacetic acid was added and then reacted at room temperature for 3 hours. The reaction was monitored by TLC plate. After the reaction was completed, the pH was adjusted to 7-8 with saturated NaHCO₃. Then the mixture was extracted with ethyl acetate (10 mL*2) and 10 mL of water. The combined organic phase was washed once with 20 mL saturated brine. The organic phase was dried over anhydrous sodium sulfate, purified by silica gel column chromatography and eluted with gradient methanol/dichloromethane (0-5%) to give 50 mg of white solid compound 24, yield 58%. ¹H NMR (400 MHz, CDCl₃) δ 7.30-7.22 (m, 4H), 7.20-7.11 (m, 1H), 6.93-6.88 (m, 1H), 6.87-6.84 (m, 1H), 4.36-4.19 (m, 1H), 4.13 (q, J=6.8 Hz, 1H), 4.04-3.94 (m, 1H), 3.87 (dd, J=37.4, 12.0 Hz, 1H), 3.66 (dd, J=56.3, 13.2 Hz, 1H), 3.50-3.40 (m, 1H), 3.34 (d, J=2.3 Hz, 3H), 3.18-3.11 (m, 1H), 2.40 (s, 3H), 2.00 (s, 2H), 1.85-1.74 (m, 1H), 1.73-1.64 (m, 1H), 1.61-1.43 (m, 6H), 0.98 (d, J=6.8 Hz, 3H), 0.83-0.76 (m, 1H), 0.70-0.54 (m, 3H).

Example 25

Compound 25 was prepared in the same manner as in example 6 except that ethyl 5-bromo-1-(p-tolyl)-1H-1,2,4-triazole-3-carboxylate was replaced by 4-bromo-5-methyl-3-phenylisoxazole in step f and steps g-h were absent.

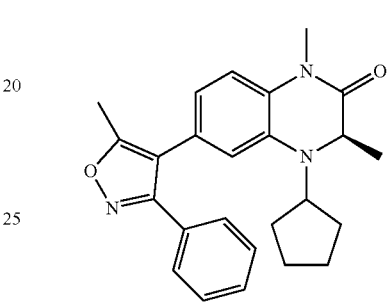

25

MS (ESI) [M+H]⁺: 402.19; ¹H NMR (400 MHz, CDCl₃) δ 7.58-7.55 (m, 2H), 7.36-7.30 (m, 3H), 7.00 (d, J=8.2 Hz, 1H), 6.82 (dd, J=8.1, 1.8 Hz, 1H), 6.66 (d, J=1.8 Hz, 1H), 4.20 (q, J=6.8 Hz, 1H), 3.66-3.56 (m, 1H), 3.41 (s, 3H), 2.29 (s, 3H), 1.90-1.82 (m, 1H), 1.81-1.67 (m, 2H), 1.62-1.46 (m, 5H), 1.08 (d, J=6.8 Hz, 3H); ¹³C NMR (126 MHz, CDCl₃) δ 169.21, 164.42, 160.19, 136.06, 130.61, 129.71, 128.70 (2×C), 128.10, 127.08 (2×C), 125.59, 120.31, 117.29, 116.33, 114.97, 58.99, 55.01, 30.87, 30.79, 29.19, 24.21, 23.74, 13.91, 10.87.

Example 26

Compound 26 was prepared in the same manner as in example 6 except that ethyl 5-bromo-1-(p-tolyl)-1H-1,2,4-triazole-3-carboxylate was replaced by ethyl 5-bromo-1-(p-tolyl)-1H-pyrazole-3-carboxylate in step f.

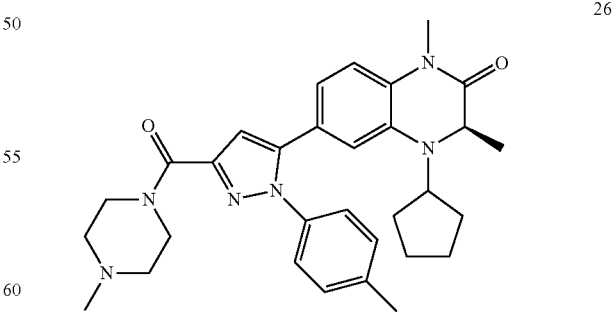

26

MS (ESI) [M+H]⁺: 527.32; ¹H NMR (400 MHz, CDCl₃) δ 7.19-7.10 (m, 4H), 6.89-6.83 (m, 3H), 6.47 (d, J=1.1 Hz, 1H), 4.17-4.05 (m, 3H), 3.87-3.78 (m, 2H), 3.39-3.29 (m, 4H), 2.55-2.43 (m, 4H), 2.31 (s, 6H), 1.79-1.71 (m, 1H), 1.67-1.60 (m, 1H), 1.58-1.38 (m, 5H), 1.20-1.17 (m, 1H), 0.95 (d, J=6.8 Hz, 3H); $^{13}$C NMR (126 MHz, CDCl$_3$) δ 169.02, 162.73, 147.23, 143.83, 138.03, 137.45, 135.34, 130.80, 129.62 (2×C), 125.40 (2×C), 124.80, 119.47, 116.22, 114.50, 109.54, 58.79, 55.52, 54.77, 46.89, 45.96, 42.33, 30.68, 30.19, 29.69, 29.08, 23.97, 23.52, 21.08, 13.76.

Example 27

Compound 27 was prepared in the same manner as in example 6 except that ethyl 5-bromo-1-(p-tolyl)-1H-1,2,4-triazole-3-carboxylate was replaced by ethyl 5-bromo-1-(p-tolyl)-1H-pyrazole-3-carboxylate in step f and N-methylpiperazine was replaced by (2S,6R)-2,6-dimethylpiperazine in step h.

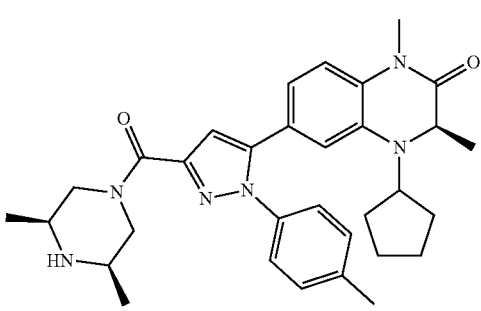

27

MS (ESI) [M+H]$^+$: 541.36; $^1$H NMR (400 MHz, CDCl$_3$) δ 7.18-7.12 (m, 4H), 6.93-6.87 (m, 2H), 6.85 (s, 1H), 6.47 (d, J=3.0 Hz, 1H), 4.92 (d, J=12.9 Hz, 1H), 4.69 (d, J=13.2 Hz, 1H), 4.11 (q, J=6.8 Hz, 1H), 3.50-3.39 (m, 2H), 3.34 (s, 3H), 3.15-3.03 (m, 2H), 3.01-2.92 (m, 1H), 2.63-2.54 (m, 1H), 2.34 (s, 3H), 1.80-1.72 (m, 1H), 1.70-1.61 (m, 1H), 1.60-1.37 (m, 6H), 1.26-1.18 (m, 6H), 0.97 (d, J=6.8 Hz, 3H); $^{13}$C NMR (126 MHz, CDCl$_3$) δ 169.16, 162.79, 146.78, 144.23, 138.32, 137.38, 135.47, 130.97, 129.79 (2×C), 125.40 (2×C), 124.66, 119.62, 116.29, 114.68, 109.47, 58.85, 54.83, 52.48 (d, J=12.8 Hz), 51.75, 49.55, 47.81, 30.76, 30.26, 29.21, 27.07, 24.05, 23.60, 21.16, 18.30 (d, J=23.3 Hz), 13.86.

Example 28

Compound 28 was prepared in the same manner as in example 6 except that ethyl 5-bromo-1-(p-tolyl)-1H-1,2,4-triazole-3-carboxylate was replaced by ethyl 5-bromo-1-(p-tolyl)-1H-pyrazole-3-carboxylate in step f and N-methylpiperazine was replaced by 3-methyl-3,8-diazabicyclo[3.2.1]octane in step h.

MS (ESI) [M+H]$^+$: 553.40; $^1$H NMR (400 MHz, CDCl$_3$) δ 7.21-7.14 (m, 4H), 6.97 (d, J=0.5 Hz, 1H), 6.92-6.85 (m, 2H), 6.51-6.48 (m, 1H), 5.39 (s, 1H), 4.86 (s, 1H), 4.12 (q, J=6.8 Hz, 1H), 3.44-3.29 (m, 4H), 2.84 (t, J=8.7 Hz, 2H), 2.58-2.45 (m, 2H), 2.35 (s, 3H), 2.32 (d, J=3.0 Hz, 3H), 2.07-1.90 (m, 4H), 1.80-1.73 (m, 1H), 1.70-1.62 (m, 1H), 1.57-1.39 (m, 6H), 0.98 (d, J=6.8 Hz, 3H); $^{13}$C NMR (126 MHz, CDCl$_3$) δ 169.12, 159.47, 147.90, 143.87, 138.07, 137.65, 135.45, 130.89, 129.69 (2×C), 125.40 (2×C), 124.99, 119.58, 116.34, 114.58, 109.72, 61.85, 60.39, 58.89, 55.78, 54.88, 52.63 (d, J=4.9 Hz), 45.28, 30.79, 30.31, 29.18, 28.64 (d, J=3.8 Hz), 26.46 (d, J=5.7 Hz), 24.07, 23.62, 21.17, 13.86.

Example 29

Compound 29 was prepared in the same manner as in example 6 except that ethyl 5-bromo-1-(p-tolyl)-1H-1,2,4-triazole-3-carboxylate was replaced by ethyl 5-bromo-1-(p-tolyl)-1H-pyrazole-3-carboxylate in step f and N-methylpiperazine was replaced by 8-methyl-3,8-diazabicyclo[3.2.1]octane in step h.

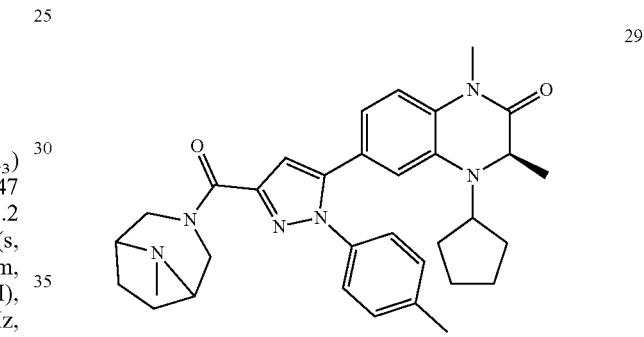

29

MS (ESI) [M+H]$^+$: 553.40; $^1$H NMR (400 MHz, CDCl$_3$) δ 7.22-7.14 (m, 4H), 7.00 (s, 1H), 6.93-6.83 (m, 2H), 6.51 (d, J=5.8 Hz, 1H), 5.44 (s, 1H), 4.89 (s, 1H), 4.13 (q, J=6.6 Hz, 1H), 3.44-3.33 (m, 4H), 2.99-2.81 (m, 2H), 2.65-2.49 (m, 2H), 2.41-2.29 (m, 6H), 2.11-1.92 (m, 4H), 1.83-1.74 (m, 1H), 1.71-1.64 (m, 1H), 1.59-1.42 (m, 6H), 0.99 (d, J=6.8 Hz, 3H).

Example 30

Compound 30 was prepared in the same manner as in example 6 except that ethyl 5-bromo-1-(p-tolyl)-1H-1,2,4-triazole-3-carboxylate was replaced by 5-(2-bromophenyl)oxazole in step f and steps g and h were absent.

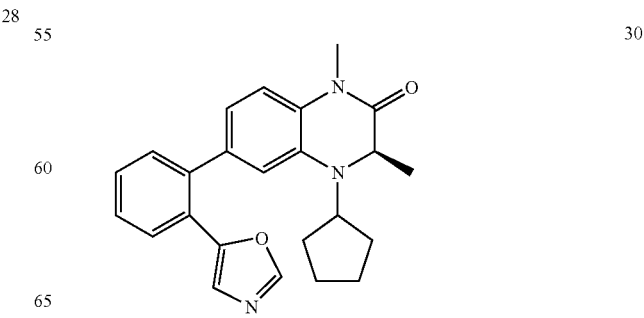

28

30

MS (ESI) [M+H]⁺: 388.11; ¹H NMR (400 MHz, CDCl₃) δ 7.79 (s, 1H), 7.78-7.74 (m, 1H), 7.43 (ddd, J=14.7, 7.2, 1.7 Hz, 2H), 7.39-7.35 (m, 1H), 6.98 (d, J=8.1 Hz, 1H), 6.80 (dd, J=8.1, 1.8 Hz, 1H), 6.69 (d, J=1.6 Hz, 1H), 6.34 (s, 1H), 4.19 (q, J=6.8 Hz, 1H), 3.72-3.60 (m, 1H), 3.41 (s, 3H), 1.91-1.84 (m, 1H), 1.74-1.68 (m, 1H), 1.66-1.47 (m, 6H), 1.08 (d, J=6.8 Hz, 3H).

Example 31

Compound 31 was prepared in the same manner as in example 6 except that ethyl 5-bromo-1-(p-tolyl)-1H-1,2,4-triazole-3-carboxylate was replaced by 2-(2-bromophenyl)-1,3-dioxolane in step f and steps g-h were absent.

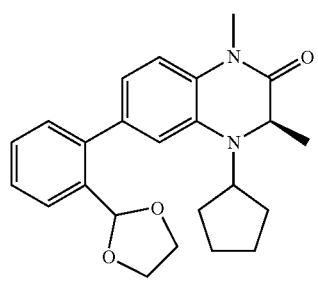

31

MS (ESI) [M+H]⁺: 393.16; ¹H NMR (400 MHz, CDCl₃) δ 7.72 (s, 1H), 7.40 (s, 2H), 7.35-7.27 (m, 1H), 7.01-6.90 (m, 3H), 4.30-4.11 (m, 3H), 3.93 (s, 2H), 3.86-3.74 (m, 1H), 3.40 (s, 3H), 2.14-1.92 (m, 2H), 1.85-1.51 (m, 7H), 1.08 (d, J=6.5 Hz, 3H).

Example 32

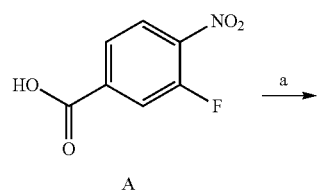

A

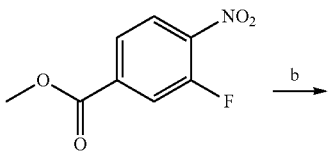

B

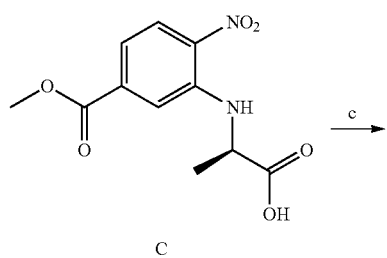

C

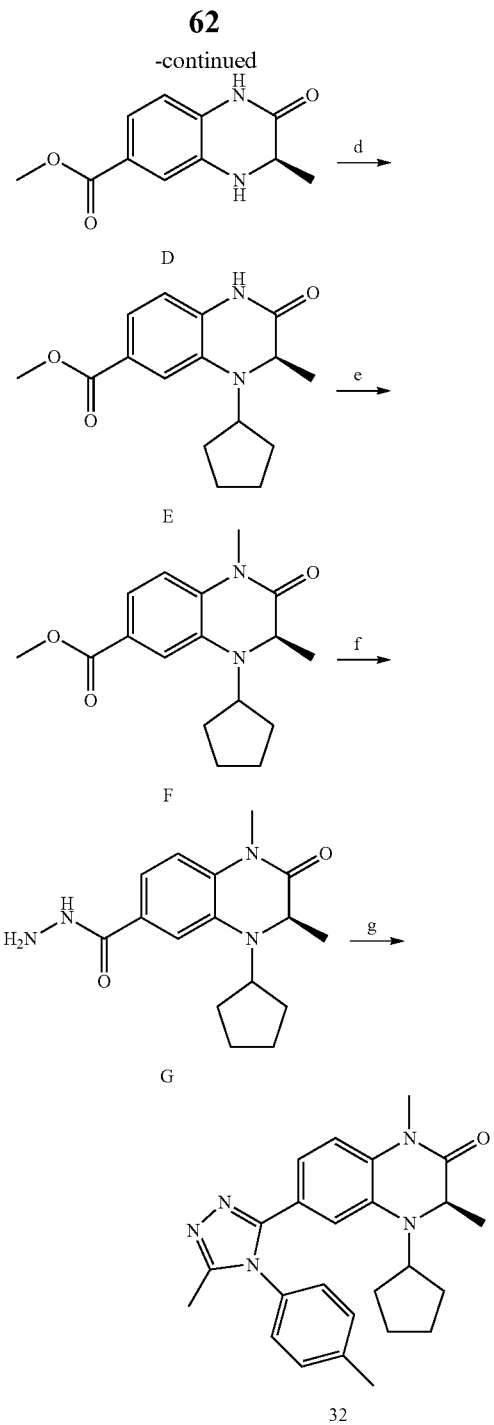

Step a in example 32 was carried out in the same manner as step a in example 1. Steps b-e were carried out in the same manner as steps a-d in example 6. Steps f-g were carried out in the same manner as steps f-g in example 1. MS (ESI) [M+H]⁺: 416.37; ¹H NMR (400 MHz, CDCl₃) δ 7.30 (d, J=8.1 Hz, 2H), 7.10 (d, J=8.1 Hz, 2H), 7.00 (dd, J=8.4, 1.5 Hz, 1H), 6.83 (d, J=8.1 Hz, 2H), 4.10 (q, J=6.8 Hz, 1H), 3.43 (dt, J=14.6, 7.4 Hz, 1H), 3.30 (s, 3H), 2.42 (s, 3H), 2.33 (s, 3H), 1.87-1.76 (m, 1H), 1.75-1.46 (m, 7H), 0.96 (d, J=6.8 Hz, 3H).

Example 33

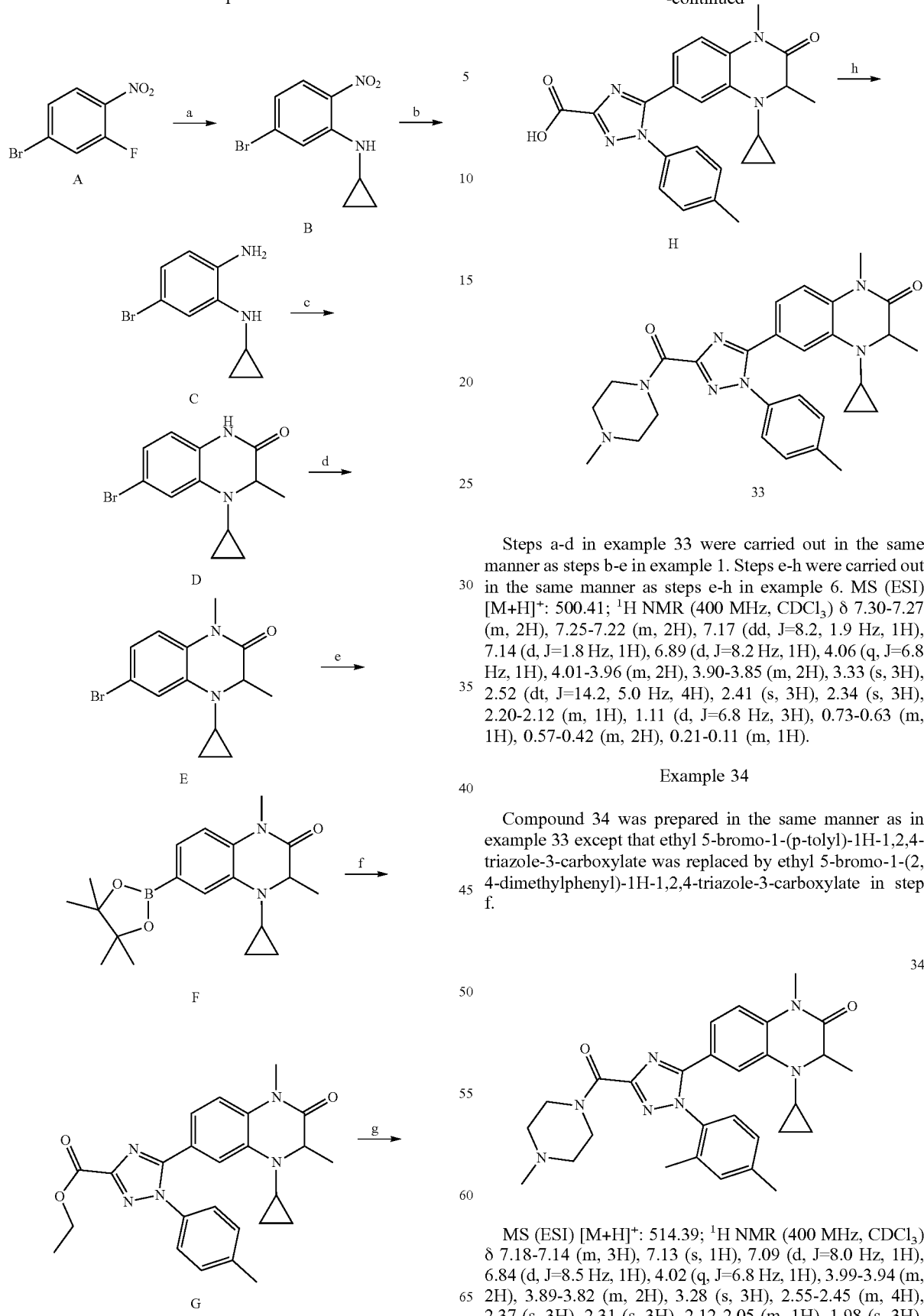

Steps a-d in example 33 were carried out in the same manner as steps b-e in example 1. Steps e-h were carried out in the same manner as steps e-h in example 6. MS (ESI) [M+H]+: 500.41; ¹H NMR (400 MHz, CDCl₃) δ 7.30-7.27 (m, 2H), 7.25-7.22 (m, 2H), 7.17 (dd, J=8.2, 1.9 Hz, 1H), 7.14 (d, J=1.8 Hz, 1H), 6.89 (d, J=8.2 Hz, 1H), 4.06 (q, J=6.8 Hz, 1H), 4.01-3.96 (m, 2H), 3.90-3.85 (m, 2H), 3.33 (s, 3H), 2.52 (dt, J=14.2, 5.0 Hz, 4H), 2.41 (s, 3H), 2.34 (s, 3H), 2.20-2.12 (m, 1H), 1.11 (d, J=6.8 Hz, 3H), 0.73-0.63 (m, 1H), 0.57-0.42 (m, 2H), 0.21-0.11 (m, 1H).

Example 34

Compound 34 was prepared in the same manner as in example 33 except that ethyl 5-bromo-1-(p-tolyl)-1H-1,2,4-triazole-3-carboxylate was replaced by ethyl 5-bromo-1-(2,4-dimethylphenyl)-1H-1,2,4-triazole-3-carboxylate in step f.

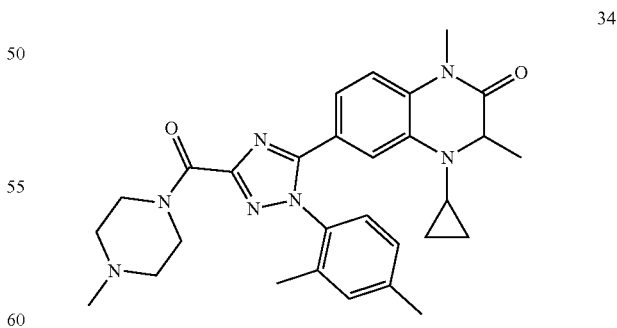

MS (ESI) [M+H]+: 514.39; ¹H NMR (400 MHz, CDCl₃) δ 7.18-7.14 (m, 3H), 7.13 (s, 1H), 7.09 (d, J=8.0 Hz, 1H), 6.84 (d, J=8.5 Hz, 1H), 4.02 (q, J=6.8 Hz, 1H), 3.99-3.94 (m, 2H), 3.89-3.82 (m, 2H), 3.28 (s, 3H), 2.55-2.45 (m, 4H), 2.37 (s, 3H), 2.31 (s, 3H), 2.12-2.05 (m, 1H), 1.98 (s, 3H), 1.07 (d, J=6.8 Hz, 3H), 0.70-0.62 (m, 1H), 0.55-0.45 (m,

2H), 0.19-0.11 (m, 1H); $^{13}$C NMR (126 MHz, CDCl$_3$) δ 168.76, 160.66, 156.77, 155.07, 140.46, 135.75, 135.08, 134.91, 132.11, 131.22, 127.92, 127.44, 122.28, 120.10, 114.33, 113.64, 58.07, 55.43, 54.68, 47.05, 46.03, 42.41, 29.04, 27.79, 21.28, 17.63, 12.17, 9.13, 6.63.

Example 35

Compound 35 was prepared in the same manner as in example 33 except that ethyl 5-bromo-1-(p-tolyl)-1H-1,2,4-triazole-3-carboxylate was replaced by ethyl 5-bromo-1-(2,4-dimethylphenyl)-1H-1,2,4-triazole-3-carboxylate in step f and N-methylpiperazine was replaced by 1-ethylpiperazine in step h.

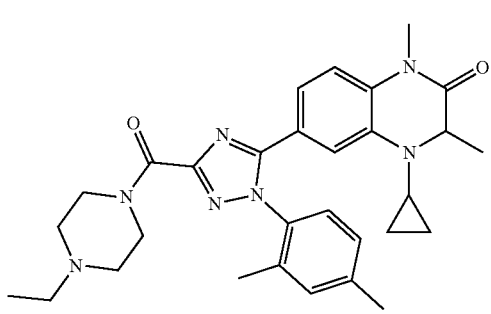

35

MS (ESI) [M+H]$^+$: 528.43; $^1$H NMR (400 MHz, CDCl$_3$) δ 7.19-7.12 (m, 4H), 7.10 (d, J=8.1 Hz, 1H), 6.84 (d, J=8.2 Hz, 1H), 4.06-3.97 (m, 3H), 3.90-3.85 (m, 2H), 3.29 (s, 3H), 2.58-2.52 (m, 4H), 2.47 (q, J=7.2 Hz, 2H), 2.37 (s, 3H), 2.13-2.05 (m, 1H), 1.98 (s, 3H), 1.12-1.04 (m, 6H), 0.71-0.62 (m, 1H), 0.56-0.45 (m, 2H), 0.20-0.10 (m, 1H); $^{13}$C NMR (151 MHz, CDCl$_3$) δ 168.76, 160.58, 156.76, 155.08, 140.46, 135.74, 135.06, 134.90, 132.11, 131.21, 127.93, 127.44, 122.27, 120.10, 114.34, 113.63, 58.08, 53.23, 52.38, 52.31, 47.04, 42.39, 29.04, 27.79, 21.29, 17.65, 12.17, 11.85, 9.12, 6.63.

Example 36

The following compound was prepared in the same manner as in example 33 except that N-methylpiperazine was replaced by cis-2,6-dimethylpiperazine in step h.

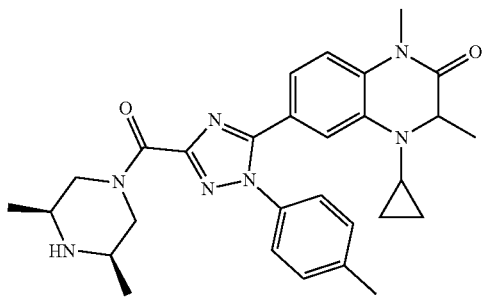

B1

MS (ESI) [M+H]$^+$: 514.29; $^1$H NMR (400 MHz, DMSO-d$_6$) δ 7.38 (d, J=1.0 Hz, 4H), 7.19-7.04 (m, 3H), 4.51 (d, J=13.0 Hz, 1H), 4.29 (s, 1H), 4.00-3.94 (m, 1H), 3.25 (d, J=1.0 Hz, 3H), 2.98 (s, 3H), 2.40 (s, 3H), 2.18 (dt, J=6.7, 3.5 Hz, 1H), 1.24 (s, 1H), 1.14 (d, J=6.3 Hz, 3H), 1.05 (s, 3H), 1.02 (dd, J=6.9, 1.6 Hz, 4H), 0.69-0.64 (m, 1H), 0.55-0.50 (m, 1H), 0.45-0.34 (m, 1H).

Example 37

The following compound was prepared in the same manner as in example 12 except that cyclopentanone was replaced by acetone in step c.

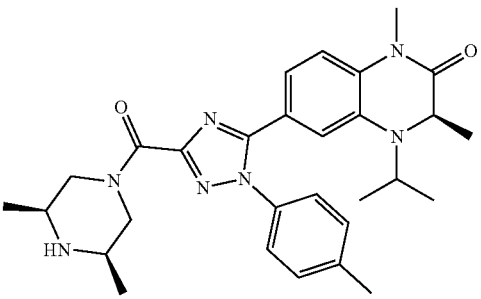

B2

MS (ESI) [M+H]$^+$: 516.23; $^1$H NMR (400 MHz, Chloroform-d) δ 7.32-7.29 (m, 4H), 7.05 (d, J=8.3 Hz, 1H), 6.96 (s, 1H), 6.91 (d, J=8.4 Hz, 1H), 4.95-4.86 (m, 2H), 4.18 (q, J=6.8 Hz, 1H), 3.58 (p, J=6.6 Hz, 1H), 3.37 (s, 3H), 3.32-3.21 (m, 2H), 3.13-2.97 (m, 2H), 2.45 (s, 3H), 1.59-1.54 (m, 3H), 1.52-1.44 (m, 3H), 1.16 (d, J=6.5 Hz, 3H), 1.13 (d, J=6.6 Hz, 3H), 1.07 (d, J=6.8 Hz, 3H).

Example 38

The following compound was prepared in the same manner as in example 12 except that cyclopentanone was replaced by 3-oxacyclobutanone in step c.

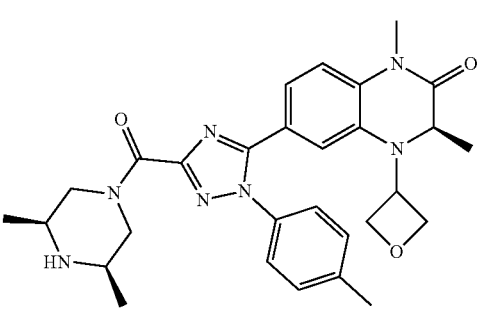

B3

MS (ESI) [M+H]$^+$: 530.3; $^1$H NMR (400 MHz, Chloroform-d) δ 7.30 (m, 4H), 7.25-7.15 (m, 1H), 7.00 (d, J=8.4 Hz, 1H), 6.22 (d, J=7.3 Hz, 1H), 4.84 (d, J=13.6 Hz, 1H), 4.72 (d, J=6.3 Hz, 2H), 4.36-4.25 (m, 2H), 4.23-4.13 (m, 1H), 3.92 (q, J=6.9 Hz, 1H), 3.41 (s, 3H), 3.27 (m, 3H), 2.88 (s, 1H), 2.45 (s, 3H), 1.44 (d, J=6.0 Hz, 3H), 1.37 (s, 3H), 1.30-1.23 (m, 1H), 0.97 (d, J=6.8, 1.6 Hz, 3H).

Example 39

The following compound was prepared in the same manner as in example 12 except that cyclopentanone was replaced by tetrahydropyranone in step c.

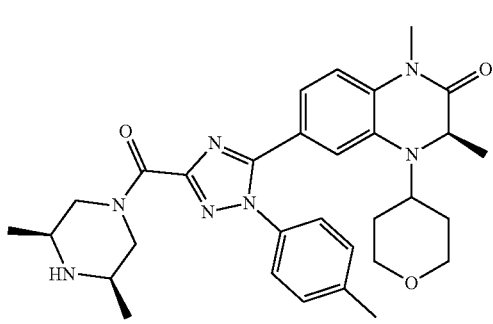

B4

MS (ESI) [M+H]⁺: 558.3; ¹H NMR (400 MHz, Chloroform-d) δ 7.36-7.26 (m, 4H), 7.22 (d, J=8.5 Hz, 1H), 6.99 (d, J=8.3 Hz, 1H), 6.92-6.85 (m, 1H), 4.85-4.77 (m, 2H), 4.13 (q, J=6.8 Hz, 1H), 3.97 (d, J=11.5 Hz, 2H), 3.38 (s, 3H), 3.32-3.21 (m, 6H), 2.78 (s, 1H), 2.45 (s, 3H), 1.80-1.72 (m, 1H), 1.66-1.61 (m, 2H), 1.36 (s, 3H), 1.31-1.24 (m, 5H), 1.05 (d, J=6.8 Hz, 3H).

Example 40

The following compound was prepared in the same manner as in example 12 except that cyclopentanone was replaced by 4,4-difluorocyclohexanone in step c.

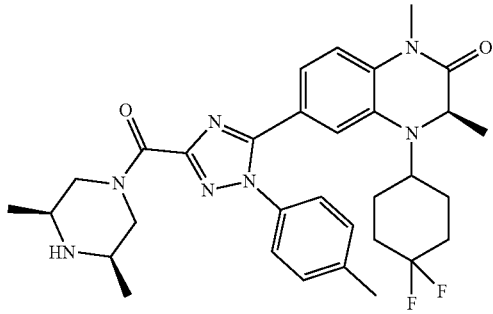

B5

MS (ESI) [M+H]⁺: 592.3; ¹H NMR (400 MHz, Chloroform-d) δ 7.33 (d, J=1.0 Hz, 4H), 7.23 (d, J=8.4 Hz, 1H), 7.03-6.94 (m, 1H), 6.87 (s, 1H), 4.92-4.83 (m, 2H), 4.11-4.06 (m, 1H), 3.39 (s, 3H), 3.35-3.30 (m, 3H), 3.17-3.12 (m, 1H), 2.46 (s, 3H), 2.18-2.11 (m, 3H), 1.88-1.71 (m, 2H), 1.64 (m, 5H), 1.53-1.47 (m, 3H), 1.46-1.39 (m, 3H), 1.06 (d, J=6.8 Hz, 3H).

Example 41

The following compound was prepared in the same manner as in example 12 except that cyclopentanone was replaced by 3,3-difluorocyclobutanone in step C.

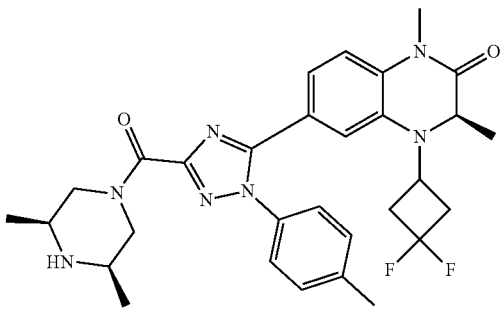

B6

MS (ESI) [M+H]⁺: 563.3; ¹H NMR (400 MHz, Chloroform-d) δ 7.36-7.26 (m, 4H), 7.22 (d, J=8.4 Hz, 1H), 7.02-6.93 (m, 1H), 6.86 (s, 1H), 4.92-4.83 (m, 2H), 4.11-4.05 (m, 1H), 3.38 (s, 3H), 3.34-3.30 (m, 3H), 3.17-3.12 (m, 1H), 2.46 (s, 3H), 2.18-2.11 (m, 3H), 1.88-1.71 (m, 2H), 1.64 (m, 2H), 1.53-1.47 (m, 2H), 1.45-1.37 (m, 3H), 1.05 (d, J=6.8 Hz, 3H).

Example 42

The compound was prepared in the same manner as in example 12 except that cyclopentanone was replaced by tert-butyl 2-oxo-7-azaspiro[3.5]nonane-7-carboxylate in step c.

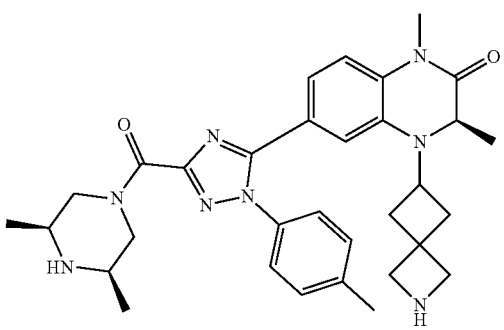

B7

MS (ESI) [M+H]⁺: 568.3; ¹H NMR (400 MHz, Chloroform-d) δ 7.38-7.30 (m, 4H), 7.26-7.15 (m, 1H), 7.01 (d, J=8.4 Hz, 1H), 6.24 (d, J=7.2 Hz, 1H), 4.85 (d, J=13.5 Hz, 1H), 4.82 (m, 2H), 4.36-4.28 (m, 2H), 4.32-4.18 (m, 1H), 3.90 (q, J=6.9 Hz, 1H), 3.58-3.48 (m, 4H), 3.41 (s, 3H), 3.27 (m, 2H), 2.88 (s, 1H), 2.45 (s, 3H), 1.85-1.72 (m, 4H), 1.44 (d, J=6.0 Hz, 3H), 1.37 (s, 3H), 0.97 (d, J=6.8, 1.6 Hz, 3H).

Example 43

The compound was prepared in the same manner as in example 12 except that cyclopentanone was replaced by 2-oxo-spiro[3.3]heptan-6-one in step c.

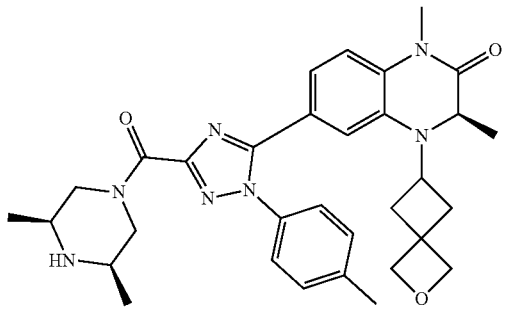

B8

MS (ESI) [M+H]+: 569.3; 1H NMR (400 MHz, Chloroform-d) δ 7.36-7.30 (m, 4H), 7.25-7.15 (m, 1H), 7.00 (d, J=8.5 Hz, 1H), 6.22 (d, J=7.3 Hz, 1H), 4.80 (d, J=13.6 Hz, 1H), 4.45 (d, J=6.3 Hz, 2H), 4.23-4.13 (m, 1H), 4.12-4.01 (m, 2H), 3.88 (q, J=6.9 Hz, 1H), 3.41 (s, 3H), 3.27 (m, 3H), 2.88 (s, 1H), 2.45 (s, 3H), 1.88-1.76 (m, 4H), 1.44 (d, J=6.0 Hz, 3H), 1.37 (s, 3H), 1.30-1.23 (m, 2H), 0.97 (d, J=6.8, 1.6 Hz, 3H).

Example 44

Reagents and conditions: a); b); c) bis(pinacolato)diboron, potassium acetate, dioxane, [1,1'-bis(diphenylphosphino)ferrocene] palladium dichloride dichloromethane complex, refluxed at 120° C. overnight; d) lithium hydroxide, THF, H2O, room temperature, 12 hours; e) HATU, DMF, cis-2,6-dimethylpiperazine, DIPEA, reacted at room temperature overnight; f) sodium bicarbonate, THF, [1,1'-bis(diphenylphosphino)ferrocene]palladium dichloride dichloromethane complex, refluxed at 80° C. overnight.

a) A (300 mg, 1.18 mmol) was dissolved in 20 mL of anhydrous dichloromethane, stirred at room temperature for 5 min, then 4-dimethylaminopyridine (216 mg, 1.17 mmol) was added and stirred for another 5 min. Then cyclopropylcarbonyl chloride (214 μL, 2.36 mmol) was added, then stirred at room temperature for 2 h. The organic phase was evaporated and purified by column chromatography to give 309 mg of product, yield 84%.

MS (ESI) [M+H]+: 309.1; 1H NMR (400 MHz, DMSO-d6) δ 10.87 (s, 1H), 7.67 (d, J=2.1 Hz, 1H), 7.40 (dd, J=8.3, 2.1 Hz, 1H), 7.00 (d, J=8.5 Hz, 1H), 5.06 (q, J=7.2 Hz, 1H), 1.99 (d, J=5.7 Hz, 1H), 1.10 (d, J=7.2 Hz, 3H), 1.06 (m, 1H), 1.02-0.95 (m, 1H), 0.88 (m, 1H), 0.80 (m, J=7.9 Hz, 1H).

b) B (300 mg, 0.97 mmol) was dissolved in 15 mL of anhydrous dichloromethane, stirred at room temperature for 5 min, then sodium hydride (28 mg, 1.16 mmol) was added, and stirred for 20 min, then iodomethane (66 μL, 1.07 mmol) was added and stirred at room temperature for 1 hour. The organic phase was evaporated and purified by column chromatography to give 237 mg of product, yield 76%.

MS (ESI) [M+H]+: 323.2; 1H NMR (400 MHz, Chloroform-d) δ 7.60 (s, 1H), 7.34 (dt, J=8.7, 2.3 Hz, 1H), 6.95 (dd, J=8.7, 1.5 Hz, 1H), 5.37 (d, J=7.4 Hz, 1H), 3.33 (s, 3H), 1.93-1.85 (m, 1H), 1.32-1.25 (m, 1H), 1.15 (d, J=7.4 Hz, 3H), 1.01 (td, J=8.2, 7.7, 3.5 Hz, 2H), 0.81-0.73 (m, 1H).

c) C (80 mg, 0.25 mmol), bis(pinacolato)diboron (70 mg, 0.28 mmol) and potassium acetate (49 mg, 0.5 mmol) were dissolved in 2 mL of anhydrous dioxane, argon gas was ventilated for 10 minutes, and then [1,1'-bis(diphenylphosphino)ferrocene]palladium dichloride dichloromethane complex (9 mg, 0.012 mmol) was added and argon gas was ventilated for another 2 minutes. Then the mixture was heated to 120° C. and refluxed overnight under argon atmosphere. The reaction was monitored by TLC plate. After the reaction was completed, the mixture was extracted with

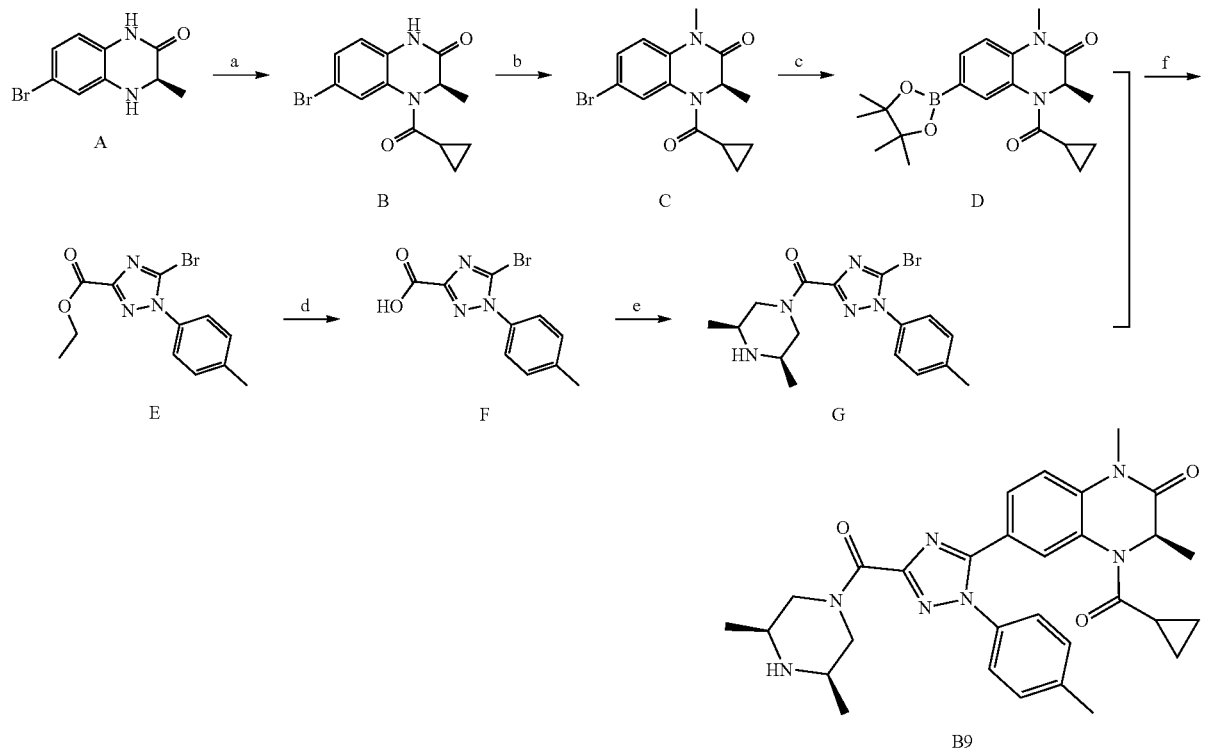

ethyl acetate, washed with saturated brine, and dried over anhydrous sodium sulfate. The organic phase was purified by silica gel column chromatography and eluted with gradient dichloromethane/methanol (0-2%) to give 67 mg of beige solid D was obtained in a yield of 73%.

d) E (0.31 g, 1 mmol) and lithium hydroxide (0.168 g, 4 mmol) were dissolved in 6 mL mixed solvent of THF and H₂O (4:1), then reacted at room temperature for 12 hours. The reaction was monitored by TLC plate. After the reaction was completed, the mixture was adjusted to pH 5-6 with 1 M HCl, extracted with ethyl acetate (20 mL*2) and 20 mL of water. The organic layers were combined and re-extracted once with 20 mL saturated brine. The organic phase was dried over anhydrous sodium sulfate, filtrated, directly dried by rotary evaporation to give 0.28 g white powder F, yield 99%.

e) Compound F (0.28 g, 1 mmol) was dissolved in 5 mL of DMF, then HATU (0.38 g, 1 mmol) was added and reacted at room temperature for half an hour, then cis-2,6-dimethylpiperazine (0.144 mL, 1 mmol) and DIPEA (0.165 mL, 1 mmol) were added and reacted at room temperature overnight. The reaction was monitored by TLC plate. After the reaction was completed, the mixture was extracted with ethyl acetate (20 mL*2) and 60 mL of saturated sodium bicarbonate. The organic layers were combined and washed once with 40 mL saturated brine. The organic phase was dried over anhydrous sodium sulfate, purified by silica gel column chromatography and eluted with gradient methanol/dichloromethane (0-5%) to give 0.25 g of pink solid G, yield 66%.

f) D (70 mg, 0.19 mmol), G (78 mg, 0.2 mmol) and a saturated solution of sodium bicarbonate (32 mg, 0.38 mmol) were dissolved in 1 mL of THF, argon gas was ventilated for 10 min, [1,1'-bis(diphenylphosphino)ferrocene]palladium dichloride dichloromethane complex (14 mg, 0.019 mmol) was added and then argon gas was ventilated for another 2 minutes. The mixture was heated to 80° C. and refluxed overnight under argon atmosphere and then the solvent was evaporated. The reaction was monitored by TLC plate. After the reaction was completed, the mixture was extracted with ethyl acetate, washed with saturated brine and dried over anhydrous sodium sulfate. The organic phase was purified by silica gel column chromatography and eluted with gradient dichloromethane/methanol (0-5%) to give 40 mg of light brown solid 9, yield 39%.

MS (ESI) [M+H]⁺: 542.3; ¹H NMR (400 MHz, Chloroform-d) δ 7.64 (s, 1H), 7.48 (s, 2H), 7.33-7.21 (m, 3H), 7.14 (s, 1H), 5.47 (s, 1H), 4.86 (s, 2H), 3.41 (s, 3H), 3.38-3.19 (m, 2H), 3.01 (s, 1H), 2.43 (s, 3H), 1.49 (d, J=27.8 Hz, 6H), 1.27 (s, 3H), 1.15 (s, 3H), 0.84 (s, 2H), 0.70-0.41 (m, 2H).

Example 45

The compound was prepared in the same manner as in example 44 except that cyclopropylcarbonyl chloride was replaced by propionyl chloride in step a.

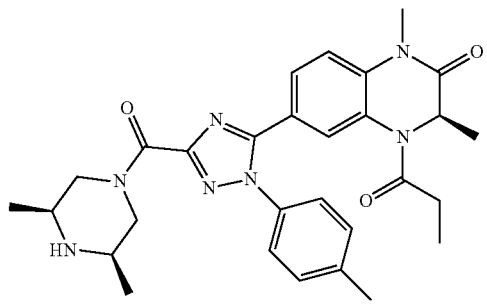

B10

MS (ESI) [M+H]⁺: 530.4; 1H NMR (400 MHz, Chloroform-d) δ 7.49-7.56 (m, 2H), 7.32 (s, 4H), 7.14-7.09 (m, 1H), 4.87 (d, J=14.2 Hz, 2H), 4.13 (q, J=7.2 Hz, 1H), 3.38 (s, 3H), 3.36-2.85 (m, 2H), 2.46 (s, 3H), 1.62-1.32 (m, 7H), 1.31-1.24 (m, 1H), 1.24-0.87 (m, 8H).

Example 46

The compound was prepared in the same manner as in example 44 except that cyclopropylcarbonyl chloride was replaced by isobutyryl chloride in step a.

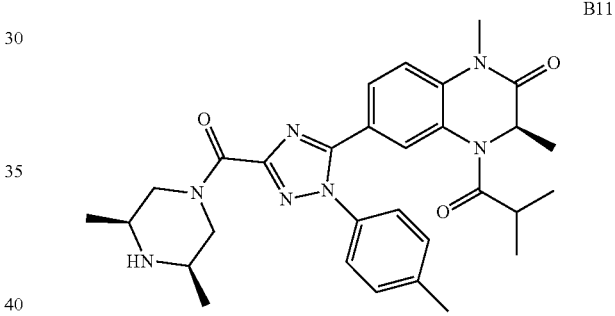

B11

MS (ESI) [M+H]⁺: 544.3; ¹H NMR (400 MHz, Chloroform-d) δ 7.52-7.47 (m, 4H), 7.35-7.24 (m, 2H), 7.11 (d, J=9.5 Hz, 1H), 4.87 (d, J=13.3 Hz, 2H), 4.14 (q, J=7.2 Hz, 1H), 3.52-3.18 (m, 7H), 3.11-2.86 (m, 1H), 2.48-2.42 (m, 4H), 1.51 (d, J=7.8 Hz, 3H), 1.44 (s, 3H), 1.35-1.21 (m, 1H), 1.23-0.77 (m, 8H).

Example 47

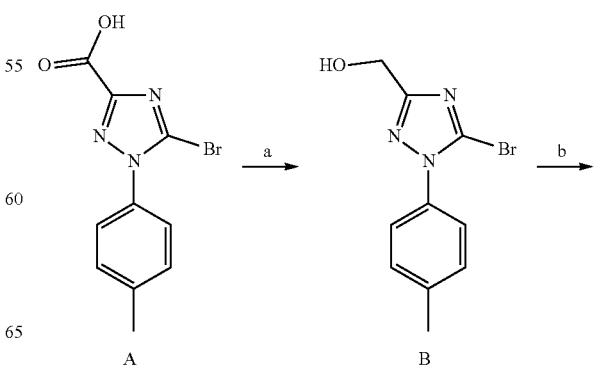

-continued

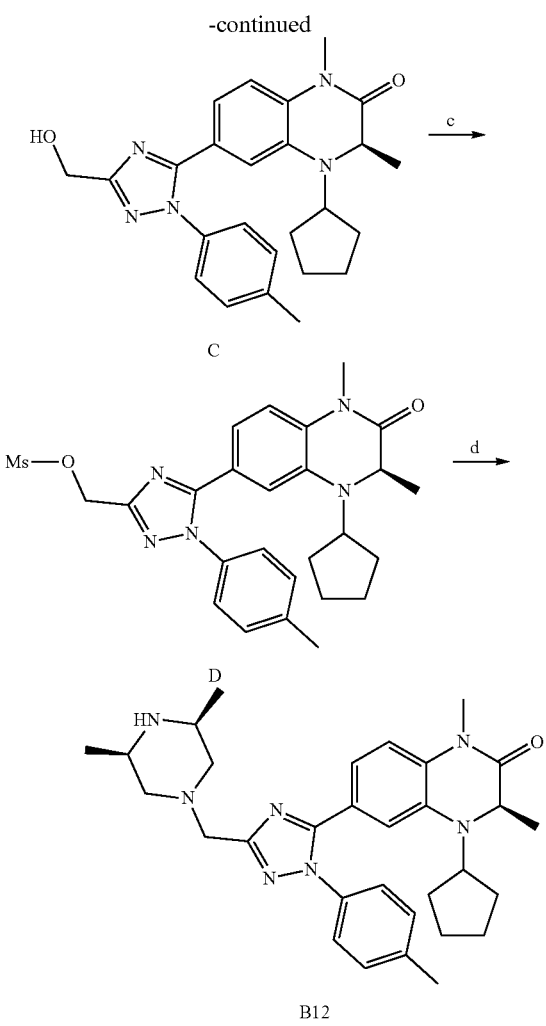

Reagents and conditions: a) sodium borohydride, THF, tetrahydrofuran, room temperature, 2 hours; b) Intermediate F in example 6, sodium bicarbonate, THF, [1,1'-bis(diphenylphosphino)ferrocene]palladium dichloride dichloromethane complex, refluxed at 80° C. overnight; c) methanesulfonyl chloride, triethylamine, dichloromethane, room temperature, 1 hour; d) cis-2,6-dimethylpiperazine, N,N-diisopropylethylamine, DMF, 60° C., overnight.

a) A (500 mg, 1.61 mmol) was dissolved in 20 mL tetrahydrofuran/methanol (1:1) and sodium borohydride (306 mg, 8.05 mmol) was added and stirred at room temperature for 2 h. Water was added and the mixture was adjusted to pH 6-7 with 1N NaOH, extracted with ethyl acetate, washed with saturated brine, and dried over anhydrous sodium sulfate. The organic phase was purified by silica gel column chromatography and eluted with gradient dichloromethane/methanol (0-2%) to give 340 mg of colorless viscous material B, yield 78%.

b) B (200 mg, 0.75 mmol), intermediate F in Example 6 (276 mg, 0.75 mmol) and a saturated solution of sodium bicarbonate (125 mg, 1.49 mmol) were dissolved in 20 mL of THF and argon gas was ventilated for 10 min. [1,1'-bis(diphenylphosphino)ferrocene]palladium dichloride dichloromethane complex (55 mg, 0.075 mmol) was added and argon gas was ventilated for another 2 minutes. The mixture was heated to 80° C. and refluxed overnight under argon atmosphere, and the solvent was evaporated. The reaction was monitored by TLC plate. After the reaction was completed, the mixture was extracted with ethyl acetate, washed with saturated brine, and dried over anhydrous sodium sulfate. The organic phase was purified by silica gel column chromatography and eluted with gradient ethyl acetate/petroleum ether (50-80%) to give 80 mg of light brown solid C, yield 19%.

c) C (60 mg, 0.14 mmol) was dissolved in 2 mL of dichloromethane, triethylamine (38 µL, 0.28 mmol) and methanesulfonyl chloride (16 µL, 0.21 mmol) were added and stirred at room temperature for 1 h. A saturated aqueous solution of sodium bicarbonate was added, and the mixture was extracted with ethyl acetate, washed with saturated brine and dried over anhydrous sodium sulfate. The solvent was evaporated to give 75 mg of brown sticky substance which was directly used for the next reaction without purification.

d) D (75 mg, 0.147 mmol) was dissolved in 2 mL DMF, and cis-2,6-dimethylpiperazine (28 mg, 0.24 mmol) and N,N-diisopropylethylamine (47 µL, 0.285 mmol) were added and stirred at 60° C. overnight. After the reaction was completed, the mixture was extracted with ethyl acetate, washed with saturated brine, and dried over anhydrous sodium sulfate. The organic phase was purified by silica gel column chromatography and eluted with 8% of dichloromethane/methanol to give 36 mg of light brown solid 12, yield 47%.

MS (ESI) [M+H]$^+$: 528.3; $^1$H NMR (400 MHz, Chloroform-d) δ 7.32-7.22 (m, 4H), 7.22-7.17 (m, 1H), 6.94 (d, J=8.4 Hz, 1H), 6.79 (d, J=1.8 Hz, 1H), 4.15 (q, J=6.7 Hz, 1H), 3.84 (s, 2H), 3.52-3.40 (m, 4H), 3.38 (s, 3H), 3.15 (d, J=12.5 Hz, 2H), 2.60 (dt, J=15.9, 12.0 Hz, 2H), 2.41 (s, 3H), 1.87-1.78 (m, 1H), 1.77-1.65 (m, 3H), 1.59-1.49 (m, 8H), 1.34-1.24 (m, 2H), 1.00 (d, J=6.8 Hz, 3H).

Example 48

1. Enzyme Activity Test Method for Bromodomain Recognition Protein BRD4 Inhibitor The binding activity of the compound to BRD4 (I) was tested using a fluorescence anisotropy (FA) method. The principle of FA test is to calculate and analyze the fluorescence polarization values in the horizontal and vertical directions by detecting the change of molecular weight before and after the interaction of fluorescein-labeled small molecules with other molecules. If the equilibrium of the binding between the fluorescently labeled small molecule and macromolecule is established, it will move slowly when excited, and the measured fluorescence polarization value will increase. If the binding between the fluorescently labeled small molecule and the macromolecule is replaced by another ligand, its rotation or flipping speed in the free state will be faster, and the emitted light will be depolarized relative to the plane of the excitation light, and the measured polarized light value will decrease to calculate the fluorescence anisotropy of the sample.

Expression and purification of the BRD4(I) recognition domain: colonies of newly transformed plasmid DNA from E. coli BL21(DE3)-condon plus-RIL cells were cultivated in 50 mL of Terrific Broth medium containing 50 µg/mL kanamycin and 34 µg/mL chloramphenicol at 37° C. overnight (starting culture). The starting culture was then diluted 100-fold in 1 L of fresh TB medium and the cells were grown at 37° C. to an optical density of about 0.8 at OD600 and then the temperature was lowered to 16° C. When the system was equilibrated at 16° C., the optical density at OD600 was approximately 1.2, and protein expression was induced with 0.2 mmol of isopropyl-β-D-thiogalactopyranoside (IPTG) overnight at 16° C. Bacteria were harvested by centrifugation (4000×g, 20 minutes, 4° C.) and stored as a pellet at −80° C. The cells expressing His 6-tagged protein was resuspend in lysis buffer [50 mmol 4-hydroxyethylpiperazineethanesulfonic acid (HEPES), 25° C., pH 7.5, 500 mmol NaCl, 10 mmol imidazole, 5% glycerol and freshly added 0.5 mmol of tris(2-carboxyethyl)phosphine hydrochloride (TCEP) and 1 mmol of phenylmethanesulfonyl fluoride (PMSF)] and lysed at 4° C. using JN 3000PLUS high pressure homogenizer (JNBIO-Guangzhou, China). The lysate was clarified by centrifugation (12,000×g for 1 hour at 4° C.) and applied to a nickel-nitriloacetate agarose column. The column was washed once with 50 mL of wash buffer containing 30 mmol of imidazole. The protein was eluted using imidazole in an elution buffer in a stepwise elution (100-250 mmol imidazole in 50 mmol HEPES, 25° C., pH 7.5, 500 mmol NaCl, 5% glycerol). All fractions were collected and monitored by SDS-polyacrylamide gel electrophoresis (Bio-Rad Criterion TM Precast Gels, 4-12% Bis-Tris, 1.0 mm, from Bio-Rad, CA). After 1 mmol of dithiothreitol (DTT) was added, the eluted proteins were treated with tobacco plaque virus (TEV) protease overnight at 4° C. to remove the His6 tag. The protein was concentrated and further purified by size exclusion chromatography on a Superdex 75 16/60 HiLoad gel filtration column. The samples were monitored by SDS-polyacrylamide gel electrophoresis and concentrated to 8-10 mg/mL with gel filtration buffer, 10 mmol Hepes pH 7.5, 500 mM NaCl, 1 mmol DTT, and used for protein binding assays and crystallization.

The fluorogenic substrate was (+)-JQ1 linked to a fluorescent molecule and the working concentration was 5 nM. BRD4 (I) protein had 10 nM of working concentration and the total reaction system was 40 μL. The buffer was 50 mM 4-hydroxyethylpiperazineethanesulfonic acid (HEPES) pH 7.4, 150 mM NaCl, 0.5 mM 3[(3-cholamidopropyl)dimethylammonio]propanesulfonate (CHAPS). The initial screening concentration of the compound was 1 μM, and the $IC_{50}$ of the compound having an inhibition rate greater than 60% under this condition was determined. The final concentration of DMSO was chosen to be 0.2%, taking into account the solubility of the compound and the effect of DMSO on the assay. All measurements were made under these conditions. After all the components were mixed and reacted away from light at room temperature for 4 hours or at 4° C. overnight, the anisotropy value was measured using Corning's all-black, low-side, 384-well microplate having NBS surface (Cat. No. CLS3575). The test instrument was a BioTek synergy 2 detector with an excitation of 485 nM and an emission of 530 nM. The buffer was used as the blank value for the system reading.

Numerical processing: inhibition rate=$(C-F)/(C-B)×100\%$ (Equation 1)

Wherein, C: anisotropic value of the complete binding of the fluorescent substrate to the protein;
B: fluorescent substrate anisotropy background value
F: anisotropy value at the corresponding concentration of the compound The S curve was taken as the concentration of the compound and the corresponding inhibition rate. The $IC_{50}$ of the corresponding compound was obtained.

The structure of the fluorescent substrate used in BRD4 (I) enzyme activity assay method FA was as follows:

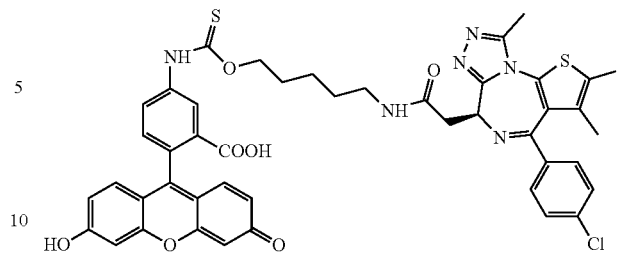

(Note: Fluorescent substrate referred to the product of (+)-JQ1 linked to a fluorescent molecule through a linker)

Pharmacological data: The pharmacological test results of some of the compounds of the present invention were disclosed in Table 1 below, and the control used in the test is a bromodomain recognition protein BRD4 inhibitor (+)-JQ1.

TABLE 1

Enzyme activity test results of bromodomain protein BRD4 inhibitor

| Example | BRD4 (1) $IC_{50}$ (nM) | Example | BRD4 (1) $IC_{50}$ (nM) |
|---|---|---|---|
| 1 | 5.9 | 2 | 9.7 |
| 3 | 15.4 | 4 | 18.4 |
| 6 | 6.5 | 7 | 7.6 |
| 8 | 9.8 | 9 | 8.2 |
| 10 | 4.96 | 11 | 5.08 |
| 12 | 4.9 | 13 | 8.3 |
| 14 | 4.5 | 15 | 4.2 |
| 16 | 4.06 | 17 | 7.4 |
| 18 | 6.5 | 19 | 4.6 |
| 20 | 25.4 | 21 | 7.1 |
| 22 | 8.1 | 23 | 9.2 |
| 24 | 5.3 | 26 | 5.1 |
| 27 | 4.9 | 28 | 6.7 |
| 29 | 7.7 | 32 | 5.1 |
| 33 | 15.7 | 34 | 13.9 |
| 35 | 14.5 | (+)-JQ1 | 27 |
| 36 | 18.5 | 37 | 15.1 |
| 38 | 13.6 | 39 | 10.3 |
| 40 | 16 | 41 | 20.1 |
| 47 | 6.7 | | |

Table 1 showed that the compounds of the present invention had a good inhibitory activity against the BRD4 (I) protein, and the compounds listed in the table have better molecular activities than the positive (+)-JQ1.

2. Cell Activity Test Method for Bromine Domain Recognition Protein BRD4 Inhibitor The MM.1S cell line was tested for cell viability. The test methods were as follows: human myeloma cells MM.1S were treated with compound for 72 h, and the proliferation inhibition effect and degree of the compound were detected by CCK-8 method.

Pharmacological data: The pharmacological test results of some of the compounds of the present invention were disclosed in Table 2 below, and the control used in the test is a bromodomain recognition protein BRD4 inhibitor (+)-JQ1.

TABLE 2

Test results of compounds on MM.1S cell line

| Example | MM.1S IC$_{50}$ (nM) | Example | MM.1S IC$_{50}$ (nM) |
| --- | --- | --- | --- |
| 1 | 4.16 ± 0.05 | 6 | 13.56 ± 5.45 |
| 9 | 22.97 ± 7.42 | 10 | 25.76 ± 0.52 |
| 12 | 5.42 ± 1.14 | 13 | 22.44 ± 1.40 |
| 14 | 10.72 ± 1.71 | 16 | 29.39 ± 9.3 |
| 18 | 10.22 ± 0.02 | 33 | 10.70 ± 2.59 |
| 34 | 9.11 ± 2.91 | 35 | 15.54 ± 7.42 |
| 36 | 3.13 | 37 | 18.18 |
| (+)-JQ1 | 19.33 ± 9.3 | | |

Table 2 showed that the compounds of the present invention had a good inhibitory activity against the MM.1S cell line, especially the compounds of examples 1, 6, 12, 14, 18, 33, 34, 35, 36 and 37 had better inhibitory activity against the MM.1S cell line than the positive (+)-JQ1.

3. Test Method for Metabolic Stability and Enzyme Inhibition Properties of Compounds in Liver Microsomes 3.1 Test Method of Metabolic Stability Test The system which was 150 μl of human liver microsomes (final concentration: 0.5 mg/ml) was used for metabolic stability incubation. The system contained reduced coenzyme II (NADPH) (final concentration: 1 mM) and 1 μM compound, positive control or negative control. The reaction was terminated with acetonitrile containing (imiprozine, batch number: 3221; tinidazole, given) at 0 min, 5 min, 10 min, and 30 min, respectively. The mixture was vortexed for 10 min, centrifuged at 15000 rpm for 10 min, and 50 μl of the supernatant was injected into a 96-well plate. The metabolic stability of the compound was calculated by measuring the relative reduction in the original medicament.

3.2 Test Method of Direct Inhibition Test (DI Test)

The system which was 100 μl of human liver microsomes (final concentration: 0.2 mg/ml) was used for direct inhibition incubation. The system contained NADPH (final concentration: 1 mM), 10 μl compound, positive inhibitor cocktail (ketoconazole, 10 μl, quinidine 10 μl, sulfaphenazole 100 μl, naphthoflavone 10 μl, tranylcypromine 1000 μl), negative control 10 μl DMSO and mixed probe substrate (midazolam 10 μl, testosterone 100 μl, dextromethorphan 10 μl, diclofenac 20 μl, phenacetin 100 μl, mephenytoin 100 μl). The reaction was stopped after the system was incubated for 20 min. The relative activity of the enzyme was calculated by measuring the relative amount of production of the metabolite.

3.3 Test Method of Mechanistic Inhibition Test (TDI Test)

The system which was 200 μl of human liver microsomes (final concentration: 0.2 mg/ml) was used for mechanistic inhibition incubation. The system contained 10 μl compound, mixed positive inhibitor (Troleandomycin 10 μl, Paroxetine 10 μl, Tienilic acid 10 μM, Furafylline 10 μl) or 10 μl negative control PRO. After NADPH (final concentration: 1 mM) or PBS was added, the system was incubated for 0 min, 5 min, 10 min and 30 min, then NADPH (final concentration: 1 mM) and mixed probe substrate (Midazolam 5 μM, Testosterone 50 μl, Dextromethophan 5 μM, Diclofenac 10 μl, Phenacetin 5 0 μM, S-(+)-mephenytoin 50 μl) were added and incubated for 10 min. Then the reaction was stopped. The test for positive inhibitor CYP2C19 was carried out alone, the inhibitor S-(+)-fluoxetine was 100 μM. The enzyme activity was calculated by measuring the relative production amount of metabolite. $k_{obs}$ was calculated.

Pharmacological data: the pharmacological test results of some of the compounds of the present invention were disclosed in Table 3 below.

TABLE 3

Test results of metabolic stability and enzyme inhibition properties in liver microsomes

| Example | HLM Clint (μl/min/mg) | mLM Clint (μl/min/mg) | HLM t$_{1/2}$ (min) | MLM t$_{1/2}$ (min) | Direct inhibition rate (%) | | | | | TDI |
| --- | --- | --- | --- | --- | --- | --- | --- | --- | --- | --- |
| | | | | | 3A4 | 2D6 | 2C9 | 1A2 | 2C19 | |
| 6 | 61 | 34 | 23 | 41 | 22/31 | 3 | 30 | no | 19 | no |
| 8 | 58 | 62 | 23.9 | 22.35 | 5/6 | no | no | no | 35 | no |
| 12 | 52 | 7 | 27 | 193 | 23//28 | 4 | 28 | no | 12 | no |
| 26 | 66 | 52 | 21 | 27 | 35/37 | 4 | 39 | no | 34 | no |
| 27 | 55 | 6 | 25 | 248 | 24/47 | 6 | 27 | no | 19 | no |
| 33 | 22 | 13 | 62 | 107 | 7/12 | no | 6 | 2 | 17 | no |

HLM Clint (μl/min/mg) refers to the clearance rate of compounds in human liver microsomes having a unit of μl/min/mg; mLM Clint (μl/min/mg) refers to the clearance rate of compounds in mouse liver microsomes having a unit of μl/min/mg; HLM t$_{1/2}$ (min) refers to the half-life of the compound in human liver microsomes having a unit of minutes; mLM t$_{1/2}$ (min) refers to the half-life of the compound in mouse liver microsomes having a unit of minutes. TDI means that the mechanism inhibition test of compounds on CYP enzyme evaluates whether the compound has time-dependent inhibition of the enzyme. If the calculated $k_{obs}$ is greater than 200, it is indicated that the compound has a mechanism inhibition against the enzyme.

Table 3 showed that the compounds of the present invention were highly stable in human and mouse liver microsomes, especially compounds 12 and 27 were very stable in mouse liver microsomes, with half-lives of 193 minutes and 248 minutes. Moreover, such compounds had no direct inhibition or mechanism inhibition on CYP450 enzyme.

4. Test Method for Inhibitory Effects of Compounds on the Growth of MM.1S Nude Mice Xenografts In Vivo Balb/C nude mice (6 weeks, female, Beijing Huafukang Biotechnology Co., Ltd.) were purchased, and the animals were conditioned for about one week before the test. MM.1S cells were cultured in vitro, and the cells in logarithmic growth phase were resuspended in serum-free RPMI1640 medium to adjust the cell concentration. The cell suspension was subcutaneously injected into forefoot armpit of the Balb/C nude mice with a syringe, and each animal was injected with 150 μL (8.0×10$^6$/mouse). When the average tumor volume grew to about ~150 mm$^3$, the animals were divided into 4 groups containing solvent control group, 50 mg/kg OTX-015 group, and 20 and 50 mg/kg compound 6 groups by the randomized block method and each group contained six animals. After divided into groups, the animals were administered for 19 days. During the administration period, the tumor diameter was measured twice a week, the body weight of the animals was weighed, the living state of the animals was observed, and abnormal conditions were recorded.

The formula for calculating tumor volume (TV): TV=½× a×b², where a and b represent length and width, respectively.

The relative tumor volume (RTV) was calculated based on the measured results, and the calculation formula was: $RTV=V_t/V_0$. Wherein $V_0$ was the measured tumor volume at the time of administration by cage (ie, $d_0$), and $V_t$ was the tumor volume at each measurement.

The relative tumor proliferation rate T/C (%) was calculated based on the measured results, and the calculation formula was as follows: T/C (%)=($T_{RTV}/C_{RTV}$)×100%, TRTV: treatment group RTV; CRTV: negative control group RTV. OTX-015 is a novel BRD2/3/4 inhibitor with antiproliferative activity against some B cell tumor cell lines and has an $IC_{50}$ of 192 nM on DLBCL cells.

Pharmacological data: The in vivo efficacy results of compound 6 were disclosed in Table 4 below.

TABLE 4

| | | | In vivo efficacy results | | | | |
|---|---|---|---|---|---|---|---|
| | | | Number of animals | TV (mm³, mean) | | RTV (mean | T/C |
| Group | Dose mode of administration | | $d_0$ $d_{14}$ | $d_0$ | $d_{14}$ | SD) | (%) |
| Solvent control | 0.2 ml/20 g qd/14 | po | 12  12 | 186.73 | 2056.97 | 1208.8 | |
| OTX-015 | 50 mg/kg qd/14 | po | 6   6 | 184.48 | 886.75 | 603.15 | 49.90 |
| 6 | 20 mg/kg qd/14 | po | 6   6 | 184.28 | 1024.45 | 584.14 | 48.32 |
| | 50 mg/kg qd/14 | po | 6   6 | 185.34 | 660.39 | 417.16 | 34.51 |

Table 4 showed that compound 6 had a significant inhibitory effect on the growth of MM.1S nude mice xenografts in vivo by oral administration of 50 mg/kg per day.

All documents mentioned in the present application are incorporated herein by reference, just as each document is cited separately as a reference. In addition, it should be understood that various modifications and changes may be made by those skilled in the art after reading the above teachings of the present invention. These equivalent forms are also within the scope defined by the claims appended hereto.

The invention claimed is:

1. A compound of the formula (I), or a stereoisomer, prodrug, solvate, hydrate, crystal form or pharmaceutically acceptable salt thereof:

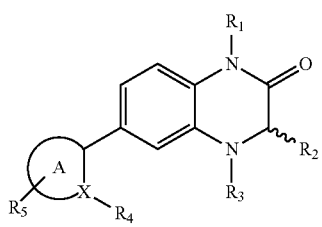

(I)

wherein, $R_1$, $R_2$ and $R_3$ are each independently hydrogen, substituted or unsubstituted C1-C6 alkyl, substituted or unsubstituted C1-C6 alkoxy, substituted or unsubstituted C3-C10 cycloalkyl, substituted or unsubstituted 3-8-membered heterocyclyl, substituted or unsubstituted —C(═O)$R_x$ or substituted or unsubstituted benzyl; wherein $R_x$ is C1-C6 alkyl, C1-C6 alkoxy or C3-C10 cycloalkyl;

the wavy line indicates that the configuration is R type, S type or racemate;

A ring is 5-10 membered heteroaryl, 5-8 membered heterocyclyl, or C6-C10 aryl;

X is C or N;

$R_4$ is substituted or unsubstituted C6-C20 aryl, substituted or unsubstituted benzyl, 5-10 membered heterocyclyl or 5-10 membered heteroaryl;

$R_5$ is absent, hydrogen, substituted or unsubstituted C1-C6 alkyl,

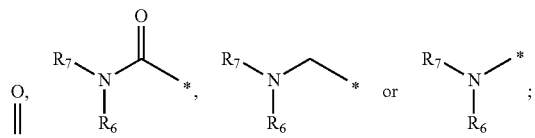

wherein $R_6$ and $R_7$ are each independently hydrogen, substituted or unsubstituted C1-C6 alkyl, substituted or unsubstituted C3-C10 cycloalkyl, substituted or unsubstituted C6-C20 aryl, substituted or unsubstituted benzyl, substituted or unsubstituted 5-10 membered heterocyclyl or substituted or unsubstituted 5-10 membered heteroaryl; or $R_6$ and $R_7$ together with the nitrogen atom to which they are attached form substituted or unsubstituted 5-15 membered heterocyclyl;

the substitution means that there is one or more substituents selected from the group consisting of halogen, hydroxy, nitro, cyano, tert-butoxycarbonyl, C1-C6 alkyl, C1-C6 alkoxy, C3-C10 cycloalkyl and $NR_8R_9$; $R_8$ and $R_9$ are each independently hydrogen, C1-C6 alkyl, C3-C10 cycloalkyl, benzyloxycarbonyl (Cbz), tert-butoxycarbonyl (Boc), fluorenylmethoxycarbonyl (Fmoc), methoxycarbonyl, ethoxycarbonyl, phthaloyl (Pht), p-toluenesulfonyl (Tos), trifluoroacetyl (Tfa), pivaloyl, benzoyl, trityl (Trt), 2,4-dimethoxybenzyl (Dmb), p-methoxybenzyl (PMB) or benzyl (Bn).

2. The compound of the formula (I), or the stereoisomer, prodrug, solvate, hydrate, crystal form or pharmaceutically acceptable salt thereof according to claim 1:

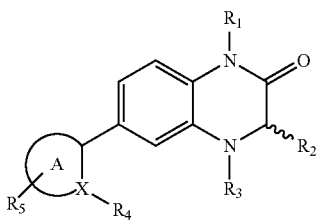

wherein,

R₁, R₂ and R₃ are each independently hydrogen, substituted or unsubstituted C1-C6 alkyl, substituted or unsubstituted C1-C6 alkoxy, substituted or unsubstituted C3-C10 cycloalkyl or substituted or unsubstituted benzyl;

the wavy line indicates that the configuration is R type, S type or racemate;

A ring is 5-10 membered heteroaryl, 5-8 membered heterocyclyl, or C6-C10 aryl;

X is C or N;

R₄ is substituted or unsubstituted C6-C20 aryl, substituted or unsubstituted benzyl, 5-10 membered heterocyclyl or 5-10 membered heteroaryl;

R₅ is absent, hydrogen, substituted or unsubstituted C1-C6 alkyl,

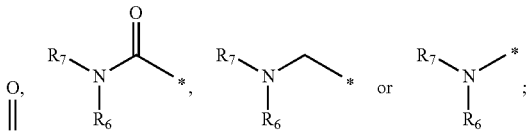

wherein R₆ and R₇ are each independently hydrogen, substituted or unsubstituted C1-C6 alkyl, substituted or unsubstituted C3-C10 cycloalkyl, substituted or unsubstituted C6-C20 aryl, substituted or unsubstituted benzyl, substituted or unsubstituted 5-10 membered heterocyclyl, or substituted or unsubstituted 5-10 membered heteroaryl; or, R₆ and R₇ together with the nitrogen atom to which they are attached form substituted or unsubstituted 5-15 membered heterocyclyl;

the substitution means that there is one or more substituents selected from the group consisting of halogen, hydroxy, nitro, cyano, tert-butoxycarbonyl, C1-C6 alkyl, C1-C6 alkoxy, C3-C10 cycloalkyl and NR₈R₉;

R₈ and R₉ are each independently hydrogen, C1-C6 alkyl, C3-C10 cycloalkyl, benzyloxycarbonyl (Cbz), tert-butoxycarbonyl (Boc), fluorenylmethoxycarbonyl (Fmoc), methoxycarbonyl, ethoxycarbonyl, phthaloyl (Pht), p-toluenesulfonyl (Tos), trifluoroacetyl (Tfa), pivaloyl, benzoyl, trityl (Trt), 2,4-dimethoxybenzyl (Dmb), p-methoxybenzyl (PMB) or benzyl (Bn).

3. The compound according to claim 1, wherein A ring is C6-C10 aryl, 5-6 membered heterocyclyl or 5-6 membered heteroaryl;

R₁ is hydrogen, substituted or unsubstituted C1-C4 alkyl, or substituted or unsubstituted C1-C4 alkoxy, the substituent is halogen, hydroxyl, amino, nitro or cyano;

R₂ is substituted or unsubstituted C1-C4 alkyl, substituted or unsubstituted C1-C4 alkoxy, the substituent is halogen, hydroxyl, amino, nitro or cyano;

R₃ is substituted or unsubstituted C1-C4 alkyl, substituted or unsubstituted C1-C4 alkoxy, substituted or unsubstituted C3-C6 cycloalkyl, substituted or unsubstituted 3-8 membered heterocyclyl, substituted or unsubstituted —C(=O)Rₓ or substituted or unsubstituted benzyl, wherein Rx is C1-C6 alkyl, C1-C6 alkoxy or C3-C6 cycloalkyl, the substituent is selected from the group consisting of halogen, hydroxy, amino, nitro, cyano, C1-C3 alkyl and C1-C3 alkoxy;

R₄ is substituted or unsubstituted C6-C14 aryl, substituted or unsubstituted benzyl, substituted or unsubstituted group having 1-3 heteroatoms selected from N, O or S as follows: 5-8 membered heterocyclyl or 5-8 membered heteroaryl; the substitution means that there is 1-3 substituents, each of which is independently: halogen, hydroxy, amino, nitro, cyano, C1-C4 alkyl or C1-C4 alkoxy;

R₅ is absent, hydrogen, substituted or unsubstituted C1-C4 alkyl,

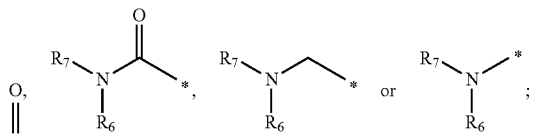

wherein R₆ and R₇ are each independently hydrogen, substituted or unsubstituted C1-C4 alkyl, substituted or unsubstituted C3-C8 cycloalkyl, substituted or unsubstituted C6-C14 aryl, substituted or unsubstituted benzyl, substituted or unsubstituted group having 1-3 heteroatoms selected from N, O or S as follows: 5-8 membered heterocyclyl and 5-8 membered heteroaryl; the substitution means that there is 1-3 substituents, each of which is independently: halogen, hydroxy, amino, methylamino, cyano, N(C1-C4 alkyl)(C1-C4 alkyl), C1-C4 alkyl or C1-C4 alkoxy;

or R₆ and R₇ together with the nitrogen atom to which they are attached form substituted or unsubstituted 5-10 membered heterocyclyl containing 1-3 heteroatoms selected from N, O, S; the substitution means that there is 1-3 substituents, each of which is independently halogen, NR₈R₉, hydroxy, nitro, cyano, tert-butoxycarbonyl, C1-C4 alkyl, C3-C8 cycloalkyl, or C1-C4 alkoxy; each R₈ and each R₉ is independently hydrogen, benzyloxycarbonyl (Cbz), tert-butoxycarbonyl (Boc), methoxycarbonyl, ethoxycarbonyl, p-toluenesulfonyl (Tos), trifluoroacetyl (Tfa), pivaloyl, benzoyl, 2,4-dimethoxybenzyl (Dmb), p-methoxybenzyl (PMB) or benzyl (Bn).

4. The compound according to claim 1, wherein A ring is selected from the group consisting of phenyl, pyridyl, pyrimidinyl, triazolyl, tetrazolyl, thiazolidinyl, pyrazolyl, oxazolyl, isooxazolyl and imidazolyl;

R₁ is methyl, ethyl, propyl or isopropyl;

R₂ is methyl, ethyl, propyl or isopropyl;

R₃ is cyclopropyl, cyclobutyl, cyclopentyl, cyclohexyl,

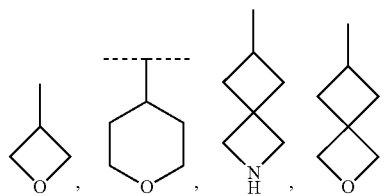

or —C(=O)R$_x$; wherein R$_x$ is C1-C4 alkyl or C3-C6 cycloalkyl;

R$_4$ is substituted or unsubstituted C6-C10 aryl, substituted or an unsubstituted benzyl, substituted or unsubstituted group having 1 to 3 hetero atoms selected from N, O or S as follows: 5-6 membered heterocyclyl or 5-6 membered heteroaryl; the substitution means that there is 1-3 substituents, each of which is independently fluorine, chlorine, bromine, hydroxyl, amino, nitro, cyano, methyl, ethyl, propyl, isopropyl, methoxy, ethoxy, propoxy or isopropoxy;

R$_5$ is hydrogen atom, substituted or unsubstituted methyl, substituted or unsubstituted ethyl, substituted or unsubstituted propyl, substituted or unsubstituted isopropyl,

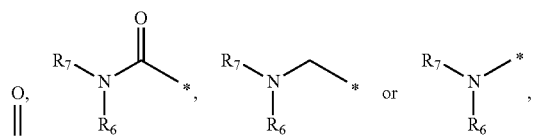

wherein R$_6$ and R$_7$ are each independently hydrogen atom, substituted or unsubstituted methyl, substituted or unsubstituted ethyl, substituted or unsubstituted propyl, substituted or unsubstituted isopropyl, substituted or unsubstituted piperidinyl; the substitution means that there is 1-3 substituents, each of which is independently fluorine, chlorine, bromine, hydroxyl, amino, methylamino, cyano, —N(CH$_3$)$_2$, —N(CH$_2$CH$_3$)$_2$, —N(CH$_3$)(CH$_2$CH$_3$), methyl, ethyl, propyl, isopropyl, methoxy, ethoxy, propoxy, isopropoxy;

or R$_6$ and R$_7$ together with the nitrogen atom to which they are attached form the following substitution or unsubstituted group: piperazinyl, homopiperazinyl, piperidinyl,

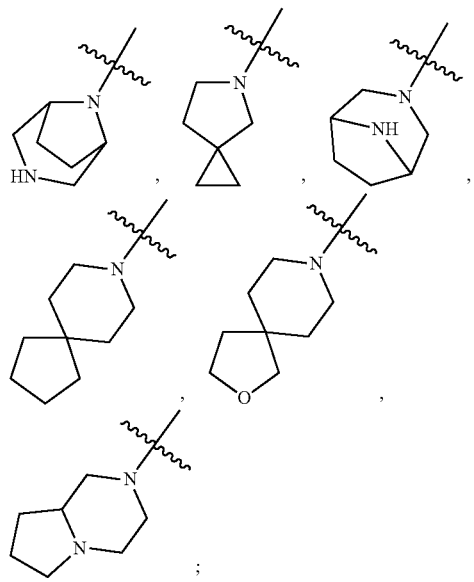

the substitution means that there is 1-3 substituents, each of which is independently fluorine, chlorine, bromine, hydroxy, nitro, cyano, methyl, ethyl, propyl, isopropyl, cyclopropyl, cyclobutyl, cyclopentyl, cyclohexyl, tert-butoxycarbonyl or NR$_8$R$_9$; each R$_8$ and each R$_9$ is independently hydrogen, tert-butoxycarbonyl (Boc), methoxycarbonyl, ethoxycarbonyl, pivaloyl, benzoyl or benzyl (Bn).

5. The compound according to claim 1, wherein A ring is selected from the group consisting of phenyl, triazolyl, tetrazolyl, thiazolidinyl, pyrazolyl and isoxazolyl; X is C or N;

R$_1$ is methyl;
R$_2$ is methyl;
R$_3$ is cyclopropyl, cyclopentyl,

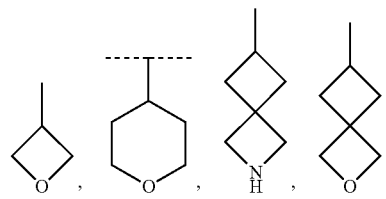

or —C(=O)R$_x$; wherein R$_x$ is C1-C4 alkyl or C3-C6 cycloalkyl;

R$_4$ is substituted or unsubstituted group as follows: phenyl, oxazolyl, 1,3-dioxolanyl; the substitution means that there is 1-3 substituents, each of which is independently F, Cl and methyl;

R$_5$ is absent, hydrogen atom, methyl,

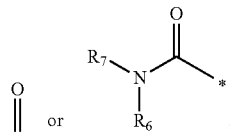

wherein R$_6$ and R$_7$ are each independently selected from hydrogen atom, substituted or unsubstituted methyl, substituted or unsubstituted ethyl, and the substituent is: —N(CH$_3$)$_2$; or R$_6$ and R$_7$ together with the nitrogen atom to which they are attached form substituted or unsubstituted group as follows: piperazinyl, homopiperazinyl,

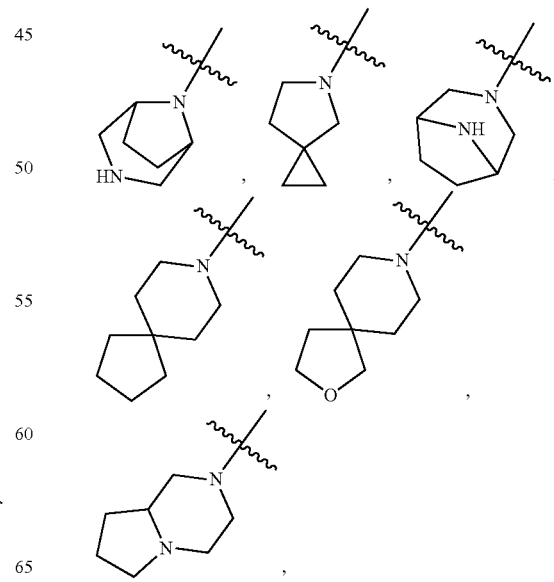

the substitution means that there is 1-3 substituents, each of which is independently methyl, ethyl, isopropyl, cyclopropyl, $NH_2$, $N(CH_3)_2$ or NHBoc.
6. The compound according to claim 1, wherein the compound is:
1
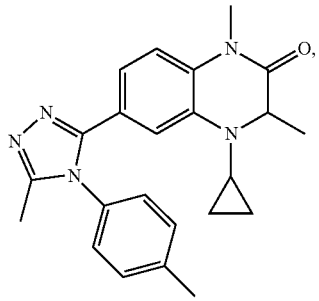
2
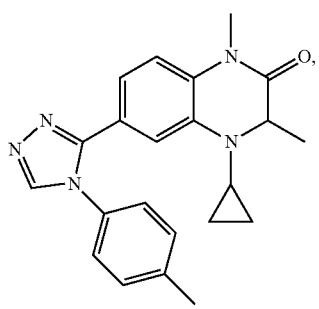
3
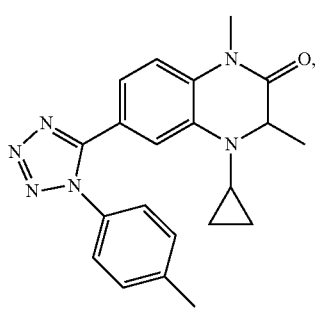
4
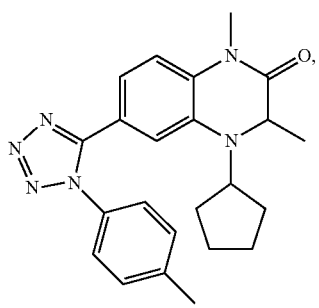
5
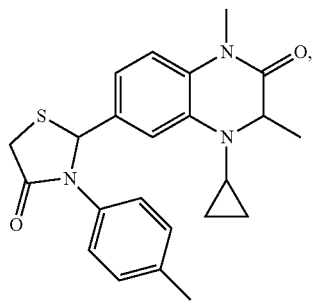
6
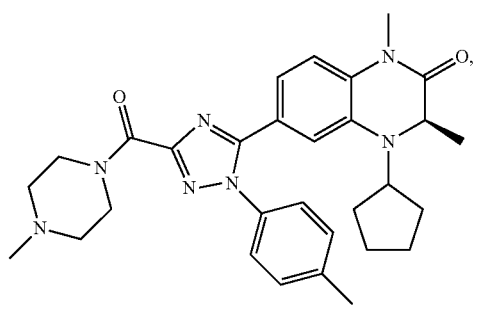
7
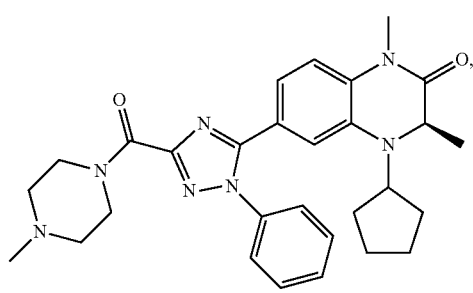
8
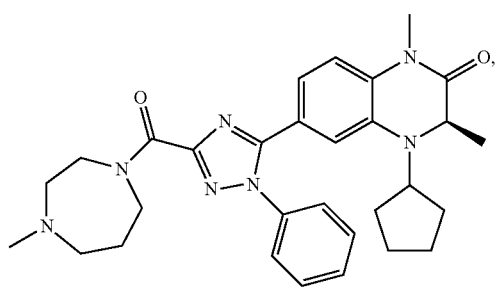
9
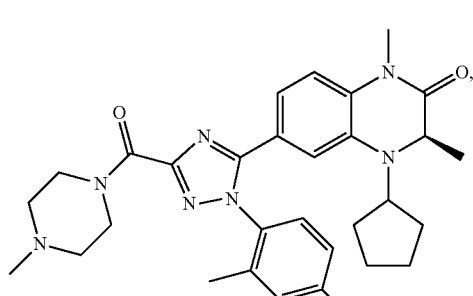

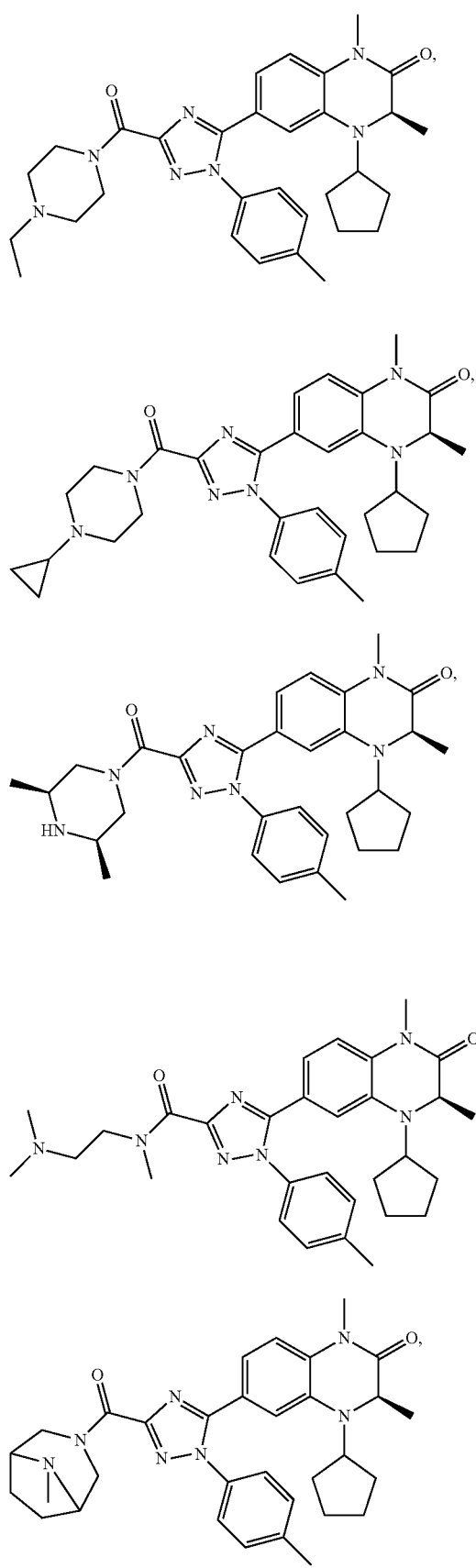
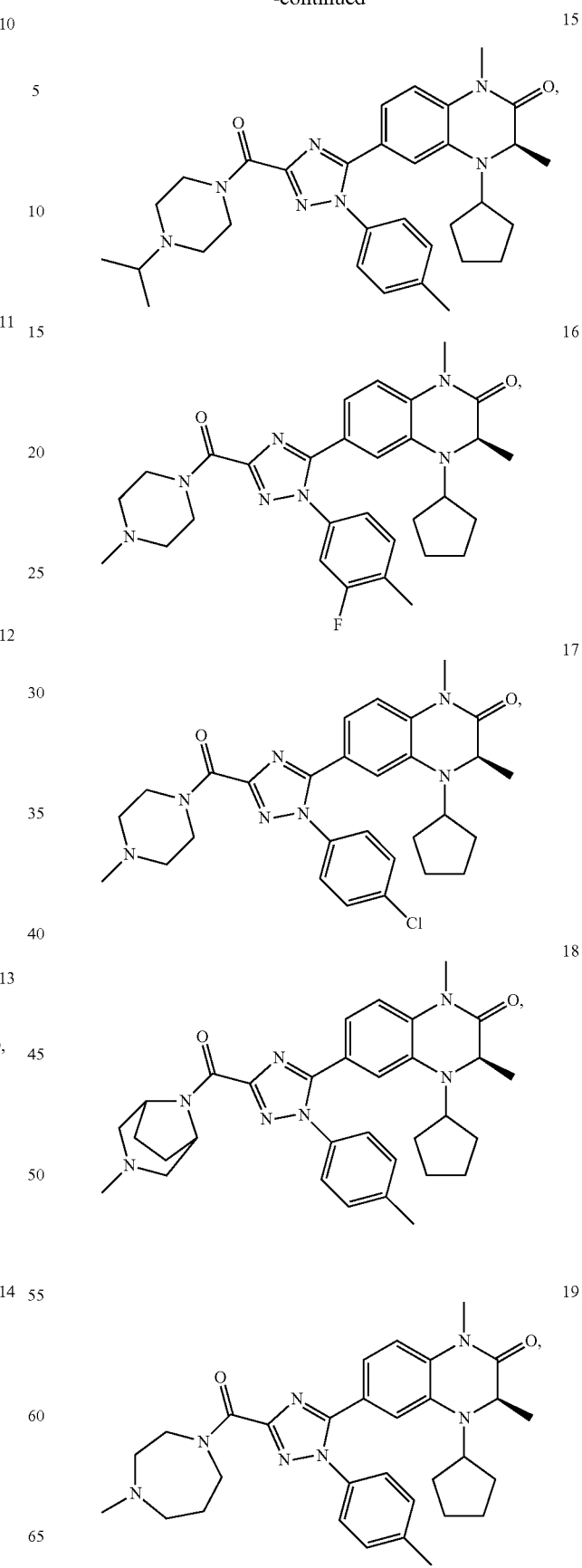

20 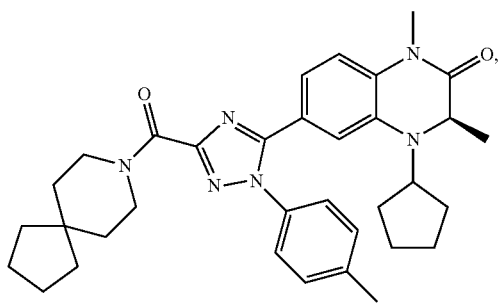
21 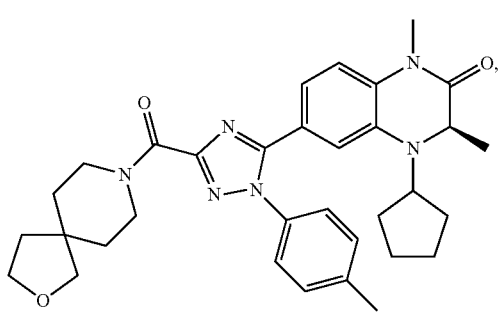
22 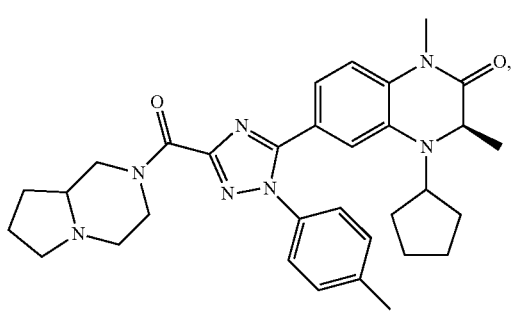
23 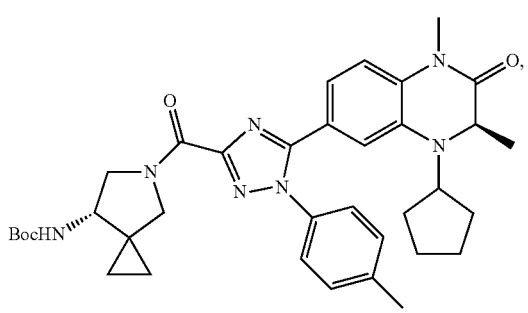
24 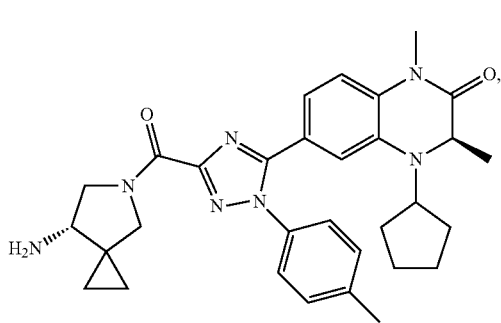
25 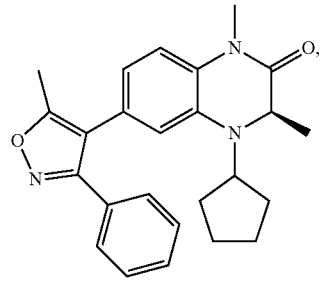
26 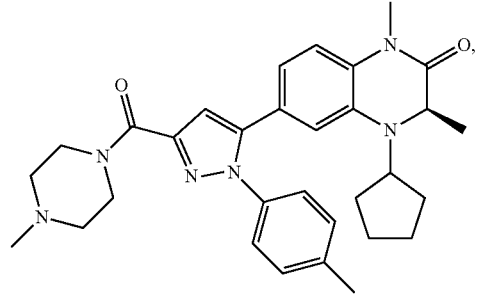
27 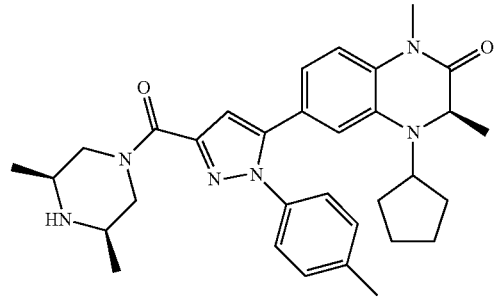
28 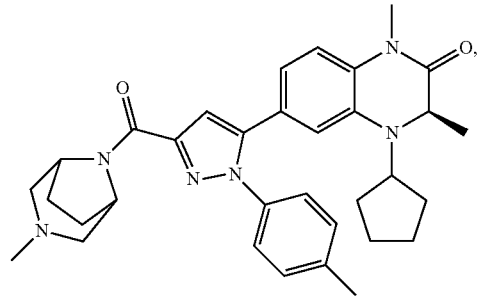
29 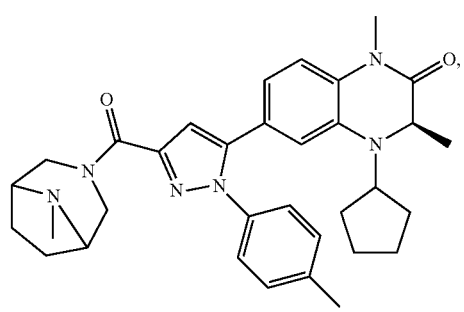

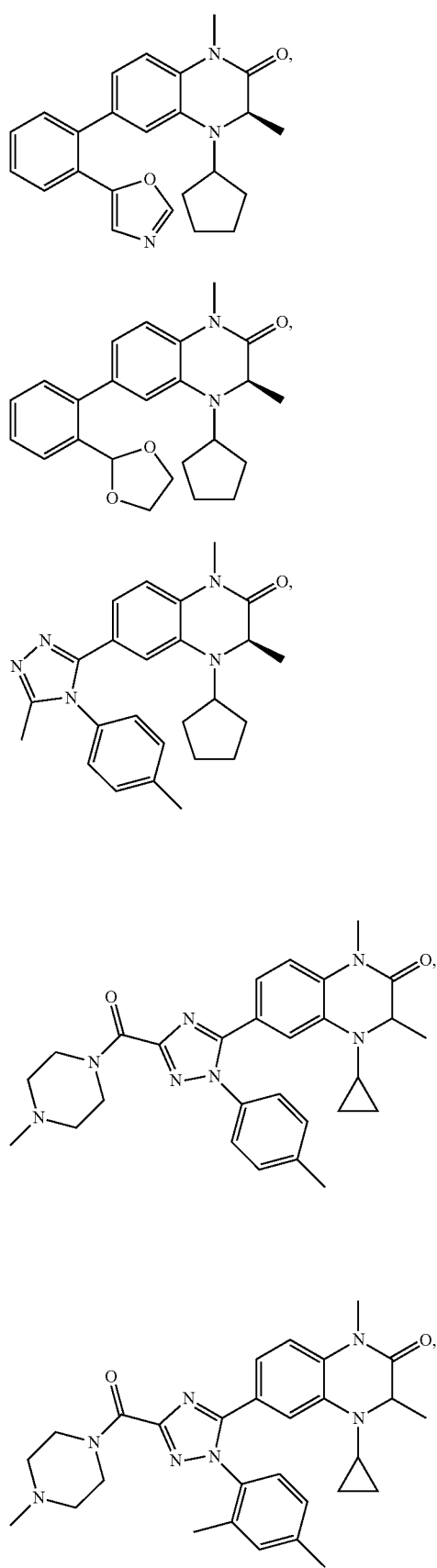
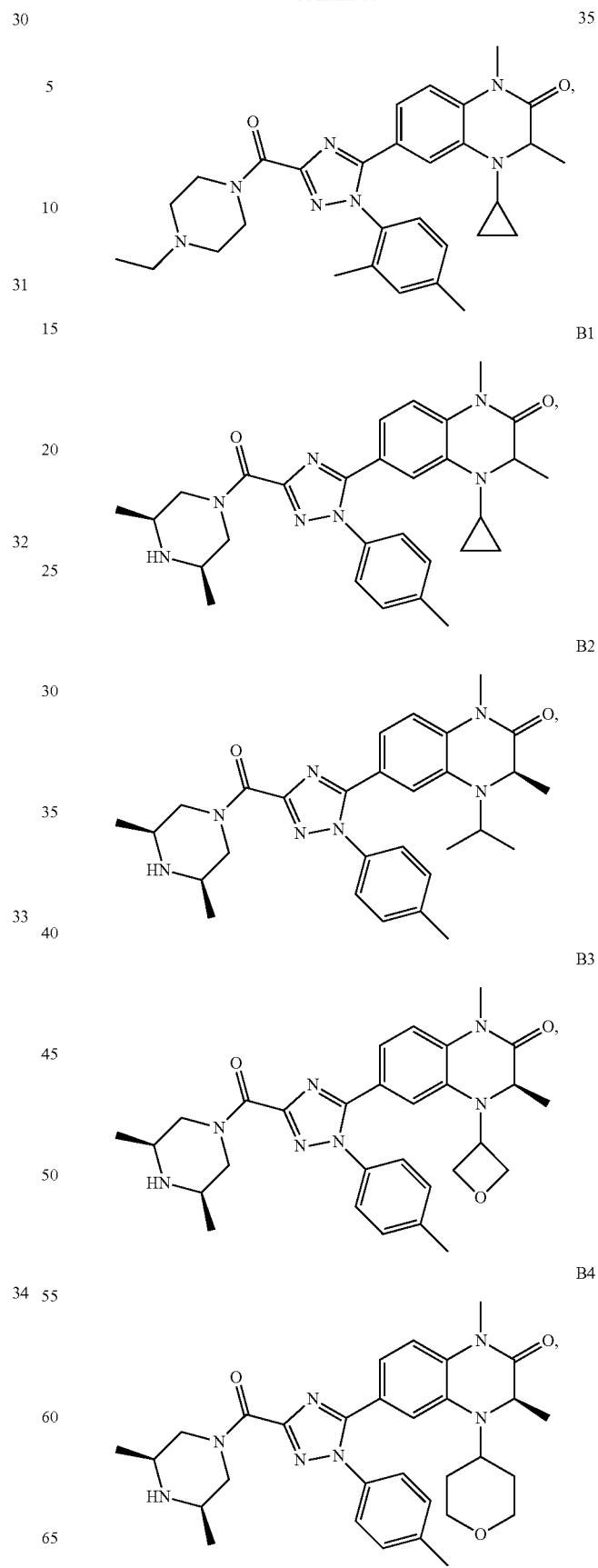

7. A method for the preparation of the compound according to claim 1, comprising the step of preparing a compound of the formula I by compound of the formula V,

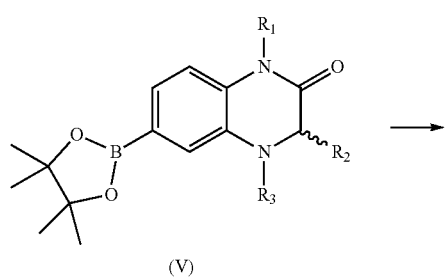

(V)

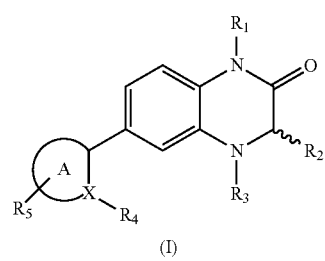

(I)

wherein each substituent and wavy line are as defined in claim 1.

8. A pharmaceutical composition comprising one or more of the compound of the formula (I) according to claim 1, or stereoisomer, prodrug, solvate, hydrate, crystal form or pharmaceutically acceptable salt thereof; and a pharmaceutically acceptable carrier.

9. A method for treating a disease mediated by a bromodomain recognition protein comprising administering the compound of the formula (I), or the stereoisomer, prodrug, protein targeted degradation conjugate, solvate, hydrate, crystal form, or the pharmaceutically acceptable salt thereof according to claim 1 to a subject in need thereof.

10. The method according to claim 9, wherein the disease mediated by the bromodomain recognition protein is selected from the group consisting of a malignant tumor, an immune disease, a cardiovascular disease and an inflammation.

11. The method according to claim 10, wherein the malignant tumor is selected from the group consisting of acute lymphoblastic leukemia, acute myeloid leukemia, B cell chronic lymphocytic leukemia, chronic myelomonocytic leukemia, midline cancer, lung cancer, B cell lymphoma, prostate cancer, gastric cancer, colorectal cancer, kidney cancer, liver cancer, breast cancer and pancreatic cancer.

* * * * *